(12) United States Patent
Solomon et al.

(10) Patent No.: US 11,820,988 B2
(45) Date of Patent: Nov. 21, 2023

(54) NANOPARTICLES AND BIOTEMPLATES WITH TUNABLE LENGTH AND METHODS OF MANUFACTURING THE SAME

(71) Applicant: Purdue Research Foundation, West Lafayette, IN (US)

(72) Inventors: Kevin Solomon, Lafayette, IN (US); Kok Zhi Lee, West Lafayette, IN (US); Yu-Hsuan Lee, West Lafayette, IN (US); Michael Harris, Lafayette, IN (US); Loretta Sue Loesch-Fries, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 591 days.

(21) Appl. No.: 16/805,305

(22) Filed: Feb. 28, 2020

(65) Prior Publication Data

US 2020/0277613 A1 Sep. 3, 2020

Related U.S. Application Data

(60) Provisional application No. 62/811,756, filed on Feb. 28, 2019.

(51) Int. Cl.
*C12N 15/10* (2006.01)
*C12N 15/70* (2006.01)

(52) U.S. Cl.
CPC ........... *C12N 15/70* (2013.01); *C12N 15/102* (2013.01); *C12N 2820/60* (2013.01)

(58) Field of Classification Search
CPC ........... C12N 2770/00022; C12N 2770/38022; C12N 2820/60; C12N 15/102; C12N 15/70; C12N 2770/00023; C12N 2770/20042; C12N 2810/609; C07K 14/005

See application file for complete search history.

(56) References Cited

U.S. PATENT DOCUMENTS

| 5,443,969 A * | 8/1995 | Wilson | C12N 15/8201 435/235.1 |
| 6,656,726 B1 * | 12/2003 | Fitzmaurice | C12N 15/8257 435/468 |
| 2014/0256581 A1 * | 9/2014 | Ben-Yoav | G01N 33/56983 506/14 |

OTHER PUBLICATIONS

Adigun et al., BSMV as a Biotemplate for Palladium Nanomaterial Synthesis. Langmuir, ACS Publications, 2017, vol. 33: 17-16-1724. (Year: 2017).*
Clare et al., Novel Inter-Subunit Contacts in Barley Stripe Mosaic Virus Revealed by Cryo-Electron Microscopy. Structure, 2015, vol. 23: 1815-1826; Cell Press. (Year: 2015).*
Devos et al., Practical limits of function prediction. Proteins: Structure, Function, and Genetics. 2000, vol. 41: 98-107. (Year: 2000).*
Hernandez-Garcia et al., Design and self-assembly of simple coat proteins for artificial viruses. Nat. Nanotechnology., 2014, vol. 9: 698-702. (Year: 2014).*
Whisstock et al., Prediction of protein function from protein sequence. Q. Rev. Biophysics., 2003, vol. 36 (3): 307-340. (Year: 2003).*
Francis et al., Strategies to Optimize Protein Expression UNIT 5.24 in *E. coli* . Curr. Protocols in Prot. Sci., 2010, supplement 61: 5.24.1-5.24.29. (Year: 2010).*

* cited by examiner

*Primary Examiner* — Ganapathirama Raghu
(74) *Attorney, Agent, or Firm* — Reichel Stohry Dean LLP; Natalie J. Dean

(57) ABSTRACT

Methods and nucleic acid sequences for the synthesis of biotemplates in a non-plant based expression system are provided. Such biotemplates include Barley stripe mosaic virus viral-like particles (BSMV-VLPs) that are capable of self-assembly due to being operatively linked with an origin of self-assembly with the Barley stripe mosaic virus capsid protein (BSMV-CP). Also provided are BSMV-VLPs that are capable of self-assembly due one or more site-directed mutations on the BSMV-CP, and BSMV-VLPs that exhibit enhanced stability due to such site-directed mutation(s).

10 Claims, 9 Drawing Sheets

Specification includes a Sequence Listing.

NANOPARTICLES AND BIOTEMPLATES WITH TUNABLE LENGTH AND METHODS OF MANUFACTURING THE SAME

PRIORITY

This application is related to and claims priority benefit of U.S. Provisional Patent Application Ser. No. 62/811,756 to Solomon et al. filed Feb. 28, 2019. The entire content of the aforementioned priority application is hereby incorporated by reference in its entirety into this disclosure.

BACKGROUND

A nanoparticle is a nano-object or particle between 1 and 100 nanometers (nm) in size. These structures are of scientific interest because of their beneficial physical, chemical, and electronic properties which lead to great potential for a broad range of applications in various fields, such as biomedicine, materials science, electronics, consumer products, cosmetics, pharmaceuticals, transportation, and energy. Of particular interest in the optoelectrical, electrical, biochemical, and medical fields are metal nanoparticles or metallized nanoparticles due to their unique properties.

The properties and functions of nanoparticles and nanostructures are often closely correlated with the size, shape, structure, surface area, and/or composition thereof. However, achieving the synthesis of nanoparticles having controllable dimensions and morphology, as well as high purity, quantity and quality remains a challenge. One type of bottom-up nanofabrication called biotemplating has proven to be viable means to easily and inexpensively produce nanomaterials on a large scale. More specifically, biotemplating is the use of naturally occurring biomolecules to develop nanomaterials of similar morphology, hierarchical complexity, and nanometric precision. Naturally occurring biomolecules, such as viruses, DNA, proteins, and RNA, offer highly ordered morphologies and well-defined architectures and organizations and, thus, provide the ability to generate uniform and monodisperse nanomaterials.

Viruses specifically are attractive scaffolds for the construction of hierarchical complex nanomaterials due to their unique advantages for applications in catalysis, nanocircuitry, chemical sensing, biocatalysis, memory devices, and light harvesting. Plant viruses, in particular, are small in size, display structural symmetry, ease of functionalization, and monodispersity, and spontaneously self-assemble into uniform nanoscale structures. Additionally, they often have wide range of stabilities to temperature, pH, salt, chemicals, and protease degradation. Plant viruses are relatively easy to purify as they lack membranes and have one or two protein capsid assemblies that are structurally defined. In addition to allowing for the production of novel nanomaterials in a very precise and controlled fashion, the ability to genetically and chemically modify plant viruses also allows for the insertion or replacement of selected amino acids on virus capsids for uses ranging from bioconjugation to mineralization.

The M13 bacteriophage, the Tobacco mosaic virus (TMV), and their engineered variants remain the prevalent biotemplates employed in conventional nanowire and nanorod synthesis. TMV, in particular, has been exploited as a biotemplate in various applications, including battery electrodes, memory devices, catalysts, and chemical sensors, which are coated with metals such as silver, platinum, aluminum, palladium, gold and gold/palladium alloy. The Barley stripe mosaic virus (BSMV) has also been utilized for production of organic-metal nanorods, but to a lesser degree and such methods are limited to in-planta production, which limits its development.

Conventional nanoparticle synthesis platforms face certain drawbacks, especially with respect to viral systems produced in-planta. In addition to limiting development, the genomes of in-planta-synthesized viruses are subject to evolutionary pressures that may remove engineered modifications designed to enhance biotemplating functionality if such removal benefits viral fitness. As these viruses are plant pathogens, virus-producing plants must also be grown in specialized facilities to control and/or prevent the spread of the pathogen to wild plants. Furthermore, the viral replication cycle in plants requires between 2-3 weeks, which results in a long and complicated process to extract a relatively small quantity of viruses. Finally, the conventional production of metal nanoparticles in particular requires varying conditions (e.g., pHs, temperatures, etc.) that may destabilize the produced nanoparticles. Accordingly, there is a need for an alternative approach that is inexpensive, highly precise, robust, efficient, and ideally tunable for particular applications.

BRIEF SUMMARY

Novel methods for manufacturing nanoparticle biotemplates are provided. In at least one embodiment, such methods comprise introducing into a host a nucleic acid sequence encoding a Barley stripe mosaic virus coat protein (BSMV-CP) comprising one or both of: (a) an origin of self-assembly (OAS) derived from a virus operatively linked with the BSMV-CP, and (b) at least one site-directed mutation on the BSMV-CP to strengthen an interaction between at least two BSMV-CP subunits. The nucleic acid sequence is then expressed in an expression system (microbial-based or otherwise) to allow expression of the BSMV-CP, which produces self-assembled BSMV viral-like particles (BSMV VLPs). The method further comprises isolating the BSMV VLPs from the expression system.

In at least one embodiment, the OAS is derived from Tobacco mosaic virus. Additionally, the OAS may comprise SEQ ID NO: 11 or a functional equivalent thereof.

Additionally or alternatively, the step of expressing the nucleic acid sequence may comprise: constructing a plasmid or an expression vector comprising the nucleic acid sequence and transforming the plasmid or expression vector into the host. In certain embodiments, the host may be *Escherichia coli*. Furthermore, the step of expressing the nucleic acid sequence may be performed at a neutral pH. In at least one additional embodiment, the BSMV-CP may be fused with a linker region and comprise at least one site-directed mutation on the BSMV-CP to strengthen an interaction between at least two BSMV-CP subunits.

In an exemplary embodiment, the BSMV-CP further comprises a fusion of BSMV-CP, a linker region, and the OAS. There, the method may further comprise selecting a length of the linker region based on a desired length in the resulting BSMV VLPs such that the VLPs themselves are tunable and/or customizable.

Methods of the present disclosure may further comprise the step of synthesizing one or more nanoparticles using the resulting VLPs. Optionally, the method may comprise coating at least a surface of the resulting VLPs with a metal, where desired. Such coating may be performed using adsorption, for example, or via any other modality now known in the art or hereinafter developed. Still further, the methods hereof may comprise the step of performing microbial reduction of the resulting VLPs.

As previously noted, embodiments of the presently disclosed methods may comprise BSMV-CP comprising at least one site-directed mutation on the BSMV-CP to strengthen an interaction between at least two BSMV-CP subunits. There, for example and without limitation, the at least one site-directed mutation may be at one or more of the following residues: E37Q, E37R, E62Q, D68N, D70N, D101N, D101R, and D101K.

Novel nanoparticles are also described herein, as well as methods for manufacturing the same. In at least one exemplary embodiment, the present disclosure provides a nanoparticle manufactured according to a process comprising the steps of: introducing into a host a nucleic acid sequence encoding a Barley stripe mosaic virus coat protein (BSMV-CP) comprising one or both of: (a) an origin of self-assembly (OAS) derived from a virus operatively linked with the BSMV-CP, and (b) at least one site-directed mutation on the BSMV-CP to strengthen an interaction between at least two BSMV-CP subunits; expressing the nucleic acid sequence in an expression system to allow expression of the BSMV-CP and produce self-assembled BSMV viral-like particles (BSMV VLPs); isolating the BSMV VLPs from the expression system; and synthesizing one or more nanoparticles using the BSMV VLPs as a biotemplate. There, the nucleic acid sequence may be modified such that it further encodes a linker region comprising a length that is fused with at least the BSMV-CP. As the length of the linker region will directly correlate the size shapes of the VLPs produced through the method, the length of the linker region may be specifically selected to customize the dimensions of the resulting nanoparticles. In other words, the length of the linker region may directly correlate with the length of the resulting nanoparticles by function of influencing the size and/or shape of the VLPs biotemplates.

Additionally, where the BSMV-CP comprises the at least one site-directed mutation, such site-directed mutation may be at one or more of the following residues thereof: E37Q, E37R, E62Q, D68N, D70N, and D101N.

In at least one exemplary embodiment of the nanoparticles provided herein, the step of introducing into a host a nucleic acid sequence may further comprise: constructing a plasmid or expression vector comprising the nucleic acid sequence and transforming the plasmid or expression vector into the host (for example, and without limitation, *Escherichia coli*). Optionally, the OAS comprises SEQ ID NO: 11 or a functional equivalent thereof. The expression system may comprise any non-plant based expression system including a microbial-based, insect-based, or mammalian-based expression system.

Novel nucleic acid sequences are also provided herein. In at least one embodiment, a nucleic acid for synthesis of a nanoparticle biotemplate is described, such nucleic acid comprising all or part of a sequence encoding a Barley stripe mosaic virus coat protein (BSMV-CP) operatively linked to a linker region having a length and an origin of self-assembly (OAS) derived from a virus. In at least one exemplary embodiment, the BSMV-CP may comprise a protein sequence selected from a group consisting of: SEQ ID NO: 2, SEQ ID NO: 3; SEQ ID NO: 4, SEQ ID NO: 5, SEQ ID NO: 6, SEQ ID NO: 7, SEQ ID NO: 8, SEQ ID NO: 9, SEQ ID NO: 10, or comprise a functional equivalent of one of SEQ ID NOS: 2-10. Additionally or alternatively, a portion of the sequence for encoding the OAS may comprise SEQ ID NO: 11 or a functional equivalent thereof. In at least one exemplary embodiment, the sequence comprises SEQ ID NO: 15 or a functional equivalent thereof.

BRIEF DESCRIPTION OF THE SEQUENCE LISTINGS

SEQ ID NO: 1 is an amino acid sequence of a wild-type Barley stripe mosaic virus coat protein (BSMV-CP): N-MPNVSL-TAKGGGHYIEDQWDTQVVEAGVFDDWWVHVEAW NKFLDNLRGINFSVASS RSQVAEYLAALDRDLPAD-VDRRFAGARGQIGSPNYLPAPKFFRLDKRTIAEL-TRLSRLTD QPHNNRDIELNRAKRATTNPSP-PAQAPSENLTLRDVQPLKDSALHYQYVLIDLQSARLP VYTRKTFERELALEWIIPDAEEA-C;

SEQ ID NO: 2 is an artificial amino acid sequence of at least one exemplary embodiment of a BSMV-CP having a point mutation at residue D68N according to the present disclosure: N-MPNVSL-TAKGGGHYIEDQWDTQVVEAGVFDDWWVHVEAW NKFLDNLRGINFSVASS RSQVAEYLAALNRDLPAD-VDRRFAGARGQIGSPNYLPAPKFFRLDKRTIAEL-TRLSRLTD QPHNNRDIELNRAKRATTNPSP-PAQAPSENLTLRDVQPLKDSALHYQYVLIDLQSARLP VYTRKTFERELALEWIIPDAEEA-C;

SEQ ID NO: 3 is an artificial amino acid sequence of at least one exemplary embodiment of a BSMV-CP having a point mutation at residue D70N according to the present disclosure: N-MPNVSL-TAKGGGHYIEDQWDTQVVEAGVFDDWWVHVEAW NKFLDNLRGINFSVASS RSQVAEYLAALDRNLPAD-VDRRFAGARGQIGSPNYLPAPKFFRLDKRTIAEL-TRLSRLTD QPHNNRDIELNRAKRATTNPSP-PAQAPSENLTLRDVQPLKDSALHYQYVLIDLQSARLP VYTRKTFERELALEWIIPDAEEA-C;

SEQ ID NO: 4 is an artificial amino acid sequence of at least one exemplary embodiment of a BSMV-CP having a point mutation at residue D101K according to the present disclosure: N-MPNVSL-TAKGGGHYIEDQWDTQVVEAGVFDDWWVHVEAW NKFLDNLRGINFSVASS RSQVAEYLAALDRDLPAD-VDRRFAGARGQIGSPNYLPAPKFFRLKKRTIAEL-TRLSRLTD QPHNNRDIELNRAKRATTNPSP-PAQAPSENLTLRDVQPLKDSALHYQYVLIDLQSARLP VYTRKTFERELALEWIIPDAEEA-C;

SEQ ID NO: 5 is an artificial amino acid sequence of at least one exemplary embodiment of a BSMV-CP having a point mutation at residue D101N according to the present disclosure, such mutant being verified as capable of self-assembly: N-MPNVSL-TAKGGGHYIEDQWDTQVVEAGVFDDWWVHVEAW NKFLDNLRGINFSVASS RSQVAEYLAALDRDLPAD-VDRRFAGARGQIGSPNYLPAPKFFRLNKRTIAEL-TRLSRLTD QPHNNRDIELNRAKRATTNPSP-PAQAPSENLTLRDVQPLKDSALHYQYVLIDLQSARLP VYTRKTFERELALEWIIPDAEEA-C;

SEQ ID NO: 6 is an artificial amino acid sequence of at least one exemplary embodiment of a BSMV-CP having a point mutation at residue D101R according to the present disclosure: N-MPNVSL-TAKGGGHYIEDQWDTQVVEAGVFDDWWVHVEAW NKFLDNLRGINFSVASS RSQVAEYLAALDRDLPAD-VDRRFAGARGQIGSPNYLPAPKFFRLRKRTIAEL-TRLSRLTD QPHNNRDIELNRAKRATTNPSP-PAQAPSENLTLRDVQPLKDSALHYQYVLIDLQSARLP VYTRKTFERELALEWIIPDAEEA-C;

SEQ ID NO: 7 is an artificial amino acid sequence of at least one exemplary embodiment of a BSMV-CP having a point mutation at residue E37Q according to the present disclosure: N-MPNVSL-TAKGGGHYIEDQWDTQVVEAGVFDDWWVHVQAW NKFLDNLRGINFSVASS RSQVAEYLAALDRDLPAD-VDRRFAGARGQIGSPNYLPAPKFFRLDKRTIAEL-TRLSRLTD QPHNNRDIELNRAKRATTNPSP-PAQAPSENLTLRDVQPLKDSALHYQYVLIDLQSARLP VYTRKTFERELALEWIIPDAEEA-C;

SEQ ID NO: 8 is an artificial amino acid sequence of at least one exemplary embodiment of a BSMV-CP having a point mutation at residue E37R according to the present disclosure: N-MPNVSL-TAKGGGHYIEDQWDTQVVEAGVFDDWWVHVRAW NKFLDNLRGINFSVASS RSQVAEYLAALDRDLPAD-VDRRFAGARGQIGSPNYLPAPKFFRLDKRTIAEL-TRLSRLTD QPHNNRDIELNRAKRATTNPSP-PAQAPSENLTLRDVQPLKDSALHYQYVLIDLQSARLP VYTRKTFERELALEWIIPDAEEA-C;

SEQ ID NO: 9 is an artificial amino acid sequence of at least one exemplary embodiment of a BSMV-CP having a point mutation at residue E62Q according to the present disclosure, such mutant being verified as capable of self-assembly: N-MPNVSL-TAKGGGHYIEDQWDTQVVEAGVFDDWWVHVEAW NKFLDNLRGINFSVASS RSQVAQYLAALDRDLPAD-VDRRFAGARGQIGSPNYLPAPKFFRLDKRTIAEL-TRLSRLT DQPHNNRDIELNRAKRATTNPSP-PAQAPSENLTLRDVQPLKDSALHYQYVLIDLQSARL PVYTRKTFERELALEWIIPDAEEA-C;

SEQ ID NO: 10 is an artificial amino acid sequence of at least one exemplary embodiment of a BSMV-CP having point mutations at both residues E62Q and D101N according to the present disclosure: N-MPNVSL-TAKGGGHYIEDQWDTQVVEAGVFDDWWVHVEAW NKFLDNLRGINFSVASS RSQVAQYLAALDRDLPAD-VDRRFAGARGQIGSPNYLPAPKFFRLNKRTIAEL-TRLSRLT DQPHNNRDIELNRAKRATTNPSP-PAQAPSENLTLRDVQPLKDSALHYQYVLIDLQSARL PVYTRKTFERELALEWIIPDAEEA-C;

SEQ ID NO: 11 is a DNA sequence that encodes a wild-type origin of self-assembly derived from a Tobacco mosaic virus: 5'-GTATTGTT-TATAGAAATAATATAAAATTAGGTTTGAGAGAGAA-GATTACAAACGTG AGAGACGGAGGGCCCATG-GAACTTACAGAAGAAGTCGTTGATGAGTTCATGG AAGA TGTCCCTATGTC-GATCAGGCTTGCAAAGTTTCGATCTCGAACCG-GAAAAAAGAGTGA TGTCCGCAAAGGGAAAAATA-3';

SEQ ID NO: 12 is a DNA sequence that encodes a wild-type BSMV-CP: 5'-ATGCCCAACGTAT-CACTGACAGCGAAAGGGGGAGGTCATTA-CATCGAAGATCAGTG GGA-TACGCAAGTCGTCGAAGCAGGAGTGTTCGACGAC TGGTGGGTGCATGTAGAGG CCTG-GAATAAGTTTCTTGACAATCTGCGCGGCATCAAT-TTTTCCGTCGCCAGCAGTC GCT-CACAAGTAGCAGAGTATTTGGCTGCTTTGGATCGT GACCTTCCGGCTGACGTTG ATCGTCGTTTCGCGGGTGCACGTGGT-CAAATCGGCAGCCCCAATTACTTACCAGCAC CTAAATTTTTTCGTCTTGATAAACGTACAATCGCT-GAATTGACACGTTTGTCGCGCTT GACG-GATCAGCCCCACAACAATCGTGATATCGAGT-TAAATCGCGCAAAACGCGCAA CAACAAATCCTAGCCCACCTGCT-CAAGCCCCGAGCGAAAACCTTACACTGCGCGAC GTGCAACCCTTAAAGGACTCCGCGTTACAT-TATCAGTATGTCCTTATTGATCTTCAGT CCGCACGCTTGCCTGTGTATACCCGCAA-GACTTTCGAGCGCGAGCTGGCTCTGGAGT GGAT-CATTCCAGATGCAGAGGAAGCATAA-3';

SEQ ID NO: 13 is an artificial sequence of at least one exemplary embodiment that encodes a linker region according to the present disclosure;

SEQ ID NO: 14 is an artificial DNA sequence of at least one exemplary embodiment that encodes a BSMV-CP (SEQ ID NO: 12) fused with an OAS derived from TMV (SEQ ID NO: 11);

SEQ ID NO: 15 is an artificial DNA sequence of at least one exemplary embodiment that encodes a BSMV-CP (SEQ ID NO: 12) fused with a linker region and an OAS derived from TMV (SEQ ID NO: 11);

SEQ ID NO: 16 is an artificial DNA sequence of a plasmid vector pET21-BSMV-D70N that encodes the protein of SEQ ID NO: 3;

SEQ ID NO: 17 is an artificial DNA sequence of a plasmid vector pET21-BSMV-D68N that encodes the protein of SEQ ID NO: 2;

SEQ ID NO: 18 is an artificial DNA sequence of a plasmid vector pET21-BSMV-D101K that encodes the protein of SEQ ID NO: 4;

SEQ ID NO: 19 is an artificial DNA sequence of a plasmid vector pET21-BSMV-D101R that encodes the protein of SEQ ID NO: 6;

SEQ ID NO: 20 is an artificial DNA sequence of a plasmid vector pET21-BSMV-E37Q that encodes the protein of SEQ ID NO: 7;

SEQ ID NO: 21 is an artificial DNA sequence of a plasmid vector pET21-BSMV-E37R that encodes the protein of SEQ ID NO: 8;

SEQ ID NO: 22 is an artificial DNA sequence of a plasmid vector pET21-BSMV-D101N that encodes the protein of SEQ ID NO: 5;

SEQ ID NO: 23 is an artificial DNA sequence of a plasmid vector pET21-BSMV-E62Q that encodes the protein of SEQ ID NO: 9;

SEQ ID NO: 24 is an artificial DNA sequence of a plasmid vector pET21-BSMV-E62Q/D101N that encodes the protein of SEQ ID NO: 10;

SEQ ID NO: 25 is an artificial DNA sequence of a plasmid vector pET21-BSMV; and SEQ ID NO: 26 is an artificial DNA sequence of a plasmid vector pET21-BSMV-Linker-OAS that encodes a BSMV-CP (SEQ ID NO: 12) fused with a linker region and an OAS derived from TMV (SEQ ID NO: 11).

In addition to the foregoing, written Sequence Listings for the above-described sequences are appended hereto and the same Sequence Listing is provided in computer readable form encoded in a file filed herewith and herein incorporated by reference. The information recorded in computer readable form is identical to the written Sequence Listing provided herein, pursuant to 37 C.F.R. § 1.821(f).

BRIEF DESCRIPTION OF THE DRAWINGS

The disclosed embodiments and other features, advantages, and aspects contained herein, and the matter of attaining them, will become apparent in light of the following detailed description of various exemplary embodiments of the present disclosure. Such detailed description will be better understood when taken in conjunction with the accompanying drawings, wherein:

FIG. 5, subpart (b) shows a schematic representation that engineered BSMV-VLPs with increased coat protein interaction are less susceptible to extreme pH and low calcium ion concentrations;

FIG. 5, subpart (c) shows a schematic representation of all BSMV protein constructs expressed and produced in a microbial-based chassis;

FIG. 10 shows PAGE analysis results of BSMV-CP expression conducted at different inducer agent concentrations, with subpart (a) representing soluble fraction yield at 0.01 mM, 0.05 mM, 0.075 mM, and 0.10 mM, and subpart (b) representing the effect of final pellet resuspension buffers on solubilizing BSMV-CP in water (A), Tris buffer (B), and sodium phosphate buffer (C); arrow marks indicating BSMV-CP protein at ~22.5 kDa;

FIG. 11 are TEM visualizations of BSMV-OAS after 68% sucrose cushion, with subpart (a) showing the top layer supernatant and subpart (b) showing the bottom of the 68% sucrose cushion;

Figure 1:
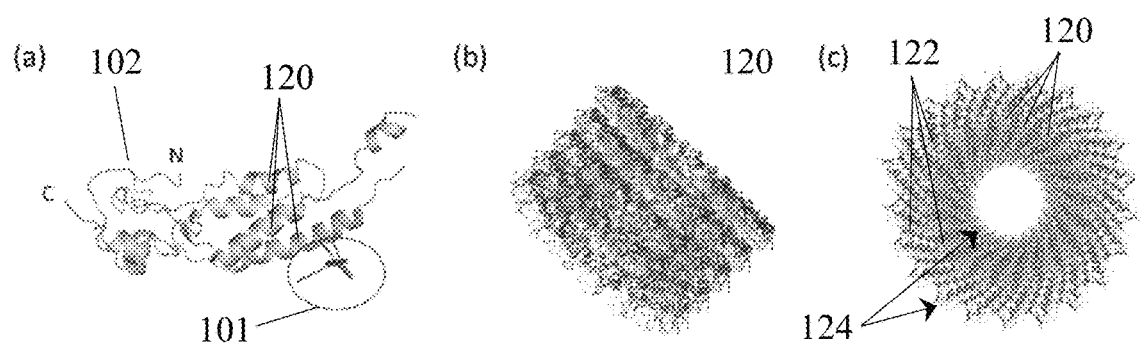
FIG. 1 shows various views of a graphical model of the structure of the Barley stripe mosaic virus (BSMV) (PDB: 5A7A), with subpart (a) showing a perspective view of a BSMV capsid protein; subpart (b) showing a side view of an assembled BSMV virion; and subpart (c) showing a top-down view of assembled BSMV capsid proteins (images adapted from Clare et al., *Novel Inter-Subunit Contacts in Barley Stripe Mosaic Virus Revealed by Cryo-Electron Microscopy*, Structure, Oct. 6, 2015; 23(10): 1815-1826)

While the present disclosure is susceptible to various modifications and alternative forms, exemplary embodiments thereof are shown by way of example in the drawings and are herein described in detail.

DETAILED DESCRIPTION

For the purposes of promoting an understanding of the principles of the present disclosure, reference will now be made to the embodiments illustrated in the drawings and specific language will be used to describe the same. It will nevertheless be understood that no limitation of scope is intended by the description of these embodiments. On the contrary, this disclosure is intended to cover alternatives, modifications, and equivalents as may be included within the spirit and scope of this application as defined by the appended claims. As previously noted, while this technology may be illustrated and described in one or more preferred embodiments, the compositions, systems and methods hereof may comprise many different configurations, forms, materials, and accessories.

In the following description, numerous specific details are set forth in order to provide a thorough understanding of the present disclosure. Particular examples may be implemented without some or all of these specific details and it is to be understood that this disclosure is not limited to particular biological systems, which can, of course, vary.

Furthermore, wherever feasible and convenient, like reference numerals are used in the figures and the description to refer to the same or like parts or steps. The drawings are in a simplified form and not to precise scale. It is understood that the disclosure is presented in this manner merely for explanatory purposes and the principles and embodiments described herein may be applied to devices and/or system components that have dimensions/configurations other than as specifically described herein. Indeed, it is expressly contemplated that the size and shapes of the composition and system components of the present disclosure may be tailored in furtherance of the desired application thereof.

Various techniques and mechanisms of the present disclosure will sometimes describe a connection or link between two components. Words such as attached, linked, coupled, connected, fused, and similar terms with their inflectional morphemes are used interchangeably, unless the difference is noted or made otherwise clear from the context. These words and expressions do not necessarily signify direct connections, but include connections through mediate components and devices. It should be noted that a connection between two components does not necessarily mean a direct, unimpeded connection, as a variety of other components may reside between the two components of note. Consequently, a connection does not necessarily mean a direct, unimpeded connection unless otherwise noted.

Similarly, the phrase "operatively linked" as used herein refers to elements or structures in a nucleic acid sequence or amino acid sequence that are linked by operative ability and not physical location. The elements or structures are capable of, or characterized by, accomplishing a desired operation. It is recognized by one of ordinary skill in the art that it is not necessary for elements or structures in a nucleic acid sequence to be in a tandem or adjacent order to be operatively linked.

Unless defined otherwise, all technical and scientific terms used herein have the same meaning as commonly understood by one of skill in the relevant arts. Although any methods and materials similar to or equivalent to those described herein can be used in the practice or testing of the subject of the present application, the preferred methods and materials are described herein. Additionally, as used in this specification and the appended claims, the singular forms "a", "an" and "the" include plural referents unless the content clearly dictates otherwise. Thus, for example, reference to "an RNA" includes a combination of two or more RNAs; reference to "bacteria," unless otherwise specified, includes mixtures of bacteria, and the like.

The term "about," as used herein, means approximately, in the region of, roughly or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about."

The terms "polypeptide," "peptide," and "protein" are used interchangeably herein to refer to a polymer of amino acid residues, a polypeptide, or a fragment of a polypeptide, peptide, or fusion polypeptide. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the corresponding naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refer to compounds that have the same basic chemical structure as a naturally occurring amino acid, i.e. a carbon that is bound to a hydrogen, a carboxyl group, an amino group, and an R group (e.g., homoserine, norleucine, methionine sulfoxide, methionine methyl sulfonium). Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

"Nucleic acid" refers to deoxyribonucleotides or ribonucleotides and polymers thereof in either single- or double-stranded form and complements thereof. The term encompasses nucleic acids containing known nucleotide analogs or modified backbone residues or linkages, that are synthetic, naturally occurring, and non-naturally occurring, have similar binding properties as the reference nucleic acid, and metabolized in a manner similar to the reference nucleotides. Nucleotides may be referred to by their commonly accepted single-letter codes.

The term "interaction domain" refers to peptides or proteins (that may be glycosylated or otherwise modified), that are adapted to specifically interact with target regions (or targets) on other molecules differing from themselves. For example, and without limitation, a viral coat protein may comprise an interaction domain that is adapted to specifically interact with an origin of self-assembly (i.e. the target) as defined below.

As used herein, the terms "origin of self-assembly," "origin of assembly," and "OAS" each refer to an internal RNA stem-loop sequence present in the viral RNA genome that is adapted to interact with viral coat proteins of the virus or other interaction domains to form one or more structures having a substantially defined geometry and including three (3) or more units. An OAS may be the target for disk binding in assembly initiation and may be specifically recognized by the viral coat protein disk aggregate (see FIG. 3). For example, with respect to viruses, and TMV in particular, a TMV coat protein may be the interaction domain and interact/bind with the origin of assembly to spontaneously form an initiation complex to which additional subunits can rapidly bind to create a hairpin loop or other stacking formation. An origin of self-assembly may be connected to the interaction domain by a linker region (also referred to herein as a "linker" or "linker sequence").

The phrase "derived from" refers to a component that is isolated from or made using a specific molecule or organism, or information from a specific molecule or organism. As such, as used herein, the phrase "derived from genetic material encoding" refers to something that includes a peptide or protein which could have been substantially produced by transcription of DNA and/or translation of RNA encoding that peptide or protein, or a larger protein of which it forms a part, followed if necessary by cleavage (natural or unnatural) and/or post-translational modification. It will be apparent that a peptide or protein will be derived from genetic material even if the actual genetic material encoding it differs through degeneracy in the genetic code or conservative substitution or the like. Similarly, a DNA or nucleotide "coding sequence" or "sequence encoding" a particular polypeptide or protein refers to a nucleic acid sequence that is transcribed and translated into a product (e.g., a polypeptide or protein) when placed under the control of appropriate regulatory sequences.

As used herein, the term "encodes" refers to any process whereby the information in a polymeric macromolecule or sequence string is used to direct the production of a second molecule or sequence string that is different from the first molecule or sequence string. As used herein, the term is used broadly and can have a variety of applications. For example, as is well known in the art, a DNA molecule can encode an RNA molecule (e.g., by the process of transcription incorporating a DNA-dependent RNA polymerase enzyme). Also, an RNA molecule can encode a peptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

As used herein, the term "isolated" means that the material is removed from its original environment, e.g., the natural environment if it is naturally occurring. For example, a naturally occurring polynucleotide or polypeptide present in a living organism is not isolated, but the same polynucleotide or polypeptide separated from some or all of the coexisting materials in the natural system is isolated. Such polynucleotides could be part of a vector and/or such polynucleotides could be part of a composition and remain isolated in that such vector or composition is not part of its natural environment.

Unless otherwise expressly stated, the term "purified" and the like does not necessarily require absolute purity has been achieved; rather, it is intended as a relative definition that relates to enrichment of a molecule or compound relative to other components normally associated with the molecule or compound in a native environment.

"Plasmids" are designated herein by a lower-case p preceded or followed by capital letters and/or numbers. The starting plasmids described in the present disclosure are commercially available, publicly available on an unrestricted basis, or can be constructed from available plasmids in accordance with published procedures. Additionally, equivalent plasmids to those described herein are known in the art and will be apparent to one of ordinary skill in the art. For example, while pET21 is used in the examples set forth below, it will be appreciated that any suitable plasmid or other expression vector now-known or hereinafter discovered may be utilized to achieve like results (for example, and without limitation, pETM6, pBAD24, etc.).

As used herein, the phrase "a functional equivalent" of a sequence means a nucleic acid or amino acid sequence that has greater than 40% homology with the nucleic acid or amino acid sequences (respectively) referenced and that has essentially the same properties, structure, and/or functionality. Accordingly, with respect to nucleic acid sequences, "functional equivalents" may include codon variants that ultimately produce the same protein. A number of studies have demonstrated that the functional equivalents of nucleic acid sequences can be prepared by maintaining the base pairing of most of the double helical regions even when changes are made to the stems. Changes in the stem sequence does not significantly affect secondary structure and/or the functionality of the underlying structure; therefore, 100% sequence identity is not required in all cases to achieve the desired structure and functionality of the resulting molecule. Similarly, in proteins, amino acid exchange can occur while still preserving protein function, for example if the modifications occur in specific regions within a protein that are not important for its function and/or if positional homology is preserved. Here, preferably, functional equivalents include those sequences having an identity of at least 70%, 75%, 80%, 90%, 97%, 98%, 99% or more and maintains the structure and functionality of the original. Of course, "functional equivalents" also encompasses fragments, in particular individual domains or sequence motifs, of the proteins and polypeptides of the present disclosure which have the desired biological activity such as, for example and without limitation, self-assembly.

As used here, the phrase "a structure having substantially defined geometry" means a structure the approximate size and shape of which is consistent when it is formed from the same components under the same conditions.

Further, in the context of the present disclosure, a "nanoparticle" is considered to be a particle having at least one dimension less than about 150 nm. For example, a Barley stripe mosaic viron nanoparticle may have a diameter at or about 18 nm, but a length of about 100-150 nm. In certain embodiments, the nanoparticle can be less than 100 nm in every dimension.

The term "virus particle" as used herein means any non-enveloped virus particle (VP) whether or not infectious, including virus-like particles that lack nucleic acid content. Exemplary embodiments of suitable VPs in the present disclosure include non-enveloped viruses having a capsid coat (for example, and without limitation, a rod-shaped (helical) capsid). Exemplary examples of rod-shaped viruses include the Barley stripe mosaic virus (BSMV).

As used herein, the terms "virus-like particles" and "VLPs" refer to molecules that closely resemble viruses yet are non-infectious because they contain no viral genetic material as mentioned above. As described below, VLPs can also be used as a nanotemplates, whether they are naturally occurring or synthesized through the individual expression of viral structural proteins, which can then self-assemble into the virus-like structure. Combinations of structural capsid proteins from different viruses can be used to create recombinant VLPs and/or proteins, nucleic acids, or small molecules may be attached to the VLP surface.

Metals suitable for use in any process according to the present disclosure include certain salts of metals as well. Particular examples of suitable metals include silver, gold, iron, copper, indium, platinum, palladium, rhodium, manganese, zinc, cobalt, Au/Pd alloy, and the like. Optionally, the metal salts can be salts of silver, gold, iron, copper, indium, platinum, palladium, rhodium, manganese, zinc, cobalt, Au/Pd alloy and the like.

The present disclosure provides novel nanoparticles and methods for synthesizing the same using VLPs in a microbial expression system. In at least one embodiment, Barley stripe mosaic virus (BSMV) coat proteins or capsids (BSMV-CP) are fused to an OAS, optionally via a linker region, and the transcript is inserted into a plasmid or other expression vector/modality that is then transformed into or otherwise expressed in a host bacterial cell. The transformed cells propagate, which produces the rod-shaped BSMV-VLPs of interest that self-assemble due to the presence of the OAS. Following isolation and purification steps, these bacterial produced BSMV-VLPs may then be employed as biotemplates in the synthesis of nanomaterials (e.g., palladium nanomaterials via hydrothermal methods). To date, only in planta production methods for BSMV have been achieved; the present disclosure is the first instance successfully engineering BSMV-CP for production in a microbial expression system which allows for engineering heretofore not possible in-planta due to the evolutionary pressures and constraints of such platforms.

In alternative embodiments, instead of (or in addition to) fusing an OAS with the BSMV-CP to initiate self-assembly, the sequence of the BSMV-CP is engineered to optimize the strength of interaction between capsid protein subunits thereon, which notably has been determined to drive spontaneous self-assembly of BSMV-VLPs when fabricated in a microbial-based expression system. The bacteria assembled BSMV-VLPs have since been successfully used as biotemplates to synthesize organic-inorganic nanomaterials of high quality in the absence of external reducing agents.

Accordingly, the inventive methods disclosed herein produce non-infectious BSMV VLPs using a bacterial protein expression system without the restrictions of conventional BSMV in planta production. These methods and templates are highly biodiverse and amendable to genetic engineering. Indeed, the BSMV-based biotemplates provide a wide range of chemical interactions afforded by its numerous multifunctional protein surfaces. The presence of various functionalities on a single template allow for the formation of a wide range of inorganic nanoparticles therefrom. Additionally, BSMV in particular allows for a vast array of genetic modifications through which enhanced properties can be imparted to the resulting nanoparticles (e.g., accelerated deposition rates) and opens the door to unique nanosynthesis opportunities. Likewise, the use of the microbial production platform in the biotemplate synthesis methods disclosed herein enables protein engineering that is simply not possible in planta due to the evolutionary pressures.

Still further, the biotemplates of the present disclosure (whether BSMV-based or otherwise) exhibit an increased stability over a wider range of conditions than can be achieved using conventionally templates. This is beneficial for numerous applications, particularly in the production of metal and/or metalized nanoparticles and allows for the deposition of new metals with their own distinct properties. Especially when considered with BSMV's enhanced ability to accommodate more metal coating than other viral platforms, this is commercially significant. (As described below, BSMV can adsorb more than twice the amount of metal relative to the current plant viral standard (TMV), which can lead to thicker coatings.) Further, through the incorporation of customizable linkers into the BSMV-CP transcript, the present methods allow for the lengths of the BSMV-derived VLPs to be specifically tailored pursuant to preference or application.

The present disclosure provides an easy and cost-effective solution for biotemplate and high-yield nanoparticle production. When the benefits of the presently disclosed approaches are taken together, it is clear the novel nanoparticles, platforms and methods disclosed herein are a significant advancement in the field.

BSMV has recently been proposed as an attractive template for nanomaterial direct synthesis as it shows at least two-fold higher nanoparticle adsorption capability than that of the popular TMV. BSMV virons are rigid rods consisting of a tripartite positive sense ssRNA genome surrounded by virus coat or capsid proteins (CPs) of 23 kDa. The particles (virons) are about 20.8 nm to about 21.4 nm in outer diameter, with an inner central channel of about 4 nm, and between about 110-150 nm long (although particles are known to align end-to-end to produce much longer rods). The BSMV CP tertiary structure, which is shown in subpart (a) of FIG. 1, is similar to that of TMV CP in that both have the presence and positioning of major alpha helices and conservation of key amino acid residues. The N- and C-terminals of the BSMV capsid protein 102 (SEQ ID NO: 1) are labeled as N and C, respectively in subpart (a) of FIG. 1. BSMV CPs 102 assemble around an interacting RNA 101 to form a viron (or particle) that retains a structural integrity relevant for infectivity up to about 65° C. after about 10 min. Consequently, BSMV can potentially be applied to surface biomineralization, while retaining its mechanical robustness, as has been observed on TMV. FIG. 1 also shows a side view of an assembled BSMV viron in subpart (b), with six turns around the RNA 101 visible, and a top-down view of a single turn of assembled BSMV capsid proteins (without RNA 101) in subpart (c). Green tubes 120 indicate Alpha helices with N-C terminal direction. Blue wires 122 are protein side chains and the red and blue regions 124 indicated in subpart (c) of FIG. 1 represent local positively and negatively charged regions of the capsid protein, which are notably on the outside or inner hollow of the virus. The structure shown in FIG. 1 was obtained by cryo-EM and visualized by pymol and NGL viewer, a web-based molecular graphics for large complexes.

BSMV offers alternative biotemplating due to its unique physiochemical properties (e.g., isoelectric point) and other active surface functionalities, which allow for different chemical interactions as compared to TMV. For example, the BSMV-CP 102 consists of two additional long insertions on the outer surface when compared to the TMV-CP. One of these insertions is a sequence of 10 amino acids (residues 1-10), located at the exposed N-terminus, while the other (residues 84-94) is an insertion loop that also protrudes from the outer surface. This second region (residues 84-94) in particular, provides significant opportunity for genetic modifications to incorporate desired properties such as, by way of a non-limiting example, accelerated deposition rate.

Recently, the investigators' studies demonstrated successful synthesis of palladium nanorods by using in planta produced BSMV as an alternate template to TMV (FIG. 1). The synthesized nanorods were of similar, if not higher, quality than those produced with TMV and BSMV was shown to adsorb at least twice as much metal as TMV, thus leading to thicker coatings and unique nanosynthesis opportunities.

However, conventional approaches to produce BSMV are limited to in-planta production, which necessarily limits the ability to genetically engineer and mass produce the virus. First, as noted above, the genomes of inplanta-synthesized viruses, and BSMV in particular, are associated with mutations and recombination during viral replication due to evolutionary pressures that may remove any desired engineered modification in the interest of viral fitness. Second, conventional BSMV in planta production utilizes infectious plant pathogens that leverage the viral replication cycle in plants, which requires an extended period of time before a relatively small quantity of viruses can be extracted.

Unlike conventional in planta methods, the production methods of the present disclosure use microbial expression platforms for nanoparticle production, which are fast, simple and result in high yields. VLP self-assembly of wild type virus coat protein is initiated by the OAS. However, the OAS of BSMV is unknown. Accordingly, heretofore, BSMV-VLPs have not been produced in bacteria due to their inability to self-assemble from wild-type BSMV. The novel methods provided herein provide self-assembly functionality to BSMV-VLPs, thereby allowing for the beneficial use of microbial expression platforms in this context. Furthermore, these methods uniquely offer the ability to tune the length of the VLPs as desired or needed for a particular application.

Figure 2A:
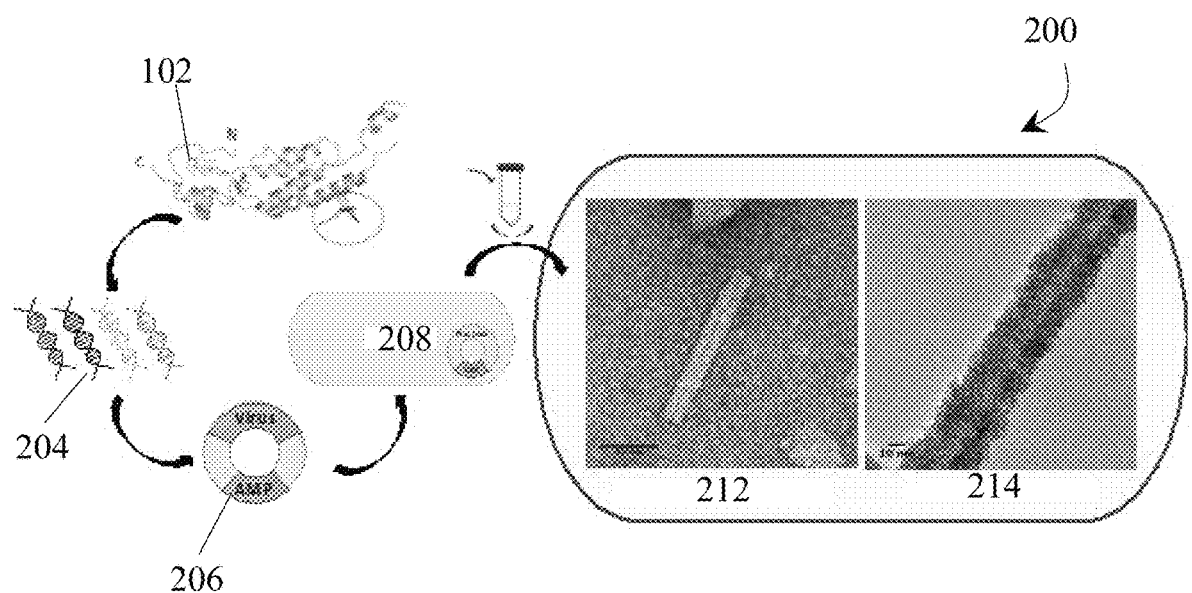
FIGS. 2A and 2B show representations of an exemplary method for producing BSMV-VLPs in a bacterial expression system according to at least one embodiment of the present disclosure, with FIG. 2A showing a schematic of the method and FIG. 2B showing a flow-chart representative of the method.
Figure 2B:
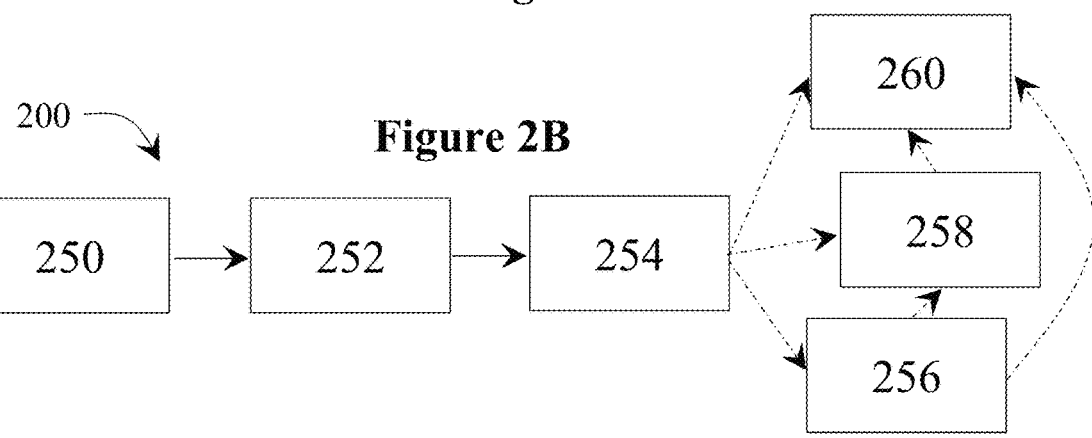

Now referring to FIGS. 2A and 2B, at least one embodiment of a novel method 200 for producing BSMV-VLPs in a microbial expression system is shown. This method 200 will be first be explained in general terms to aid in understanding, followed by a more detailed descriptions of various aspects and using specific examples. Notably, method 200 is the first method that allows for the length of BSMV-derived VLPs to be specifically tailored as desired, thereby allowing for the ability to produce biotemplates with a customized morphology for use as a biotemplate to synthesis organic-inorganic nanomaterials.

Generally, in at least one embodiment, the method 200 comprises the steps of constructing a plasmid or expression vector comprising a fusion of a viral CP and an OAS 302 (step 250), transforming such plasmid or expression vector into a host and expressing the same using an expression system 208 (step 252), and isolating the resulting VLPs 212 from the expression system (step 254).

Method 200 may optionally further include the step of nanoparticle synthesis (step 260) using the VLPs 212 produced at step 254 and, where desired, one or more interim steps such as coating at least a surface of the resulting VLPs 212 with a metal using adsorption or the like (step 256) and/or performing microbial reduction of the VLPs (step 258) prior to nanoparticle synthesis (step 260).

In at least one embodiment, the expression system 208 is heterologous and may comprise an *Escherichia coli* (*E. coli*) platform. While *E. coli* is the host platform described herein, it will be appreciated that any number of expression systems may be utilized in the present method 200 including, without limitation, *S. cerevisiae* or those non-bacterial expression systems that utilize insect cells and/or mammalian cells. Furthermore, DNA of the novel CP-OAS disclosed herein may be integrated into a genome for expression.

Additionally or alternatively, the viral CP/interaction domain may be a BSMV-CP 102 or any other virus strain from which a suitable CP can be produced and assembled into a VLP 212 using the method without the presence of a naturally occurring OAS therein. In at least one embodiment of the present disclosure, the viral CP/interaction domain may be of any viral strain that does not include a native OAS such as, for example, other rigid, rod-shaped viruses in the *Hordeivirus* genus or those in the *Furovirus, Pecluvirus, Pomovirus, Tobamovirus,* or *Tobravirus* geneses in the family of Virgaviridae.

Figure 3:
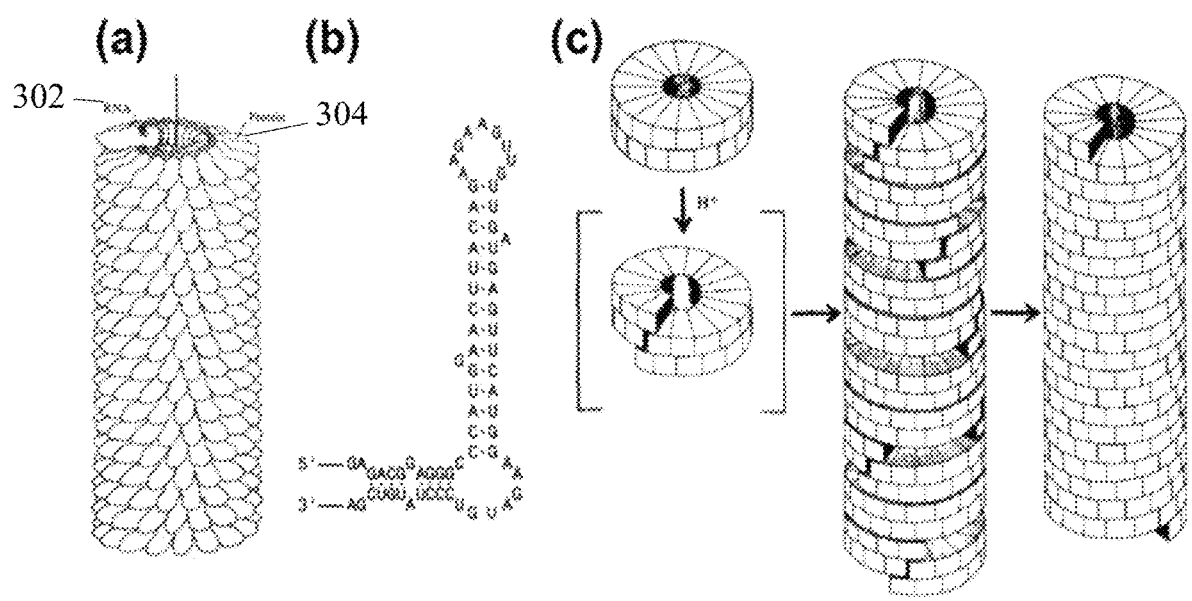
FIG. 3 shows a schematic interpretation of a TMV coat protein and origin of assembly (OAS) on TMV RNA, with subpart (a) showing a completed self-assembly into a helical structure; subpart (b) showing a partial nucleotide sequence of SEQ ID No. 11 and secondary structure of the OAS on TMV RNA; and subpart (c) showing a schematic interpretation of the structures of a TMV coat protein and OAS and its steps of self-assembly.

As previously noted, one of the hurdles to using BSMV is that native BSMV coat protein transcripts lack the ability to self-assemble into VLPs (i.e. initiate the assembly from disk to rod structure). As shown in FIG. 3, CP units in certain viruses (like TMV) spontaneously form a disk structure (represented in subparts (a) and (c) of FIG. 3) by the binding of an OAS 302 into the central hole of a two-ring subassembly of the capsid protein 304. More specifically, the interactions of secondary-structured OAS with CP units drive the spontaneous nucleation of disk subassembly, with these "disks" forming in long aggregates that are made up of discrete short helices (corresponding in size to the number of subunits in the disk). This consequently leads to self-assembly of disk structures into a helical rod-shaped particle, with the disks initially stacked in imperfect register, but annealing over time into a helical rod-shaped particle (see subpart (c) of FIG. 3).

Figure 4:
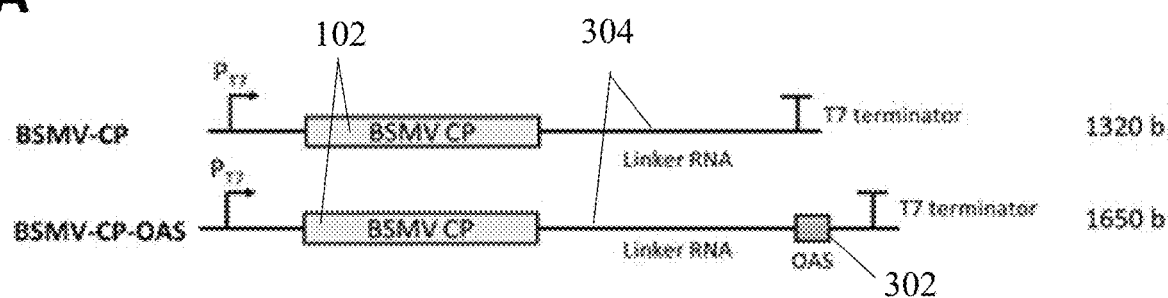
FIG. 4 represents BSMV-viral capsid protein (BSMV-CP) constructs that include a linker RNA, with subpart (A) showing a BSMV-CP fused to an artificial linker with 1322 base transcript length and no OAS (top) and a BSMV-CP fused with an artificial linker and an OAS sequence from TMV, with 1652 base transcript length, subpart (B) showing a visualization of a BSMV-CP-linker by transmission electronic microscope (TEM), and subpart (C) showing a visualization of BSMV-CP-linker-OAS and resulting self-assembly by TEM.
Figure 4:
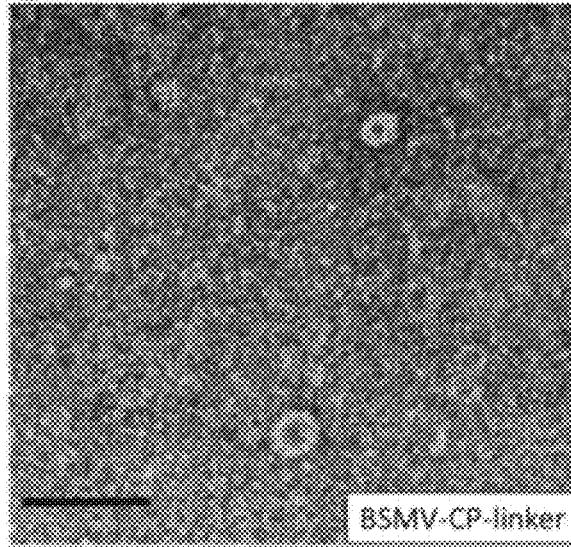
Figure 4:
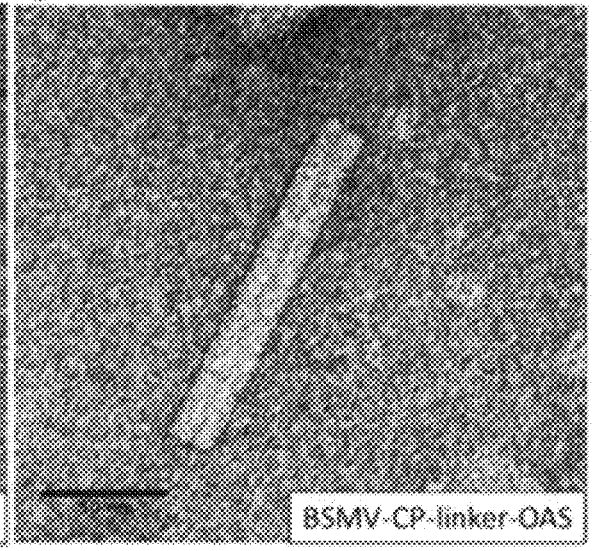

When a BSMV-CP transcript is expressed alone there is no assembly. To address the inability of native BSMV to self-assemble, at step 250, a plasmid or other expression vector is constructed comprising a fusion of an interaction domain such as a viral CP (e.g., BSMV-CP 102, as shown in FIG. 2A) and an OAS 302 (SEQ ID NO: 26). The OAS 302 sequence may be operatively linked to the BSMV-CP sequence such that a resulting product is a BSMV-CP operatively linked with an OAS 302; indeed, in at least one exemplary embodiment, the OAS 302 is introduced downstream into the protein transcript as shown in FIG. 4, subpart A.

The operative linkage between the interaction domain and the OAS 302 may be direct fusion or via a linker 304 (described in further detail below). In at least one exemplary embodiment, BSMV-CP is prepared with an OAS 302 from TMV at the 3' end derived from SEQ ID NO: 11. It has been determined that the inclusion of OAS 302 in the construct initiates self-assembly via the RNA/CP interaction with the BSMV-CP. Further, the plasmid and/or expression vector may be optimized for bacterial expression pursuant to protocols known in the art.

Figure 5:
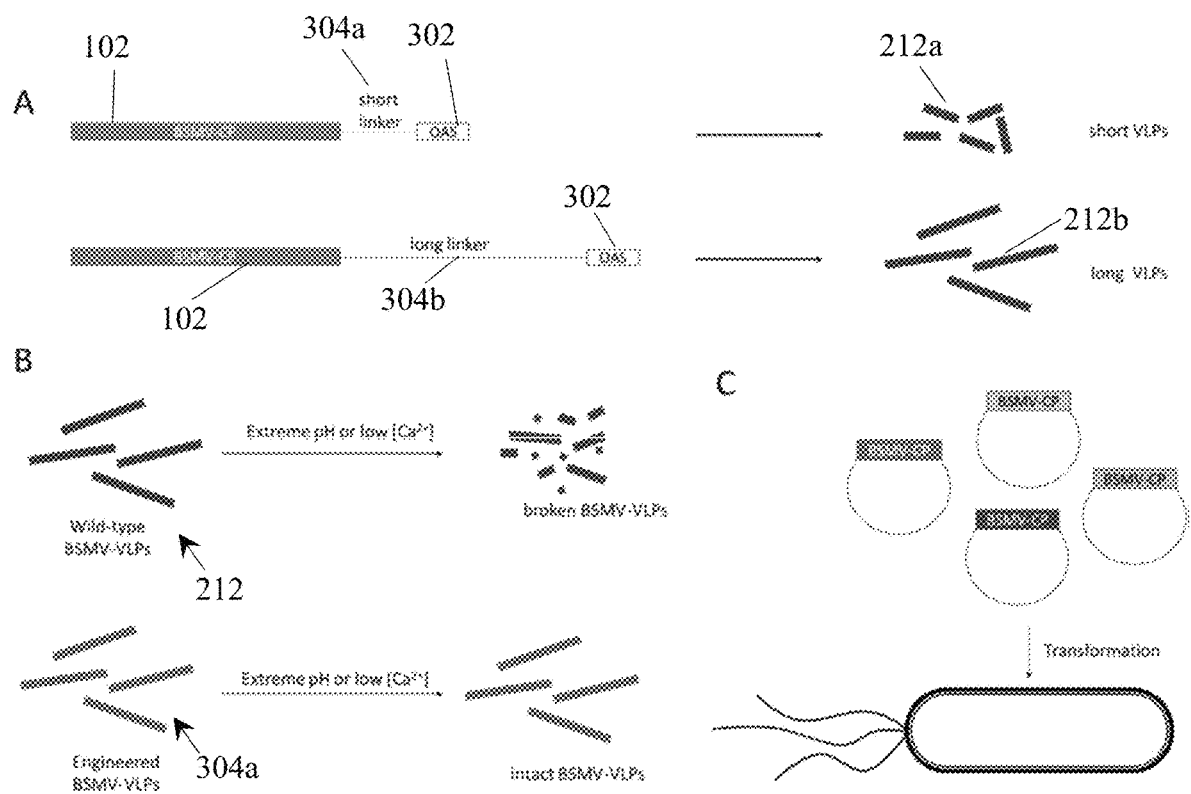
FIG. 5, subpart (a) shows a schematic representation of tunable BSMV-VLPs-BSMV coat protein fused to a customizable length of linker and an OAS.

Now referring to FIG. 5, as noted above, the interaction domain (e.g., BSMV-CP 102) may be linked to the OAS 302 via a linker region 304 according to protocols known in the art such as, and without limitation, construction techniques such as DNA synthesis or gene splicing by overlap extension PCR (for example, the linker 304 may comprise a fusion protein). Linker regions 304 may be selected from any number of peptide sequences, nucleic acid sequences, or other suitable materials. In at least one exemplary embodiment, the linker region 304 has a nucleic acid sequence of SEQ ID NO: 13. The length of a linker region 304 will depend on several factors, including the geometry of the self-assembly units and the desired morphology of the resulting VLPs. It is generally desirable to provide a linker region 304 of sufficient length to allow the interaction domain operatively connected to the self-assembly unit to orient towards its target, thus permitting sufficient binding. In at least one embodiment, the length of a linker region 304 may be selected to allow for maximum target accessibility to the binding sites of the interaction domain. It may further be desirable in certain applications to select linkers for resistance to proteases (e.g., where in vivo applications are contemplated). In at least one exemplary embodiment, the linker region 304 is positioned downstream of the CP, after a stop codon and before the OAS 302 as shown in FIG. 5, subpart A.

In some instances, it may be desirable to use linkers 304 between about 600 and about 700 nucleic acids in length and in other instances the use of linkers 304 between about 2,200 and about 2,300 nucleic acids in length may be desirable. In at least two exemplary embodiments, the linker region 304 may be 661 or 2,243 nucleic acids in length. It will be appreciated that these linker lengths are provided solely by way of example and in no way limiting; the linker region 304 may comprise any length suitable or desired for a particular application.

Linkers 304 may also be used to join a marker (e.g., such as a fluorescently labeled moiety or compound) or a destructive material (e.g., a radioactive material of sufficient activity) to a self-assembly unit. In at least one embodiment, the linker 304 may be secured to the opposite terminus of the self-assembly unit from the interaction domain.

Incorporation of a linker region 304 imparts the ability to tune and/or modify the length of the resulting noninfectious VLP 212 and, thus, any nanoparticle subsequently synthesized therewith. Indeed, it has been determined that length of the overall construct directly correlates to the length of any resulting VLP 212 produced at step 252.

Subpart A of FIG. 5 illustrates this concept. Use of a linker 304a having a first, shorter sequence (for example, and without limitation, a 100 amino acid linker), results in VLPs 212a having a corresponding first, shorter length, whereas use of a second, longer linker 304b sequence (for example, and without limitation, a 1322 amino acid linker) results in VLPs 212b having a corresponding second, longer length. This property can be exploited by strategically choosing the linker length to tune the morphology of the VLPs 212 produced.

It should also be noted that any desired engineering to BSMV may be performed at or prior to step 250 to take advantage of the transformation and expression step 252. For example, because surface residues of BSMV can be modified, in at least one embodiment, BSMV-VLPs can be conjugated with antigen display for medical applications. There, the resulting BSMV-VLPs would function as a vaccine scaffold to elicit a desired immune response following administration to a subject, such as, for example, the L2 protein fragment from the papillomavirus does when conjugated with TMV.

At step 252, the constructs are transformed into a host expression system (such as a microbial-based expression system comprising *E. coli*, for example) and grown such that the construct is expressed and VLPs 212 are produced. SEQ ID NO. 26 provides a nucleic acid sequence of one such *E. coli* plasmid carrying a BSMV-CP 102 fused with a linker region 304 and an OAS 302. In at least one embodiment, the *E. coli* transformed with the plasmids or expression vectors were grown at room temperature for 16-20 hours. FIG. 4, subparts B and C shows images taken using a 200 kV Tecnai T20 transmission electron microscope (TEM) of lysed BSMV-CP-linkers at step 254, both with (subpart C) and without (subpart B) an OAS 302 fused therewith. As is clearly seen in subpart B of FIG. 4, the BSMV-CP-linker without an OAS 302 failed to self-assemble during step 252 (only disks structure formed without OAS 302), whereas the image of the BSMV-CP-linker fused with an OAS 302 indicates the presence of self-assembled, rod-shaped BSMV VLPs indicating that self-assembly did in fact occur at step 252. Accordingly, at step 250, a TMV-OAS 302 is fused to the BSMV-CP 102 transcript using methods known in the art, which imparts self-assembly characteristics into the BSMV-VLPs 212 thereafter produced at step 252 through the expression system 208.

Unlike bacteriophage systems such as M13 that infect the bacterial platform and limit options for property customizations, plant viruses can be expressed heterologously without affecting the producing bacteria. In other words, because VLP production is independent of a virus's ability to infect or alter microbial function, the heterologous expression system 208 utilized at step 252 allows for more opportunities to engineer VLP properties without compromising properties and quality in *E. coli* bacteria by infection. Further, because a heterologous host is employed, the evolutionary pressures on virus replication are reduced as compared to in planta models, which further promotes the capability to genetically engineer the VLP structures. Accordingly, by employing the powerful and unique abilities of synthetic biology, method 200 utilizes a heterologous expression system such as an *E. coli* platform to produce VLPs with genetic modifications that plant hosts are not able to achieve.

At step 254, the resulting VLPs 212 are isolated from *E. coli* and purified pursuant to protocols known in the art. The VLPs 212 may be used as biotemplates for the synthesis of nanoparticles at step 260 pursuant to known methods. In the embodiment utilizing BSMV-VLPs 212 as described herein, nanosynthesis results in the production of high quality nanorods having size and dimensions that correlate with those of the VLPs 212. Where a linker region 304 was employed in the construct at step 250, the custom VLPs 212 will have a size and dimension that directly correlates with the length of the customized linker region 304.

Optionally, prior to step 256, the VLPs 212 may be coated with metal at step 256. Metal coated biotemplates have numerous commercial uses. For example, as a component in batteries such as electrodes, chemical sensors, and memory devices, as well as catalysts. It has been determined that metal-coated TMV increases the charge capacity of an anode ten-fold via increasing the surface area thereof. Because wild-type BSMV has more than two-fold metal coating ability as compared to TMV, BSMV-VLPs have the potential to further boost the capacity of batteries over conventionally attainable standards.

Alternative embodiments of method 200 may utilize BSMV-CP transcripts that do not necessarily contain the OAS 302 at all (native or engineered). Instead, in such embodiments, the transcripts are engineered at step 250 with one or more specific point-mutations in the BSMV-CP to optimize the strength of interaction between the CP subunits thereof to result in a more stable biotemplate/VLP.

Figure 6:
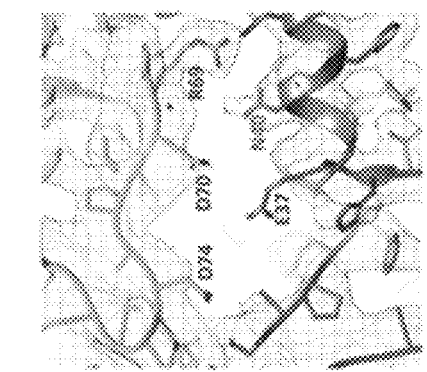
FIG. 6 illustrates various graphical models of interacting residues between BSMV coat protein subunits, with subpart (a) showing that the interacting residues of TMV (PDB: 2xea) are D77 and E50 residues of the coat protein subunit; subpart (b) showing likely interacting residues of BSMV (PDB:5a7a) corresponding to that of TMV, which includes E62, D68, D70, and D101 based on the present investigators' data; and subpart (c) showing predicted native interacting residues of BSMV in the literature, which includes E37, D70, and D74.
Figure 6:
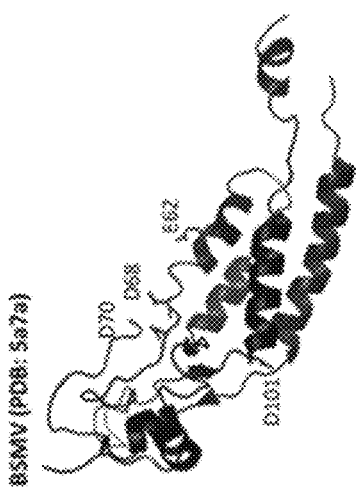
Figure 6:
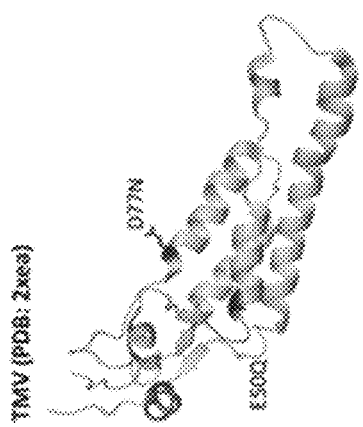

To stabilize these interactions, one or more individual point-mutations may be made in the BSMV-CP using site-directed mutagenesis or the like to neutralize or change the targeted residue to the opposite charge to strengthen the interaction between subunits (see subpart C of FIG. 5) pursuant to methods known in the art. Based on crystal structures, the present investigators have identified E37Q, E37R, E62Q, D68N, D70N, and D101N on the BSMV-CP as probable sites that, if mutated as described, enhance the stability of BSMV. FIG. 6, subparts A-G illustrate the interacting residues that are identified targets for site mutations of the TMV-CP subunit (subpart A), those of the BSMV-CP subunit that correspond to the TMV targets (subpart B), and those of BSMV-CP previously identified in the literature. These sites contain charged residues that may be neutralized, for example, by calcium ions to facilitate neutral assembly/disassembly of the virus during infection. By mutating these residues, the interaction therebetween can be strengthened to achieve self-assembly without an OAS 302. Mutations of D101N (SEQ ID NO: 5), E62Q (SEQ ID NO: 9), both D101N and E62Q (SEQ ID NO: 10), D101R (SEQ ID NO: 6), and D101K (SEQ ID NO: 4) in particular have been tested and validated as increasing stability in this manner and allowing for engineered self-assembly pursuant to the methods and systems described herein without an OAS 302 (see FIG. 7).

Figure 7:
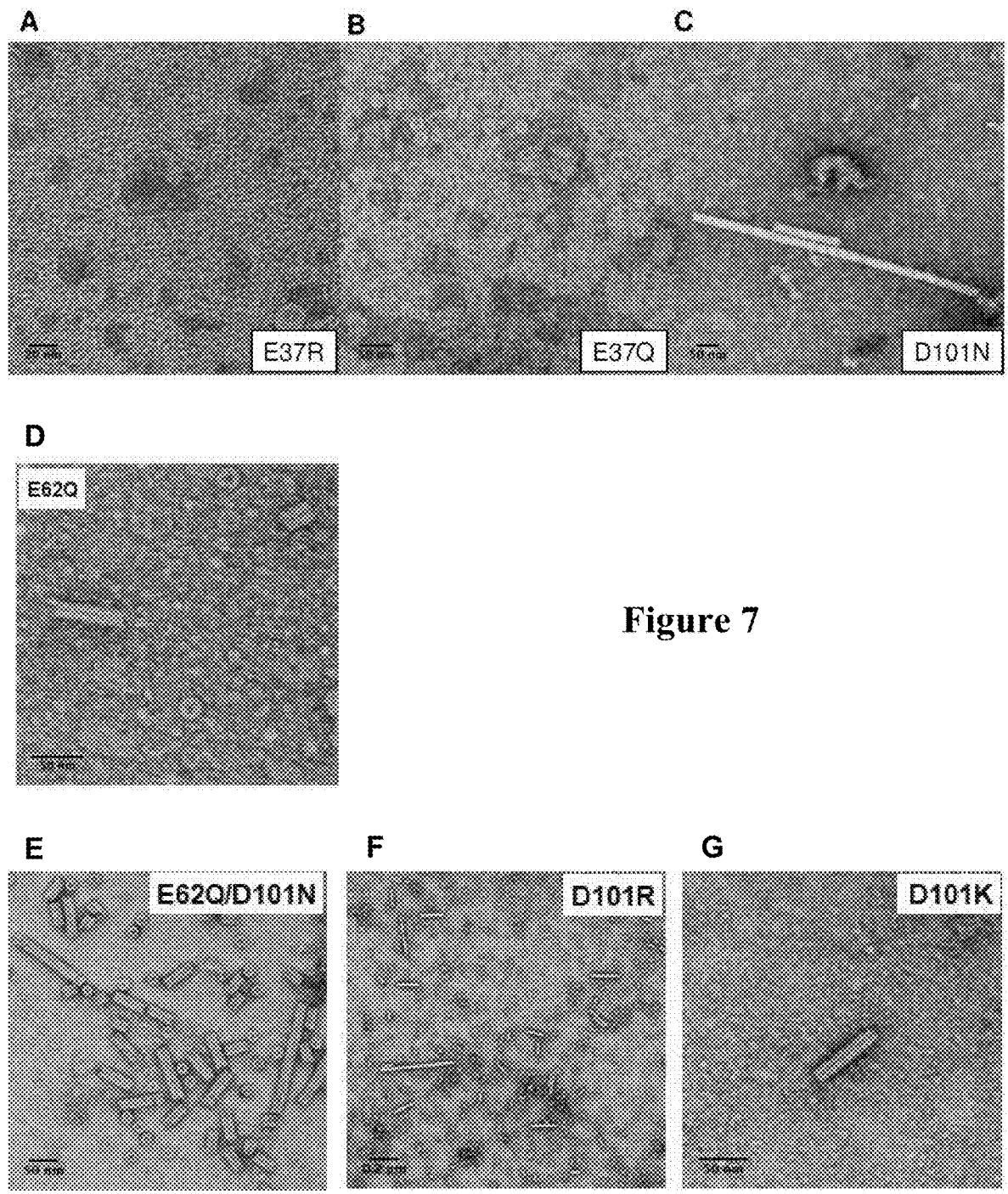
FIG. 7 shows TEM visualization of BSMV-CP-linker carrying a point mutation at E37R (subpart A), a point mutation at E37Q (subpart B), a point mutation D101N (subpart C), a point mutation at E62Q (subpart D), point mutations at both E62Q and D101N (subpart E), a point mutation at D101R (subpart F), and a point mutation at D101K (subpart G), with the self-assembly of rod-shaped VLPs being verified at least in the D101N, E62Q, E62Q/D101N, D101R, and D101K point mutations.

Further, and importantly, it has been determined that site specific mutations also support the RNA-free (i.e. no OAS) self-assembly of VLPs. FIG. 7 shows a TEM visualization of BSMV-CP fused to an artificial linker carrying a E37R mutation (subpart A; SEQ ID NO: 8), a E37Q mutation (subpart B; SEQ ID NO: 7), a D101N mutation (subpart C; SEQ ID NO: 5), a E62Q mutation (subpart D; SEQ ID NO: 9), both a D101N mutation and a E62Q mutation (SEQ ID NO: 10), a D101R mutation (SEQ ID NO: 6), and a D101K mutation (SEQ ID NO: 4), with the formation of self-assembled nanorods being verified and clearly visible (see subparts C-G of FIG. 7). It should be noted that the linker region 304 is the residual sequence and, without fusion of an OAS, native BSMV-CP does not form VLPs without one or more of the point mutations described herein. Accordingly, the modified mutants exhibited stronger protein-protein interactions as compared to wild-type that stabilized the VLPs and led to self-assembly.

It will be noted that while such BSMV-CP engineering techniques may be used to achieve self-assembly of VLPs 212 without the use of OAS 302 in the construct, it may also be desirable to employ such techniques where an OAS 302 is utilized due to the metal coating benefits associated with such engineering. Indeed, success rates for coating VLPs with metal is largely dependent on environmental parameters such as pH and the presence of cations. These factors can potentially destabilize the template and prevent self-assembly due to the carboxylate interactions between CPs and, thus, lead to random aggregate formation and low yields (see subpart B of FIG. 5). Strengthening the interaction of CP subunits in the interaction domain using the platforms and methods described herein render the resulting VLPs less susceptible to extremes in pH and calcium concentration and allow for effective metal coating under wider processing conditions than as seen with conventional approaches. Thus, the present platforms and methods provide avenues through which BSMV's superior metal coating ability can be leveraged. Furthermore, the VLPs of the present disclosure that are synthesized pursuant to the methods described herein exhibit enhanced stability as compared to conventional biotemplates thus allowing for the synthesis of more homogenous nanoparticles than has been heretofore achieved.

Materials And Methods

Cloning of BSMV-CP Expression Plasmid

A codon-optimized DNA sequence encoding BSMV-CP, a linker region, and an OAS (BSMV-CP-linker-OAS; SEQ ID NO: 15) was ordered from IDT (Coralville, IA) and cloned to pET21-1cys-tmv-cp vector (provided by Professor Culver, University of Maryland, College Park), the original plasmid for which was pET-21a(+), with NdeI and XhoI, generating pET21-BSMV-CP-linker-OAS (SEQ ID NO: 26). pET21-BSMV-CP-linker-OAS was subsequently digested with SalI and XhoI to remove the OAS, blunt-ended with Klenow fragment (NEB, Ipswich, MA Cat. No.: M0210S), ligated back to the backbone itself, generating pET21-BSMV-CP-linker. All strains and plasmids used are listed in Table 1.

TABLE 1

Strains and plasmids

| Name | Relevant genotype | Vector backbone | Plasmid origin | Source |
|---|---|---|---|---|
| Strains | | | | |
| BL21-CodonPlus(DE3)-RIPL strain | E. coli B F− ompT hsdS(rB− mB−) dcm+ Tetr gal λ(DE3) endA Hte [argU proL Camr] [argU ileY leuW Strep/Spec resistant | | | Agilent Technologies |
| Plasmids | | | | |
| pET21-BSMV-CP-linker | bla | pET21-1cys-tmv-cp (original backbone: pET-21a(+))[41] | pBR322 | This study |

Further, for making mutants (E37Q, E37R, E62Q, D68N, D70N, and D101N) to have increased stability, pET21-BSMV-CP-linker-OAS was used as a template for site-directed mutagenesis (E37Q-SEQ ID NO: 20, E37R-SEQ ID NO: 21, E62Q-SEQ ID NO: 23, D68N-SEQ ID NO: 17, D70N-SEQ ID NO: 16, and D101N-SEQ ID NO: 22). All plasmids in the pET-21 vector are ampicillin resistant, with the applicable primers listed in Table 2.

TABLE 2

Primers used for making BSMV-coat protein expression plasmid

| Primers' name | Sequence (5' > 3') | Expression plasmids |
|---|---|---|
| E37Q 5' | TGGTGGGTGCATGTAcAGGCCTGGAATAAGT | pET21-BSMV-E37Q |
| E37Q 3' | ACTTATTCCAGGCCTgTACATGCACCCACCA | |
| E37R 5' | TGGTGGGTGCATGTAcgtGCCTGGAATAAGTTT | pET21-BSMV-E37R |
| E37R 3' | AAACTTATTCCAGGCacgTACATGCACCCACCA | |
| E62Q 5' | CGCTCACAAGTAGCAcAGTATTTGGCTGCTT | pET21-BSMV-E62Q, |
| E62Q 3' | AAGCAGCCAAATACTgTGCTACTTGTGAGCG | pET21-BSMV-E62Q/D101N |
| D68N 5' | TATTTGGCTGCTTTGaATCGTGACCTTCCGG | pET21-BSMV-D68N |
| D68N 3' | CCGGAAGGTCACGATtCAAAGCAGCCAAATA | |
| D70N 5' | GCTGCTTTGGATCGTaACCTTCCGGCTGACG | pET21-BSMV-D70N |
| D70N 3' | CGTCAGCCGGAAGGTtACGATCCAAAGCAGC | |
| D101N 5' | AAATTTTTTCGTCTTaATAAACGTACAATCG | pET21-BSMV-D101N, |
| D101N 3' | CGATTGTACGTTTATtAAGACGAAAAAATTT | pET21-BSMV-E62Q/D101N |
| D101K 5' | AAATTTTTTCGTCTTaaaAAACGTACAATCGCT | pET21-BSMV-D101K |
| D101K 3' | AGCGATTGTACGTTTtttAAGACGAAAAAATTT | |
| D101R 5' | AAATTTTTTCGTCTTcgTAAACGTACAATCGC | pET21-BSMV-D101R |
| D101R 3' | GCGATTGTACGTTTAcgAAGACGAAAAAATTT | |

BSMV-CP Expression Conditions

Each BSMV-CP expression plasmid was transformed into E. coli BL21-CodonPlus (DE3), streaked on plates and incubated for 16-20 hours at 37° C. Single colonies were inoculated into Luria-Bertani (LB) broth and grown at 37° C. for 16-20 hours with shaking. The overnight liquid cultures were then diluted a hundred-fold in LB broth and grown until OD600=0.5 before induction with 0.1 mM isopropyl β-D-1-thiogalactopyranoside (IPTG) to express BSMV capsid protein. All BL21-CodonPlus (DE3) liquid cultures or plates containing ampicillin (100 μg/ml) and chloramphenicol (25 μg/ml). The culture was then incubated for 16-20 hours at room temperature (23° C.). Cultures were then centrifuged at room temperature (23° C.) for 5 minutes at 6000 rpm. The supernatant was discarded, and the cell pellet was used directly for purification or stored at −80° C. for processing later.

BSMV-VLP Purification

BSMV-VLPs were isolated from $E.$ $coli$ transformed with the described plasmids and grown at room temperature for 16-20 hrs. The cells were homogenized in 2.5 or 6 ml Bugbuster® protein isolation solution (MilliporeSigma, Burlington, MA Cat. No: 70584) for 10 min at room temperature after which 7.5 μl dithiothreitol was added to 2.5 μl of Lysonase Bioprocessing Reagent Reagent (MilliporeSigma, Burlington, MA Cat. No: 70584) was added per manufacturer's protocol. The homogenate was further incubated for 10 min, then centrifuged at 5,000×g for 10 min to remove insoluble cellular debris. The supernatant was fractionated through a linear gradient of Sucrose (MilliporeSigma, Burlington, MA Cat. No: 70584) spun at 19,000×g for 10 min and the top light-scattering band containing the VLPs was collected and further purified by centrifugation at 64,000×g at 4° C. For the sample without doing a gradient, the supernatant was further purified by centrifugation at 10,000×g for 20 min at 4° C. The final pellet was suspended in 0.01 M Tris buffer of pH 7.

TEM Imaging

In preparation for imaging, a 1.5 μl droplet of the VLP suspension was deposited onto carbon formvar copper grids and was negatively stained by a 1.5 μl droplet of phosphotungstic acid (PTA). Images were taken using a 200 kV Tecnai T20 transmission electron microscope (TEM).

Size Measurement by Dynamic Light Scattering

The refractive index of purified BSMV-VLPs was detected with 1.3351 by refractometer and the size of BSMV-VLPs was measured with dynamic light scattering by Malvern Zetasizer Nano ZS (Malvern Panalytical Ltd, United Kingdom). The refractive index and viscosity of the Tris resuspension buffer were 1.35 and $1.00037^{42}$, respectively.

Metal Coating Process

Metal coating on VLPs was performed in a 100 ml CSTR reactor vessel at a controlled temperature of 57° C. As in a typical nanoparticle synthesis, the precursor sodium tetrachloropalladate (II) ($Na_2PdCl_4$) (98%, Sigma Aldrich, St Louis, MO) aqueous solution (concentration is usually between 0.3 mM and 6 mM) was added into the vessel containing the purified VLPs after heating to the desired reaction temperature. 0.3 mL aliquots of the solution were collected regularly during the course of the reaction for ex-situ study by UV-vis characterization. The solution was immediately placed on ice to quench the reaction for the absorbance measurement by UV-Vis spectrophotometer (Varian Cary 100) at 25° C. Poly(methyl methacrylate) (PMMA) plastic cuvettes (VWR Scientific Prod Midwest, Radnor, PA) were used for the UV-vis characterization. The nanoparticles were washed repeatedly to remove residual salt and precursor solution by redispersing them in water. Thicker coatings were achieved by reincubating the washed nanorods in $Na_2PdCl_4$ solution and recoated multiple times. Millipore water was used in all experiments.

Results and Discussion

As discussed in detail herein, VLPs self-assemble to due to interactions between RNA and capsid proteins, and interactions between adjacent capsid proteins. BSMV-CP plasmids with and without TMV-OAS that were codon optimized for bacterial expression were designed pursuant to the present disclosure (shown in subpart A of FIG. 4) and, in initial experiments, expressed at 37° C. for 4 hours in $E.$ $coli$ before lysing. Crude protein lysate was centrifuged through several rounds to isolate any synthesized VLPs, which were characterized by TEM.

In this iteration, TEM images did not show any BSMV rod-shaped VLPs or disk structures (data not shown) suggesting that BSMV CPs were not produced, they failed to self-assemble, or that the isolation procedure was sufficient to capture any produced VLPs. TMV constructs were expressed and purified as positive control and subsequent electron microscopy displayed the presence of TMV VLPs excluding the possibility that the isolation procedure was insufficient. If wildtype CPs are expressed in the host, they form disk-shaped structures. The absence of BSMV disk structures suggests poor soluble CP expression, not necessarily failure to self-assemble.

Figure 8:
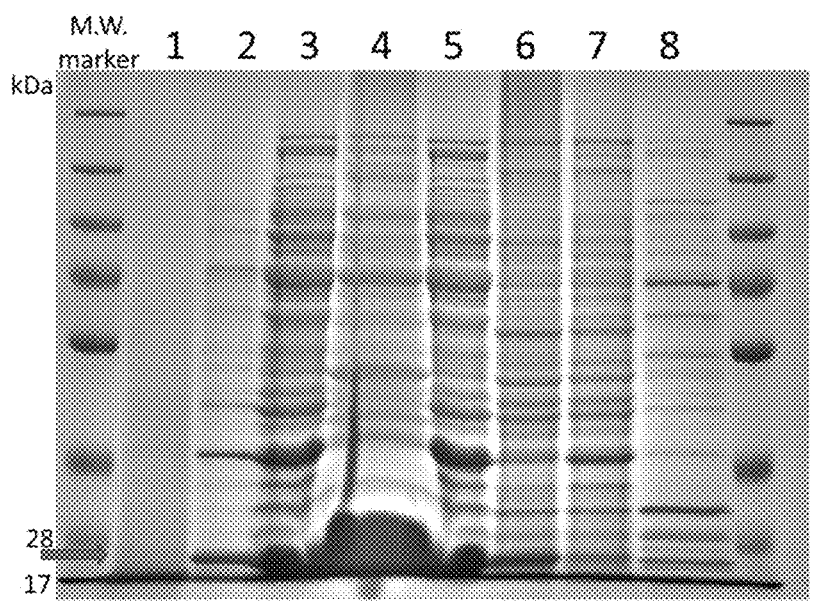
FIG. 8 shows PAGE analysis results of a BSMV-CP purification scheme, with Lane 1 indicative of whole cell lysate before IPTG induction; Lane 2 indicative of whole cell lysate after IPTG induction; Lane 3 indicative of whole cell lysate after Bugbuster; Lane 4 indicative of insoluble bacterial pellet; Lane 5 indicative of supernatant after 4.5/5 min before 50 k/30'; Lane 6 indicative of insoluble pellet after 50 k/30 min; Lane 7 indicative of pellet after insoluble pellet removed and 3 k/5 min; and Lane 8 indicative of final resuspension; BSMV-CP is ~22.5 kDa.

To examine expression, crude protein lysates from $E.$ $coli$ with induced CP plasmids were analyzed via SDS-PAGE. As shown in FIG. 8, SDS-PAGE analysis revealed a relatively heavy band of BSMV protein in the bacterial insoluble pellet suggesting that the majority of the capsid proteins were misfolded.

Because protein aggregation can occur due to the rapid expression and misfolding of proteins at high temperatures, these results support the $E.$ $coli$ host is not able to express soluble protein where the protein of interest is from a host living at 37° C. Instead, the results support that the higher temperature lead to the formation of misfolded insoluble proteins and inclusion bodies composed of insoluble protein aggregates. Given that temperature of this plant virus native host in plants is lower than 37° C. (25-28° C.), the BSMV-CP folding appears to be thermodynamically unfavorable at the higher temperature (37° C.).

Figure 9:
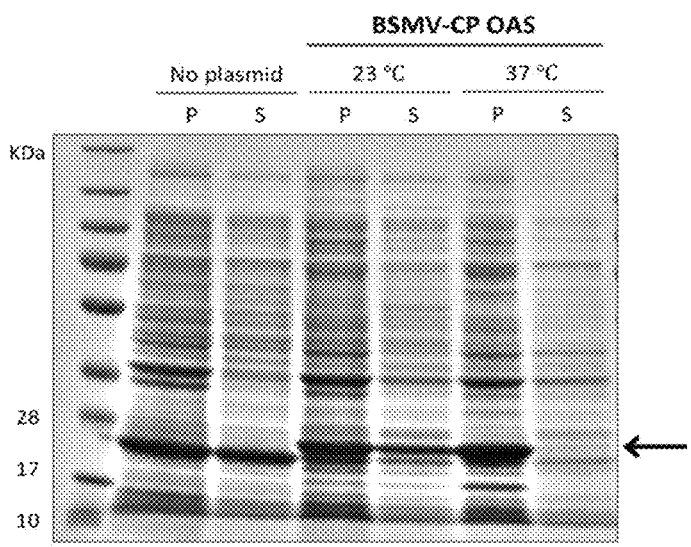
FIG. 9 shows PAGE analysis results of BSMV-CP expression conducted at 23° C. and 37° C., respectively, with P representing pellet and S representing supernatant after 92,000×g and 20 min centrifuge and arrow mark indicating BSMV-CP at ~22.5 kDa.

Accordingly, in furtherance of investigations into the occurrence of self-assembly, the expression temperature was reduced to 23° C. and the expression time extended from 4 hours to 16 hours to slow the protein expression rate and enable proper protein folding. Subsequent SDS-PAGE analysis revealed a significant increase in soluble capsid protein see FIG. 9). Subsequent isolation of potential particles and characterization, electron microscopy images demonstrated the presence of self-assembled rod-shaped BSMV VLPs assembly (see subpart C of FIG. 4). This data supports that TMV-OAS was recognized by BSMV-CP and functions to initiate the VLP self-assembly, while only disks structure formed in the BSMV-CP absent of OAS (see subpart B of FIG. 4). Furthermore, these results support that poor protein expression can be improved by adjusting the induction temperature to increase the yield of soluble proteins. Importantly, this is the first time that BSMV-VLPs have been expressed from a microbial-based protein expression system at neutral pH and observed by TEM.

Following the favorable results indicating VLP self-assembly in *E. coli*, studies were conducted to optimize the expression and purification process. Different concentrations of IPTG inducer from 0.10 mM, 0.075 mM, 0.050 mM to 0.010 mM were tested with respect to induction of expression of BSMV-CPs. There, the expression levels of BSMV-CPs in the soluble fraction was monitored by SDS-PAGE. As shown in subpart (a) of FIG. 10, the results support that 0.075 and 0.1 mM IPTG concentrations produced higher yield of soluble CP as compared to the lower concentrations tested. The effect of the addition of resuspension buffer in solubilizing a final pellet was also determined to enhance the yield of soluble fraction. Sodium phosphate buffer is usually used in protein solubilization but it caused precipitate over time. Water and tris(hydroxymethyl)aminomethane (Tris-HCl) were then tested as final resuspension buffers. Subpart (b) of FIG. 10 supports that both water and Tris buffer prevent precipitation of VLPs. Furthermore, the results support that Tris buffer was superior as it generally stabilized more BSMV protein and gave rise to less cellular proteins.

Figures 10, 11:
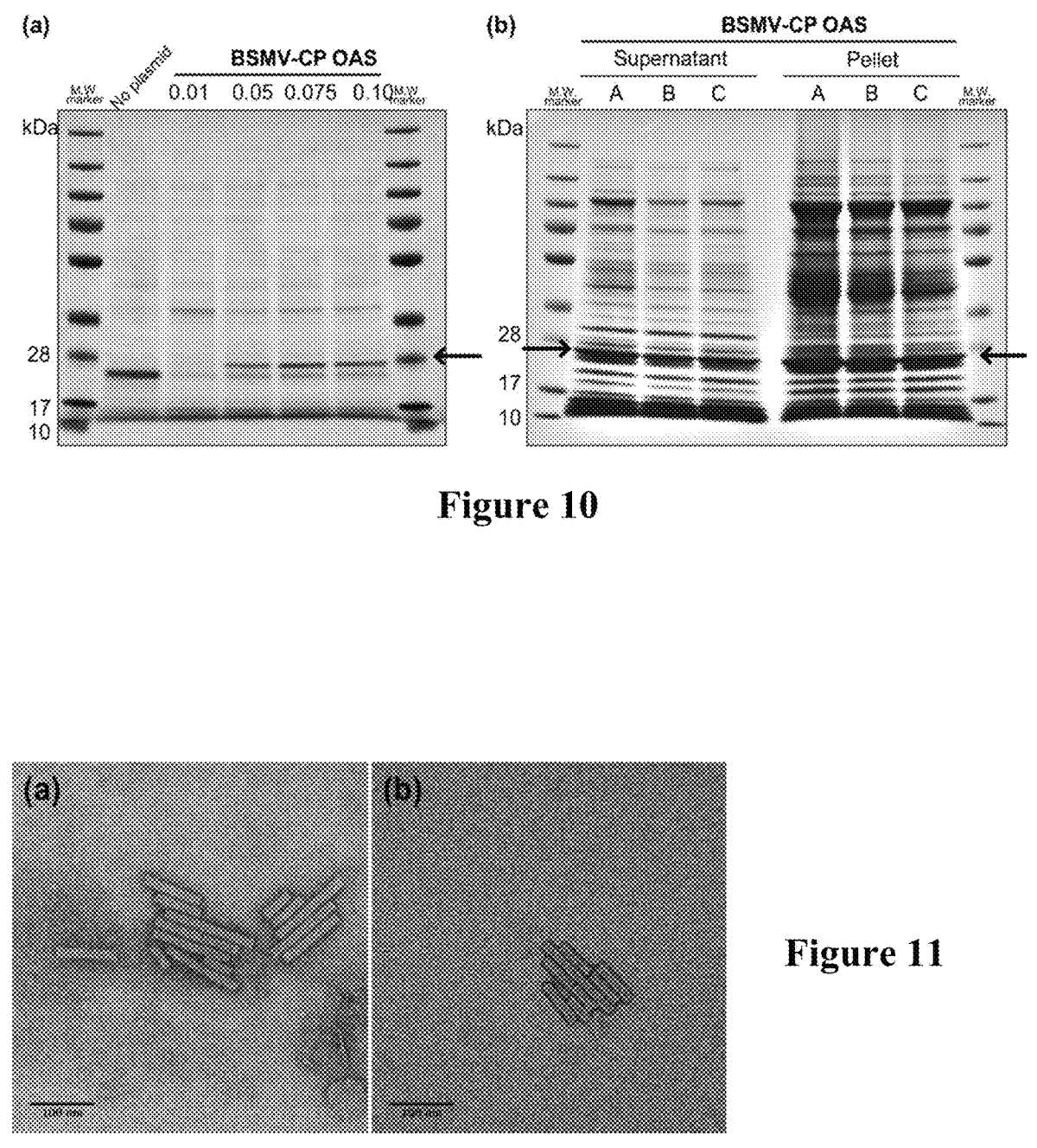
Figure 12:
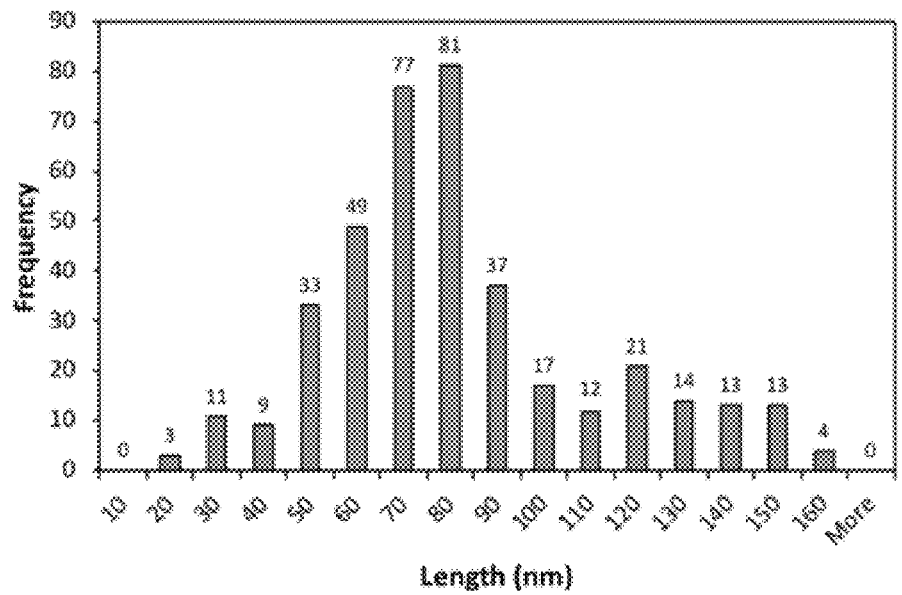
FIG. 12 is a length distribution histogram of purified BSMV-VLPs produced according to at least one embodiment of the present disclosure.

Based on the optimization parameters identified, the cells were further purified with sucrose cushion centrifugation (a technique utilized for purification without resulting in a firm pellet). As shown in FIG. 11, electron microscopy displayed the presence of BSMV-VLPs in both top and bottom layers of the sucrose cushion with no significant differences in length or size. The purified BSMV-VLPs yielded variable structure between 20-160 nm length. The majority of the expressed nanotubes were found to be between 70 nm to 90 nm long. (see FIG. 12).

Alternative size characterization studies were also performed, with the produced VLPs subjected to dynamic light scattering (DLS). DLS revealed a bimodal distribution with peaks at 476.5 nm (92.3%) (which corresponds with self-assembled VLPs) and incomplete disks at 37.99 nm (7.7%) (see Table 3). Accordingly, the majority of assembled CPs formed complete VLPs that were variable in length. As hydrodynamic radii are inherently larger than the actual size detected by TEM, DLS provides an alternative way to rapidly check the VLPs quality rather than an absolute metric of size.

TABLE 3

Hydrodynamic radii obtained by dynamic light scattering (DLS).

| Size (spherical diameter) | Intensity | Standard deviation (diameter) | Coefficient of variation |
| --- | --- | --- | --- |
| 476.5 nm | 92.3% | 157.7 nm | 33.10% |
| 37.99 nm | 7.7% | 6.412 nm | 16.88% |

While spherical diameter is listed in Table 3, it should be noted that the measuring instrument views each rod-shaped VLP as a spherical due to the multiple perspective angles from which measurements are taken. While the VLPs are rod-shaped instead of spherical, the resulting diameter information correlates with the accurate VLP diameter obtained from the TEM.

Figure 13:
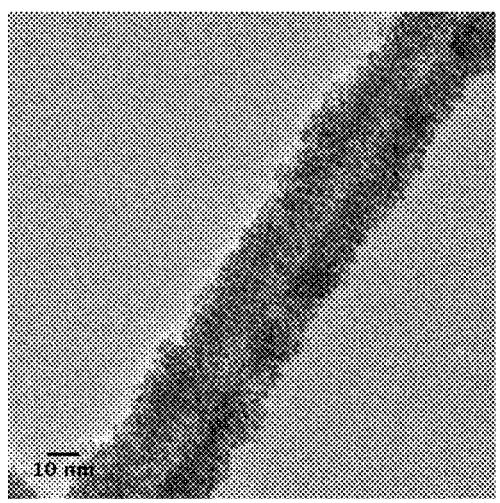
FIG. 13 is a TEM image of a palladium coated BMSV-VLP nanorod prepared according to at least one embodiment of the present disclosure.

To examine the capability as biotemplates of the bacteria assembled BSMV-VLPs, the VLPs were coated with palladium via hydrothermal synthesis in the absence of extra reducing agent and incubated in a reaction vessel with $Na_2PdCl_4$ precursor solution. FIG. 13 supports that the BSMV-VLPs were fully coated with a uniform layer of palladium nanoparticles. Accordingly, not only were the BSMV-VLPs able to drive surface-mediated mineralization with palladium, but also retained their robust stability during biomineralization reaction.

Accordingly, the novel methods disclosed herein provide for the in vivo production of BSMV-VLPs from an expression system that is not plant based. As the microbial-based system in particular offers the capabilities of genetic engineering and rapid protein expression, the present systems and methods allows for the rapid design-build-test cycle for desired characteristics of BSMV-VLPs development. Methods for optimizing protein expression and purification are also provided in connection with such novel systems and methods, for example by adjusting expression temperature and bioprocessing reagent in purification, which results in increased efficiency with respect to cell lysis and higher yield of soluble fraction. The methods hereof are sufficient to produce BSMV-VLPs on a large scale and viable to express, purify and isolate engineered VLPs with similar structural features and, thus, promote the efficiency, quality, and cost-effectiveness of bottom-up nanomaterial synthesis.

While various embodiments of nanoparticles, systems, and methods hereof have been described in considerable detail, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or to limiting. The scope of the disclosure is to he defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that this description and the appended claims will encompass, all modifications and changes apparent to those of ordinary skill in the art based on this disclosure.

The invention claimed is:

1. A method of manufacturing a nanoparticle biotemplate comprising the steps of:
introducing into an isolated host a nucleic acid sequence comprising SEQ ID NO: 1 or a functional equivalent thereof that encodes a Barley stripe mosaic virus coat protein (BSMV-CP), and one or both of:
(a) an origin of self-assembly (OAS) of a Tobacco mosaic virus operatively linked with the BSMV-CP wherein a portion of the nucleic acid sequence that encodes the OAS comprises SEQ ID NO: 11 or a functional equivalent thereof, and
(b) at least one site-directed mutation on the BSMV-CP that facilitates self-assembly of a BSMV viral-like particle by at least replacing a repulsive interaction between at least-two wild-type BSMV-CP subunits with a neutral or attractive interaction between the correlative at least two BSMV-CP subunits of the encoded BSMV-CP,
wherein the at least one site-directed mutation on the BSMV-CP is:
at residue E37Q and comprises SEQ ID NO: 7,
at residue E37R and comprises SEQ ID NO: 8,
at residue E62Q and comprises SEQ ID NO: 9,
at residue D68N and comprises SEQ ID NO: 2,
at residue D70N and comprises SEQ ID NO: 3,
at residue D101N and comprises SEQ ID NO: 5,
at residue D101R and comprises SEQ ID NO: 6,
at residue D101K and comprises SEQ ID NO: 4, or
a combination of site mutations comprising two or more of the foregoing;
expressing the nucleic acid sequence in a microbial expression system to produce self-assembled BSMV viral-like particles (BSMV VLPs); and
isolating the BSMV VLPs from the microbial expression system.

2. The method of claim 1, wherein the step of expressing the nucleic acid sequence further comprises:
constructing a plasmid or an expression vector comprising the nucleic acid sequence; and
transforming the plasmid or expression vector into the host;
wherein the host is *Escherichia coli* and the step of expressing the nucleic acid sequence is performed at a neutral pH.

3. The method of claim 2, wherein the BSMV-CP comprises the BSMV-CP fused with a linker region and the at least one site-directed mutation on the BSMV-CP.

4. The method of claim 1, wherein the nucleic acid sequence encodes the BSMV-CP fused with a linker region and the OAS.

5. The method of claim 4, further comprising the step of selecting a length of the linker region based on a desired length in the resulting BSMV VLPs.

6. The method of claim 1, further comprising the step of synthesizing one or more nanoparticles using the resulting VLPs.

7. The method of claim 6, further comprising the step of coating at least a surface of the resulting VLPs with a metal.

8. The method of claim 7, wherein the step of coating is performed using adsorption.

9. The method of claim 7, further comprising the step of performing microbial reduction of the coating of at least the surface of the resulting VLPs.

10. The method of claim 1, wherein expressing the nucleic acid sequence in a microbial expression system to allow expression of the BSMV-CP and produce self-assembled BSMV VLPs comprises incubation of an inoculated liquid culture at 23° C. for 16 to 20 hours.

* * * * *

SEQUENCE LISTING

<160> NUMBER OF SEQ ID NOS: 26

<210> SEQ ID NO 1
<211> LENGTH: 198
<212> TYPE: PRT
<213> ORGANISM: Barley stripe mosaic virus

```
<400> SEQUENCE: 1

Met Pro Asn Val Ser Leu Thr Ala Lys Gly Gly His Tyr Ile Glu
1               5                  10                  15

Asp Gln Trp Asp Thr Gln Val Val Glu Ala Gly Val Phe Asp Asp Trp
            20                  25                  30

Trp Val His Val Glu Ala Trp Asn Lys Phe Leu Asp Asn Leu Arg Gly
                35                  40                  45

Ile Asn Phe Ser Val Ala Ser Ser Arg Ser Gln Val Ala Glu Tyr Leu
    50                  55                  60

Ala Ala Leu Asp Arg Asp Leu Pro Ala Asp Val Asp Arg Arg Phe Ala
65                  70                  75                  80

Gly Ala Arg Gly Gln Ile Gly Ser Pro Asn Tyr Leu Pro Ala Pro Lys
                85                  90                  95

Phe Phe Arg Leu Asp Lys Arg Thr Ile Ala Glu Leu Thr Arg Leu Ser
                100                 105                 110

Arg Leu Thr Asp Gln Pro His Asn Asn Arg Asp Ile Glu Leu Asn Arg
                115                 120                 125

Ala Lys Arg Ala Thr Thr Asn Pro Ser Pro Ala Gln Ala Pro Ser
130                 135                 140

Glu Asn Leu Thr Leu Arg Asp Val Gln Pro Leu Lys Asp Ser Ala Leu
145                 150                 155                 160

His Tyr Gln Tyr Val Leu Ile Asp Leu Gln Ser Ala Arg Leu Pro Val
                165                 170                 175

Tyr Thr Arg Lys Thr Phe Glu Arg Glu Leu Ala Leu Glu Trp Ile Ile
                180                 185                 190

Pro Asp Ala Glu Glu Ala
                195

<210> SEQ ID NO 2
<211> LENGTH: 198
<212> TYPE: PRT
<213> ORGANISM: Barley stripe mosaic virus

<400> SEQUENCE: 2

Met Pro Asn Val Ser Leu Thr Ala Lys Gly Gly His Tyr Ile Glu
1               5                  10                  15

Asp Gln Trp Asp Thr Gln Val Val Glu Ala Gly Val Phe Asp Asp Trp
            20                  25                  30

Trp Val His Val Glu Ala Trp Asn Lys Phe Leu Asp Asn Leu Arg Gly
                35                  40                  45

Ile Asn Phe Ser Val Ala Ser Ser Arg Ser Gln Val Ala Glu Tyr Leu
    50                  55                  60

Ala Ala Leu Asn Arg Asp Leu Pro Ala Asp Val Asp Arg Arg Phe Ala
65                  70                  75                  80

Gly Ala Arg Gly Gln Ile Gly Ser Pro Asn Tyr Leu Pro Ala Pro Lys
                85                  90                  95

Phe Phe Arg Leu Asp Lys Arg Thr Ile Ala Glu Leu Thr Arg Leu Ser
                100                 105                 110

Arg Leu Thr Asp Gln Pro His Asn Asn Arg Asp Ile Glu Leu Asn Arg
                115                 120                 125

Ala Lys Arg Ala Thr Thr Asn Pro Ser Pro Ala Gln Ala Pro Ser
130                 135                 140

Glu Asn Leu Thr Leu Arg Asp Val Gln Pro Leu Lys Asp Ser Ala Leu
145                 150                 155                 160
```

His Tyr Gln Tyr Val Leu Ile Asp Leu Gln Ser Ala Arg Leu Pro Val
            165                 170                 175

Tyr Thr Arg Lys Thr Phe Glu Arg Glu Leu Ala Leu Glu Trp Ile Ile
            180                 185                 190

Pro Asp Ala Glu Glu Ala
            195

<210> SEQ ID NO 3
<211> LENGTH: 198
<212> TYPE: PRT
<213> ORGANISM: Barley stripe mosaic virus

<400> SEQUENCE: 3

Met Pro Asn Val Ser Leu Thr Ala Lys Gly Gly Gly His Tyr

```
Gly Ala Arg Gly Gln Ile Gly Ser Pro Asn Tyr Leu Pro Ala Pro Lys
                85                  90                  95

Phe Phe Arg Leu Lys Lys Arg Thr Ile Ala Glu Leu Thr Arg Leu Ser
            100                 105                 110

Arg Leu Thr Asp Gln Pro His Asn Asn Arg Asp Ile Glu Leu Asn Arg
        115                 120                 125

Ala Lys Arg Ala Thr Thr Asn Pro Ser Pro Pro Ala Gln Ala Pro Ser
130                 135                 140

Glu Asn Leu Thr Leu Arg Asp Val Gln Pro Leu Lys Asp Ser Ala Leu
145                 150                 155                 160

His Tyr Gln Tyr Val Leu Ile Asp Leu Gln Ser Ala Arg Leu Pro Val
                165                 170                 175

Tyr Thr Arg Lys Thr Phe Glu Arg Glu Leu Ala Leu Glu Trp Ile Ile
            180                 185                 190

Pro Asp Ala Glu Glu Ala
        195

<210> SEQ ID NO 5
<211> LENGTH: 198
<212> TYPE: PRT
<213> ORGANISM: Barley stripe mosaic virus

<400> SEQUENCE: 5

Met Pro Asn Val Ser Leu Thr Ala Lys Gly Gly His Tyr Ile Glu
1               5                   10                  15

Asp Gln Trp Asp Thr Gln Val Val Glu Ala Gly Val Phe Asp Asp Trp
                20                  25                  30

Trp Val His Val Glu Ala Trp Asn Lys Phe Leu Asp Asn Leu Arg Gly
            35                  40                  45

Ile Asn Phe Ser Val Ala Ser Ser Arg Ser Gln Val Ala Glu Tyr Leu
        50                  55                  60

Ala Ala Leu Asp Arg Asp Leu Pro Ala Asp Val Asp Arg Arg Phe Ala
65                  70                  75                  80

Gly Ala Arg Gly Gln Ile Gly Ser Pro Asn Tyr Leu Pro Ala Pro Lys
                85                  90                  95

Phe Phe Arg Leu Asn Lys Arg Thr Ile Ala Glu Leu Thr Arg Leu Ser
            100                 105                 110

Arg Leu Thr Asp Gln Pro His Asn Asn Arg Asp Ile Glu Leu Asn Arg
        115                 120                 125

Ala Lys Arg Ala Thr Thr Asn Pro Ser Pro Pro Ala Gln Ala Pro Ser
130                 135                 140

Glu Asn Leu Thr Leu Arg Asp Val Gln Pro Leu Lys Asp Ser Ala Leu
145                 150                 155                 160

His Tyr Gln Tyr Val Leu Ile Asp Leu Gln Ser Ala Arg Leu Pro Val
                165                 170                 175

Tyr Thr Arg Lys Thr Phe Glu Arg Glu Leu Ala Leu Glu Trp Ile Ile
            180                 185                 190

Pro Asp Ala Glu Glu Ala
        195

<210> SEQ ID NO 6
<211> LENGTH: 198
<212> TYPE: PRT
<213> ORGANISM: Barley stripe mosaic virus

<400> SEQUENCE: 6
```

Met Pro Asn Val Ser Leu Thr Ala Lys Gly Gly His Tyr Ile Glu
1               5                   10                  15

Asp Gln Trp Asp Thr Gln Val Val Glu Ala Gly Val Phe Asp Asp Trp
            20                  25                  30

Trp Val His Val Glu Ala Trp Asn Lys Phe Leu Asp Asn Leu Arg Gly
            35                  40                  45

Ile Asn Phe Ser Val Ala Ser Ser Arg Ser Gln Val Ala Glu Tyr Leu
    50                  55                  60

Ala Ala Leu Asp Arg Asp Leu Pro Ala Asp Val Asp Arg Arg Phe Ala
65                  70                  75                  80

Gly Ala Arg Gly Gln Ile Gly Ser Pro Asn Tyr Leu Pro Ala Pro Lys
                85                  90                  95

Phe Phe Arg Leu Arg Lys Arg Thr Ile Ala Glu Leu Thr Arg Leu Ser
                100                 105                 110

Arg Leu Thr Asp Gln Pro His Asn Asn Arg Asp Ile Glu Leu Asn Arg
            115                 120                 125

Ala Lys Arg Ala Thr Thr Asn Pro Ser Pro Ala Gln Ala Pro Ser
130                 135                 140

Glu Asn Leu Thr Leu Arg Asp Val Gln Pro Leu Lys Asp Ser Ala Leu
145                 150                 155                 160

His Tyr Gln Tyr Val Leu Ile Asp Leu Gln Ser Ala Arg Leu Pro Val
                165                 170                 175

Tyr Thr Arg Lys Thr Phe Glu Arg Glu Leu Ala Leu Glu Trp Ile Ile
                180                 185                 190

Pro Asp Ala Glu Glu Ala
            195

<210> SEQ ID NO 7
<211> LENGTH: 198
<212> TYPE: PRT
<213> ORGANISM: Barley stripe mosaic virus

<400> SEQUENCE: 7

Met Pro Asn Val Ser Leu Thr Ala Lys Gly Gly His Tyr Ile Glu
1               5                   10                  15

Asp Gln Trp Asp Thr Gln Val Val Glu Ala Gly Val Phe Asp Asp Trp
            20                  25                  30

Trp Val His Val Gln Ala Trp Asn Lys Phe Leu Asp Asn Leu Arg Gly
            35                  40                  45

Ile Asn Phe Ser Val Ala Ser Ser Arg Ser Gln Val Ala Glu Tyr Leu
    50                  55                  60

Ala Ala Leu Asp Arg Asp Leu Pro Ala Asp Val Asp Arg Arg Phe Ala
65                  70                  75                  80

Gly Ala Arg Gly Gln Ile Gly Ser Pro Asn Tyr Leu Pro Ala Pro Lys
                85                  90                  95

Phe Phe Arg Leu Asp Lys Arg Thr Ile Ala Glu Leu Thr Arg Leu Ser
                100                 105                 110

Arg Leu Thr Asp Gln Pro His Asn Asn Arg Asp Ile Glu Leu Asn Arg
            115                 120                 125

Ala Lys Arg Ala Thr Thr Asn Pro Ser Pro Ala Gln Ala Pro Ser
130                 135                 140

Glu Asn Leu Thr Leu Arg Asp Val Gln Pro Leu Lys Asp Ser Ala Leu
145                 150                 155                 160

His Tyr Gln Tyr Val Leu Ile Asp Leu Gln Ser Ala Arg Leu Pro Val
                165                 170                 175

Tyr Thr Arg Lys Thr Phe Glu Arg Glu Leu Ala Leu Glu Trp Ile Ile
            180                 185                 190

Pro Asp Ala Glu Glu Ala
        195

<210> SEQ ID NO 8
<211> LENGTH: 198
<212> TYPE: PRT
<213> ORGANISM: Barley stripe mosaic virus

<400> SEQUENCE: 8

Met Pro Asn Val Ser Leu Thr Ala Lys Gly Gly Gly His Tyr Ile Glu
1               5                   10                  15

Asp Gln Trp Asp Thr Gln Val Val Glu Ala Gly Val Phe Asp Asp Trp
            20                  25                  30

Trp Val His Val Arg Ala Trp Asn Lys Phe Leu Asp Asn Leu Arg Gly
        35                  40                  45

Ile Asn Phe Ser Val Ala Ser Ser Arg Ser Gln Val Ala Glu Tyr Leu
    50                  55                  60

Ala Ala Leu Asp Arg Asp Leu Pro Ala Asp Val Asp Arg Arg Phe Ala
65                  70                  75                  80

Gly Ala Arg Gly Gln Ile Gly Ser Pro Asn Tyr Leu Pro Ala Pro Lys
                85                  90                  95

Phe Phe Arg Leu Asp Lys Arg Thr Ile Ala Glu Leu Thr Arg Leu Ser
            100                 105                 110

Arg Leu Thr Asp Gln Pro His Asn Asn Arg Asp Ile Glu Leu Asn Arg
        115                 120                 125

Ala Lys Arg Ala Thr Thr Asn Pro Ser Pro Ala Gln Ala Pro Ser
    130                 135                 140

Glu Asn Leu Thr Leu Arg Asp Val Gln Pro Leu Lys Asp Ser Ala Leu
145                 150                 155                 160

His Tyr Gln Tyr Val Leu Ile Asp Leu Gln Ser Ala Arg Leu Pro Val
                165                 170                 175

Tyr Thr Arg Lys Thr Phe Glu Arg Glu Leu Ala Leu Glu Trp Ile Ile
            180                 185                 190

Pro Asp Ala Glu Glu Ala
        195

<210> SEQ ID NO 9
<211> LENGTH: 198
<212> TYPE: PRT
<213> ORGANISM: Barley stripe mosaic virus

<400> SEQUENCE: 9

Met Pro Asn Val Ser Leu Thr Ala Lys Gly Gly Gly His Tyr Ile Glu
1               5                   10                  15

Asp Gln Trp Asp Thr Gln Val Val Glu Ala Gly Val Phe Asp Asp Trp
            20                  25                  30

Trp Val His Val Glu Ala Trp Asn Lys Phe Leu Asp Asn Leu Arg Gly
        35                  40                  45

Ile Asn Phe Ser Val Ala Ser Ser Arg Ser Gln Val Ala Gln Tyr Leu
    50                  55                  60

Ala Ala Leu Asp Arg Asp Leu Pro Ala Asp Val Asp Arg Arg Phe Ala
65                  70                  75                  80

Gly Ala Arg Gly Gln Ile Gly Ser Pro Asn Tyr Leu Pro Ala Pro Lys
                85                  90                  95

```
Phe Phe Arg Leu Asp Lys Arg Thr Ile Ala Glu Leu Thr Arg Leu Ser
            100                 105                 110

Arg Leu Thr Asp Gln Pro His Asn Asn Arg Asp Ile Glu Leu Asn Arg
        115                 120                 125

Ala Lys Arg Ala Thr Thr Asn Pro Ser Pro Ala Gln Ala Pro Ser
130                 135                 140

Glu Asn Leu Thr Leu Arg Asp Val Gln Pro Lys Asp Ser Ala Leu
145                 150                 155                 160

His Tyr Gln Tyr Val Leu Ile Asp Leu Gln Ser Ala Arg Leu Pro Val
                165                 170                 175

Tyr Thr Arg Lys Thr Phe Glu Arg Glu Leu Ala Leu Glu Trp Ile Ile
            180                 185                 190

Pro Asp Ala Glu Glu Ala
        195

<210> SEQ ID NO 10
<211> LENGTH: 198
<212> TYPE: PRT
<213> ORGANISM: Barley stripe mosaic virus

<400> SEQUENCE: 10

Met P

```
acggagggcc catggaactt acagaagaag tcgttgatga gttcatggaa gatgtcccta    120
tgtcgatcag gcttgcaaag tttcgatctc gaaccggaaa aaagagtgat gtccgcaaag    180
ggaaaaata                                                             189

<210> SEQ ID NO 12
<211> LENGTH: 597
<212> TYPE: DNA
<213> ORGANISM: Barley stripe mosaic virus

<400> SEQUENCE: 12
atgcccaacg tatcactgac agcgaaaggg ggaggtcatt acatcgaaga tcagtgggat     60
acgcaagtcg tcgaagcagg agtgttcgac gactggtggg tgcatgtaga ggcctggaat    120
aagtttcttg acaatctgcg cggcatcaat ttttccgtcg ccagcagtcg ctcacaagta    180
gcagagtatt tggctgcttt ggatcgtgac cttccggctg acgttgatcg tcgtttcgcg    240
ggtgcacgtg gtcaaatcgg cagccccaat tacttaccag cacctaaatt ttttcgtctt    300
gataaacgta caatcgctga attgacacgt ttgtcgcgct tgacggatca gccccacaac    360
aatcgtgata tcgagttaaa tcgcgcaaaa cgcgcaacaa caaatcctag cccacctgct    420
caagccccga gcgaaaacct tacactgcgc gacgtgcaac ccttaaagga ctccgcgtta    480
cattatcagt atgtccttat tgatcttcag tccgcacgct tgcctgtgta tacccgcaag    540
actttcgagc gcgagctggc tctggagtgg atcattccag atgcagagga agcataa       597

<210> SEQ ID NO 13
<211> LENGTH: 661
<212> TYPE: DNA
<213> ORGANISM: Artificial Sequence
<220> FEATURE:
<223> OTHER INFORMATION: Linker region

<400> SEQUENCE: 13
accggtttta aatatgtctt acagtatcac tactccatct cagttcgtgt tcttgtcatc     60
agcgtgggcc gacccaatag agttaattaa tttatgtact aatgccttag gaaatcagtt    120
tcaaacacaa caagctcgaa ctgtcgttca aagacaattc agtgaggtgt ggaaaccttc    180
accacaagta actgttaggt tccctgacag tgactttaag gtgtacaggt acaatgcggt    240 attgacccg ctagtcacag cactgttagg tgcattcgac actagaaata gaataataga    300
agttgaaaat caggcgaacc ccacgactgc cgaaacgtta gatgctactc gtagagtaga    360
cgacgcaacg gtggccataa ggagcgcgat aaataattta atagtagaat tgatcagagg    420
aaccggatct tataatcgga gctctttcga gagctcttct ggtttggttt ggacctctgg    480
tcctgcaact tgatagtccg gacctgcagg acgcgtgtcg acgtttgaga gagaagatta    540
caaacgtgag agacggaggg cccatggaac ttacagaaga agtcgttgat gagttcatgg    600
aagatgtccc tatgtcgatc aggcttgcaa agtttcgatc tcgaaccggc ctaggctcgt    660
g                                                                    661

<210> SEQ ID NO 14
<211> LENGTH: 786
<212> TYPE: DNA
<213> ORGANISM: Artificial Sequence
<220> FEATURE:
<223> OTHER INFORMATION: Fusion of barley stripe mosiac virus capsid
      protein and origin of assembly from tobacco mosaic virus

<400> SEQUENCE: 14
```

-continued

```
atgcccaacg tatcactgac agcgaaaggg ggaggtcatt acatcgaaga tcagtgggat      60
acgcaagtcg tcgaagcagg agtgttcgac gactggtggg tgcatgtaga ggcctggaat     120
aagtttcttg acaatctgcg cggcatcaat ttttccgtcg ccagcagtcg ctcacaagta     180
gcagagtatt tggctgcttt ggatcgtgac cttccggctg acgttgatcg tcgtttcgcg     240
ggtgcacgtg gtcaaatcgg cagccccaat tacttaccag cacctaaatt ttttcgtctt     300
gataaacgta caatcgctga attgacacgt tgtcgcgct tgacggatca gccccacaac      360
aatcgtgata tcgagttaaa tcgcgcaaaa cgcgcaacaa caaatcctag cccacctgct     420
caagccccga gcgaaaacct acactgcgc gacgtgcaac ccttaaagga ctccgcgtta      480
cattatcagt atgtccttat tgatcttcag tccgcacgct tgcctgtgta tacccgcaag     540
actttcgagc gcgagctggc tctggagtgg atcattccag atgcagagga agcataagta     600
ttgtttatag aaataatata aaattaggtt tgagagagaa gattacaaac gtgagagacg     660
gagggcccat ggaacttaca gaagaagtcg ttgatgagtt catggaagat gtccctatgt     720
cgatcaggct tgcaaagttt cgatctcgaa ccggaaaaaa gagtgatgtc cgcaaaggga     780
aaaata                                                                786
```

<210> SEQ ID NO 15
<211> LENGTH: 1447
<212> TYPE: DNA
<213> ORGANISM: Artificial Sequence
<220> FEATURE:
<223> OTHER INFORMATION: Fusion of BSMV-CP with a linker and a tobacco mosaic virus OAS

<400> SEQUENCE: 15

```
atgcccaacg tatcactgac agcgaaaggg ggaggtcatt acatcgaaga tcagtgggat      60
acgcaagtcg tcgaagcagg agtgttcgac gactggtggg tgcatgtaga ggcctggaat     120
aagtttcttg acaatctgcg cggcatcaat ttttccgtcg ccagcagtcg ctcacaagta     180
gcagagtatt tggctgcttt ggatcgtgac cttccggctg acgttgatcg tcgtttcgcg     240
ggtgcacgtg gtcaaatcgg cagccccaat tacttaccag cacctaaatt ttttcgtctt     300
gataaacgta caatcgctga attgacacgt tgtcgcgct tgacggatca gccccacaac      360
aatcgtgata tcgagttaaa tcgcgcaaaa cgcgcaacaa caaatcctag cccacctgct     420
caagccccga gcgaaaacct acactgcgc gacgtgcaac ccttaaagga ctccgcgtta      480
cattatcagt atgtccttat tgatcttcag tccgcacgct tgcctgtgta tacccgcaag     540
actttcgagc gcgagctggc tctggagtgg atcattccag atgcagagga agcataaacc     600
ggttttaaat atgtcttaca gtatcactac tccatctcag ttcgtgttct tgtcatcagc     660
gtgggccgac ccaatagagt taattaattt atgtactaat gccttaggaa atcagtttca     720
aacacaacaa gctcgaactg tcgttcaaag acaattcagt gaggtgtgga acctttcacc     780
acaagtaact gttaggttcc ctgacagtga ctttaaggtg tacaggtaca atgcggtatt     840
agacccgcta gtcacagcac tgttaggtgc attcgacact agaaatagaa taatagaagt     900
tgaaaatcag gcgaacccca cgactgccga aacgttagat gctactcgta gagtagacga     960
cgcaacggtg gccataagga gcgcgataaa taatttaata gtagaattga tcagaggaac    1020
cggatcttat aatcggagct ctttcgagag ctcttctggt ttggtttgga cctctggtcc    1080
tgcaacttga tagtccggac ctgcaggacg cgtgtcgacg tttgagagag aagattacaa    1140
acgtgagaga cggagggccc atggaactta cagaagaagt cgttgatgag ttcatggaag    1200
```

-continued

| | |
|---|---|
| atgtccctat gtcgatcagg cttgcaaagt ttcgatctcg aaccggccta ggctcgtggt | 1260 |
| attgtttata gaataatat aaaattaggt ttgagagaga agattacaaa cgtgagagac | 1320 |
| ggagggccca tggaacttac agaagaagtc gttgatgagt tcatggaaga tgtccctatg | 1380 |
| tcgatcaggc ttgcaaagtt tcgatctcga accggaaaaa agagtgatgt ccgcaaaggg | 1440 |
| aaaaata | 1447 |

<210> SEQ ID NO 16
<211> LENGTH: 6560
<212> TYPE: DNA
<213> ORGANISM: Artificial Sequence
<220> FEATURE:
<223> OTHER INFORMATION: pET21 plasmid vector carrying the sequence for BSMV-CP with a point mutation at residue D70N

<400> SEQUENCE: 16

| | |
|---|---|
| tctgctgctt gcaaacaaaa aaaccaccgc taccagcggt ggtttgtttg ccggatcaag | 60 |
| agctaccaac tcttttttccg aaggtaactg gcttcagcag agcgcagata ccaaatactg | 120 |
| tccttctagt gtagccgtag ttaggccacc acttcaagaa ctctgtagca ccgcctacat | 180 |
| acctcgctct gctaatcctg ttaccagtgg ctgctgccag tggcgataag tcgtgtctta | 240 |
| ccggggttgga ctcaagacga tagttaccgg ataaggcgca gcggtcgggc tgaacggggg | 300 |
| gttcgtgcac acagcccagc ttggagcgaa cgacctacac cgaactgaga tacctacagc | 360 |
| gtgagctatg agaaagcgcc acgcttcccg aagggagaaa ggcggacagg tatccggtaa | 420 |
| gcggcagggt cggaacagga gagcgcacga gggagcttcc agggggaaac gcctggtatc | 480 |
| tttatagtcc tgtcgggttt cgccacctct gacttgagcg tcgatttttg tgatgctcgt | 540 |
| caggggggcg gagcctatgg aaaaacgcca gcaacgcggc cttttacgg ttcctggcct | 600 |
| tttgctggcc ttttgctcac atgttctttc ctgcgttatc ccctgattct gtggataacc | 660 |
| gtattaccgc ctttgagtga gctgataccg ctcgccgcag ccgaacgacc gagcgcagcg | 720 |
| agtcagtgag cgaggaagcg gaagagcgcc tgatgcggta ttttctcctt acgcatctgt | 780 |
| gcggtatttc acaccgcaat ggtgcactct cagtacaatc tgctctgatg ccgcatagtt | 840 |
| aagccagtat acactccgct atcgctacgt gactgggtca tggctgcgcc ccgacacccg | 900 |
| ccaacacccg ctgacgcgcc ctgacgggct tgtctgctcc cggcatccgc ttacagacaa | 960 |
| gctgtgaccg tctccgggag ctgcatgtgt cagaggtttt caccgtcatc accgaaacgc | 1020 |
| gcgaggcagc tgcggtaaag ctcatcagcg tggtcgtgaa gcgattcaca gatgtctgcc | 1080 |
| tgttcatccg cgtccagctc gttgagtttc tccagaagcg ttaatgtctg gcttctgata | 1140 |
| aagcgggcca tgttaagggc ggttttttcc tgtttggtca ctgatgcctc cgtgtaaggg | 1200 |
| ggatttctgt tcatgggggt aatgataccg atgaaacgag agaggatgct cacgatacgg | 1260 |
| gttactgatg atgaacatgc ccggttactg gaacgttgtg agggtaaaca actggcggta | 1320 |
| tggatgcggc gggaccagag aaaaatcact caggtcaat gccagcgctt cgttaataca | 1380 |
| gatgtaggtg ttccacaggg tagccagcag catcctgcga tgcagatccg gaacataatg | 1440 |
| gtgcagggcg ctgacttccg cgtttccaga ctttacgaaa cacggaaacc gaagaccatt | 1500 |
| catgttgttg ctcaggtcgc agacgttttg cagcagcagt cgcttcacgt tcgctcgcgt | 1560 |
| atcggtgatt cattctgcta accagtaagg caaccccgcc agcctagccg ggtcctcaac | 1620 |
| gacaggagca cgatcatgcg cacccgtggg gccgccatgc cggcgataat ccccgccagc | 1680 |
| ctagccgggt cctcaacgac aggagcacga tcatgcgcac ccgtggggcc gccatgccgg | 1740 |

```
cgataatggc ctgcttctcg ccgaaacgtt tggtggcggg accagtgacg aaggcttgag    1800
cgagggcgtg caagattccg aataccgcaa gcgacaggcc gatcatcgtc gcgctccagc    1860
gaaagcggtc ctcgccgaaa atgacccaga gcgctgccgg cacctgtcct acgagttgca    1920
tgataaagaa gacagtcata agtgcggcga cgatagtcat gccccgcgcc caccggaagg    1980
agctgactgg gttgaaggct ctcaagggca tcggtcgaga tcccggtgcc taatgagtga    2040
gctaacttac attaattgcg ttgcgctcac tgcccgcttt ccagtcggga aacctgtcgt    2100
gccagctgca ttaatgaatc ggccaacgcg cggggagagg cggtttgcgt attgggcgcc    2160
agggtggttt ttcttttcac cagtgagacg ggcaacagct gattgccctt caccgcctgg    2220
ccctgagaga gttgcagcaa gcggtccacg ctggtttgcc ccagcaggcg aaaatcctgt    2280
ttgatggtgg ttaacggcgg gatataacat gagctgtctt cggtatcgtc gtatcccact    2340
accgagatat ccgcaccaac gcgcagcccg gactcggtaa tggcgcgcat tgcgcccagc    2400
gccatctgat cgttggcaac cagcatcgca gtgggaacga tgccctcatt cagcatttgc    2460
atggtttgtt gaaaaccgga catggcactc cagtcgcctt cccgttccgc tatcggctga    2520
atttgattgc gagtgagata tttatgccag ccagccagac gcagacgcgc cgagacagaa    2580
cttaatgggc ccgctaacag cgcgatttgc tggtgaccca atgcgaccag atgctccacg    2640
cccagtcgcg taccgtcttc atgggagaaa ataatactgt tgatgggtgt ctggtcagag    2700
acatcaagaa ataacgccgg aacattagtg caggcagctt ccacagcaat ggcatcctgg    2760
tcatccagcg gatagttaat gatcagccca ctgacgcgtt gcgcgagaag attgtgcacc    2820
gccgctttac aggcttcgac gccgcttcgt tctaccatcg acaccaccac gctggcaccc    2880
agttgatcgg cgcgagattt aatcgccgcg acaatttgcg acggcgcgtg cagggccaga    2940
ctggaggtgg caacgccaat cagcaacgac tgtttgcccg ccagttgttg tgccacgcgg    3000
ttgggaatgt aattcagctc cgccatcgcc gcttccactt ttcccgcgt tttcgcagaa     3060 acgtggctgg cctggttcac cacgcgggaa acggtctgat aagagacacc ggcatactct    3120
gcgacatcgt ataacgttac tggtttcaca ttcaccaccc tgaattgact ctcttccggg    3180
cgctatcatg ccataccgcg aaaggttttg cgccattcga tggtgtccgg gatctcgacg    3240
ctctccctta tgcgactcct gcattaggaa gcagcccagt agtaggttga ggccgttgag    3300
caccgccgcc gcaaggaatg gtgcatgcaa ggagatggcg cccaacagtc ccccggccac    3360
ggggcctgcc accataccca cgccgaaaca agcgctcatg agcccgaagt ggcgagcccg    3420
atcttcccca tcggtgatgt cggcgatata ggcgccagca accgcacctg tggcgccggt    3480
gatgccggcc acgatgcgtc cggcgtagag gatcgagatc tcgatcccgc gaaattaata    3540
cgactcacta tagggaatt gtgagcggat aacaattccc ctctagaaat aattttgttt    3600
aactttaaga aggagatata catatgatgc ccaacgtatc actgacagcg aaaggggag    3660 gtcattacat cgaagatcag tgggatacgc aagtcgtcga agcaggagtg ttcgacgact    3720
ggtgggtgca tgtagaggcc tggaataagt ttcttgacaa tctgcgcggc atcaattttt    3780
ccgtcgccag cagtcgctca caagtagcag agtatttggc tgctttggat cgtaaccttc    3840
cggctgacgt tgatcgtcgt ttcgcgggtg cacgtggtca atcggcagc cccaattact     3900 taccagcacc taaattttt cgtcttgata aacgtacaat cgctgaattg acacgtttgt      3960
cgcgcttgac ggatcagccc cacaacaatc gtgatatcga gttaaatcgc gcaaaacgcg    4020
caacaacaaa tcctagccca cctgctcaag ccccagcgca aaaccttaca ctgcgcgacg    4080
tgcaaccctt aaaggactcc gcgttacatt atcagtatgt ccttattgat cttcagtccg    4140
```

```
cacgcttgcc tgtgtatacc cgcaagactt tcgagcgcga gctggctctg gagtggatca    4200
ttccagatgc agaggaagca taaaccggtt ttaaatatgt cttacagtat cactactcca    4260
tctcagttcg tgttcttgtc atcagcgtgg gccgacccaa tagagttaat taatttatgt    4320
actaatgcct taggaaatca gtttcaaaca caacaagctc gaactgtcgt tcaaagacaa    4380
ttcagtgagg tgtggaaacc ttcaccacaa gtaactgtta ggttccctga cagtgacttt    4440
aaggtgtaca ggtacaatgc ggtattagac ccgctagtca cagcactgtt aggtgcattc    4500
gacactagaa atagaataat agaagttgaa atcaggcga acccacgac tgccgaaacg    4560 ttagatgcta ctcgtagagt agacgacgca acggtggcca taaggagcgc gataaataat    4620
ttaatagtag aattgatcag aggaaccgga tcttataatc ggagctcttt cgagagctct    4680 tctggttttgg tttggacctc tggtcctgca acttgatagt ccggacctgc aggacgcgtg    4740
tcgatcgagc accaccacca ccaccactga gatccggctg ctaacaaagc ccgaaggaa    4800 gctgagttgg ctgctgccac cgctgagcaa taactagcat aacccttgg ggcctctaaa    4860 cgggtcttga ggggttttttt gctgaaagga ggaactatat ccggattggc gaatgggacg    4920
cgccctgtag cggcgcatta gcgcggcgg gtgtggtggt tacgcgcagc gtgaccgcta    4980
cacttgccag cgccctagcg cccgctcctt tcgctttctt cccttccttt ctcgccacgt    5040
tcgccggctt tccccgtcaa gctctaaatc ggggctccc tttagggttc cgatttagtg    5100
ctttacggca cctcgacccc aaaaaacttg attagggtga tggttcacgt agtgggccat    5160
cgccctgata cggtttttc gcccctttga cgttggagtc cacgttcttt aatagtggac    5220
tcttgttcca aactggaaca cactcaacc ctatctcggt ctattctttt gatttataag    5280
ggattttgcc gatttcggcc tattggttaa aaatgagct gatttaacaa aaatttaacg    5340
cgaattttaa caaaatatta acgcttacaa tttaggtggc acttttcggg gaaatgtgcg    5400
cggaacccct atttgtttat ttttctaaat acattcaaat atgtatccgc tcatgagaca    5460
ataaccctga taaatgcttc aataatattg aaaaggaag agtatgagta ttcaacattt    5520
ccgtgtcgcc cttattccct tttttgcggc attttgcctt cctgttttg ctcacccaga    5580 aacgctggtg aaagtaaaag atgctgaaga tcagttggg gcacgagtgg gttacatcga    5640
actggatctc aacagcggta agatccttga gagttttcgc cccgaagaac gttttccaat    5700
gatgagcact tttaaagttc tgctatgtgg cgcggtatta tcccgtattg acgccgggca    5760
agagcaactc ggtcgccgca tacactattc tcagaatgac ttggttgagt actcaccagt    5820
cacagaaaag catcttacgg atggcatgac agtaagagaa ttatgcagtg ctgccataac    5880
catgagtgat aacactgcgg ccaacttact tctgacaacg atcggaggac cgaaggagct    5940
aaccgctttt ttgcacaaca tgggggatca tgtaactcgc cttgatcgtt gggaaccgga    6000
gctgaatgaa gccataccaa acgacgagcg tgacaccacg atgcctgcag caatggcaac    6060
aacgttgcgc aaactattaa ctggcgaact acttactcta gcttcccggc aacaattaat    6120
agactggatg gaggcggata agttgcagg accacttctg cgctcggccc ttccggctgg    6180
ctggtttatt gctgataaat ctggagccgg tgagcgtggg tctcgcggta tcattgcagc    6240
actggggcca gatggtaagc cctcccgtat cgtagttatc tacacgacgg ggagtcaggc    6300
aactatggat gaacgaaata gacagatcgc tgagataggt gcctcactga ttaagcattg    6360
gtaactgtca gaccaagttt actcatatat actttagatt gatttaaaac ttcatttttta    6420 atttaaaagg atctaggtga agatccttttt tgataatctc atgaccaaaa tcccttaacg    6480
```

```
tgagttttcg ttccactgag cgtcagaccc cgtagaaaag atcaaaggat cttcttgaga    6540
tcctttttt ctgcgcgtaa                                                  6560
```

<210> SEQ ID NO 17
<211> LENGTH: 6560
<212> TYPE: DNA
<213> ORGANISM: Artificial Sequence
<220> FEATURE:
<223> OTHER INFORMATION: pET21 plasmid vector carrying the sequence for BSMV-CP with a point mutation at the D68N residue

<400> SEQUENCE: 17

```
tctgctgctt gcaaacaaaa aaaccaccgc taccagcggt ggtttgtttg ccggatcaag      60
agctaccaac tcttttttccg aaggtaactg gcttcagcag agcgcagata ccaaatactg    120
tccttctagt gtagccgtag ttaggccacc acttcaagaa ctctgtagca ccgcctacat    180
acctcgctct gctaatcctg ttaccagtgg ctgctgccag tggcgataag tcgtgtctta    240
ccgggttgga ctcaagacga tagttaccgg ataaggcgca gcggtcgggc tgaacggggg    300
gttcgtgcac acagcccagc ttggagcgaa cgacctacac cgaactgaga tacctacagc    360
gtgagctatg agaaagcgcc acgcttcccg aagggagaaa ggcggacagg tatccggtaa    420
gcggcagggt cggaacagga gagcgcacga gggagcttcc agggggaaac gcctggtatc    480
tttatagtcc tgtcgggttt cgccacctct gacttgagcg tcgatttttg tgatgctcgt    540
caggggggcg gagcctatgg aaaaacgcca gcaacgcggc cttttttacgg ttcctggcct    600
tttgctggcc ttttgctcac atgttctttc ctgcgttatc ccctgattct gtggataacc    660
gtattaccgc ctttgagtga gctgataccg ctcgccgcag ccgaacgacc gagcgcagcg    720
agtcagtgag cgaggaagcg gaagagcgcc tgatgcggta ttttctcctt acgcatctgt    780
gcggtatttc acaccgcaat ggtgcactct cagtacaatc tgctctgatg ccgcatagtt    840
aagccagtat acactccgct atcgctacgt gactgggtca tggctgcgcc ccgacacccg    900
ccaacacccg ctgacgcgcc ctgacgggct tgtctgctcc cggcatccgc ttacagacaa    960
gctgtgaccg tctccgggag ctgcatgtgt cagaggtttt caccgtcatc accgaaacgc   1020
gcgaggcagc tgcggtaaag ctcatcagcg tggtcgtgaa gcgattcaca gatgtctgcc   1080
tgttcatccg cgtccagctc gttgagtttc tccagaagcg ttaatgtctg gcttctgata   1140
aagcgggcca tgttaaggc ggtttttttcc tgtttggtca ctgatgcctc cgtgtaaggg   1200
ggatttctgt tcatgggggt aatgataccg atgaaacgag agaggatgct cacgatacgg   1260
gttactgatg atgaacatgc ccggttactg gaacgttgtg agggtaaaca actggcggta   1320
tggatgcggc gggaccagag aaaaatcact cagggtcaat gccagcgctt cgttaataca   1380
gatgtaggtg ttccacaggg tagccagcag catcctgcga tgcagatccg gaacataatg   1440
gtgcagggcg ctgacttccg cgtttccaga ctttacgaaa cacggaaacc gaagaccatt   1500
catgttgttg ctcaggtcgc agacgttttg cagcagcagt cgcttcacgt tcgctcgcgt   1560
atcggtgatt cattctgcta accagtaagg caacccccgcc agcctagccg gtcctcaac   1620
gacaggagca cgatcatgcg cacccgtggg gccgccatgc cggcgataat ccccgccagc   1680
ctagccgggt cctcaacgac aggagcacga tcatgcgcac ccgtggggcc gccatgccgg   1740
cgataatggc ctgcttctcg ccgaaacgtt tggtggcggg accagtgacg aaggcttgag   1800
cgagggcgtg caagattccg aataccgcaa gcgacaggcc gatcatcgtc gcgctccagc   1860
gaaagcggtc ctcgccgaaa atgacccaga gcgctgccgg cacctgtcct acgagttgca   1920
```

```
tgataaagaa gacagtcata agtgcggcga cgatagtcat gccccgcgcc caccggaagg    1980
agctgactgg gttgaaggct ctcaagggca tcggtcgaga tcccggtgcc taatgagtga    2040
gctaacttac attaattgcg ttgcgctcac tgcccgcttt ccagtcggga aacctgtcgt    2100
gccagctgca ttaatgaatc ggccaacgcg cggggagagg cggtttgcgt attgggcgcc    2160
agggtggttt ttcttttcac cagtgagacg ggcaacagct gattgccctt caccgcctgg    2220
ccctgagaga gttgcagcaa gcggtccacg ctggtttgcc ccagcaggcg aaaatcctgt    2280
ttgatggtgg ttaacggcgg gatataacat gagctgtctt cggtatcgtc gtatcccact    2340
accgagatat ccgcaccaac gcgcagcccg gactcggtaa tggcgcgcat tgcgcccagc    2400
gccatctgat cgttggcaac cagcatcgca gtgggaacga tgccctcatt cagcatttgc    2460
atggtttgtt gaaaaccgga catggcactc cagtcgcctt cccgttccgc tatcggctga    2520
atttgattgc gagtgagata tttatgccag ccagccagac gcagacgcgc cgagacagaa    2580
cttaatgggc ccgctaacag cgcgatttgc tggtgaccca atgcgaccag atgctccacg    2640
cccagtcgcg taccgtcttc atgggagaaa ataatactgt tgatgggtgt ctggtcagag    2700
acatcaagaa ataacgccgg aacattagtg caggcagctt ccacagcaat ggcatcctgg    2760
tcatccagcg gatagttaat gatcagccca ctgacgcgtt gcgcgagaag attgtgcacc    2820
gccgctttac aggcttcgac gccgcttcgt tctaccatcg acaccaccac gctggcaccc    2880
agttgatcgg cgcgagattt aatcgccgcg acaatttgcg acggcgcgtg cagggccaga    2940
ctggaggtgg caacgccaat cagcaacgac tgtttgcccg ccagttgttg tgccacgcgg    3000
ttgggaatgt aattcagctc cgccatcgcc gcttccactt ttcccgcgt tttcgcagaa    3060 acgtggctgg cctggttcac cacgcgggaa acggtctgat aagagacacc ggcatactct    3120
gcgacatcgt ataacgttac tggtttcaca ttcaccaccc tgaattgact ctcttccggg    3180
cgctatcatg ccataccgcg aaaggttttg cgccattcga tggtgtccgg atctcgacg    3240 ctctccctta tgcgactcct gcattaggaa gcagcccagt agtaggttga ggccgttgag    3300
caccgccgcc gcaaggaatg gtgcatgcaa ggagatggcg cccaacagtc ccccggccac    3360
ggggcctgcc accataccca cgccgaaaca agcgctcatg agcccgaagt ggcgagcccg    3420
atcttcccca tcggtgatgt cggcgatata ggcgccagca accgcacctg tggcgccggt    3480
gatgccggcc acgatgcgtc cggcgtagag gatcgagatc tcgatcccgc gaaattaata    3540
cgactcacta tagggaatt gtgagcggat aacaattccc ctctagaaat aattttgttt    3600
aactttaaga aggagatata catatgatgc ccaacgtatc actgacagcg aaaggggag    3660 gtcattacat cgaagatcag tgggatacgc aagtcgtcga agcaggagtg ttcgacgact    3720
ggtgggtgca tgtagaggcc tggaataagt ttcttgacaa tctgcgcggc atcaattttt    3780
ccgtcgccag cagtcgctca caagtagcag agtatttggc tgctttgaat cgtgaccttc    3840
cggctgacgt tgatcgtcgt ttcgcggggtg cacgtggtca atcggcagc cccaattact    3900 taccagcacc taaattttt cgtcttgata aacgtacaat cgctgaattg acacgtttgt    3960
cgcgcttgac ggatcagccc cacaacaatc gtgatatcga gttaaatcgc gcaaaacgcg    4020
caacaacaaa tcctagccca cctgctcaag ccccagcgaa aaaccttaca ctgcgcgacg    4080 tgcaacccctt aaaggactcc gcgttacatt atcagtatgt ccttattgat cttcagtccg    4140
cacgcttgcc tgtgtatacc cgcaagactt tcgagcgcga gctggctctg gagtggatca    4200
ttccagatgc agaggaagca taaaccggtt ttaaatatgt cttacagtat cactactcca    4260
tctcagttcg tgttcttgtc atcagcgtgg gccgacccaa tagagttaat taatttatgt    4320
```

```
actaatgcct taggaaatca gtttcaaaca caacaagctc gaactgtcgt tcaaagacaa   4380
ttcagtgagg tgtggaaacc ttcaccacaa gtaactgtta ggttccctga cagtgacttt   4440
aaggtgtaca ggtacaatgc ggtattagac ccgctagtca cagcactgtt aggtgcattc   4500
gacactagaa atagaataat agaagttgaa atcaggcga accccacgac tgccgaaacg    4560
ttagatgcta ctcgtagagt agacgacgca acggtggcca taaggagcgc gataaataat   4620
ttaatagtag aattgatcag aggaaccgga tcttataatc ggagctcttt cgagagctct   4680
tctggtttgg tttggaccct ctggtcctgca acttgatagt ccggacctgc aggacgcgtg  4740
tcgatcgagc accaccacca ccaccactga gatccggctg ctaacaaagc ccgaaaggaa   4800
gctgagttgg ctgctgccac cgctgagcaa taactagcat aacccettgg ggcctctaaa   4860 cgggtcttga ggggtttttt gctgaaagga ggaactatat ccggattggc gaatgggacg   4920
cgccctgtag cggcgcatta agcgcggcgg gtgtggtggt tacgcgcagc gtgaccgcta   4980
cacttgccag cgccctagcg cccgctcctt tcgctttctt cccttccttt ctcgccacgt   5040
tcgccggctt tccccgtcaa gctctaaatc ggggctccc tttagggttc cgatttagtg    5100
ctttacggca cctcgacccc aaaaaacttg attagggtga tggttcacgt agtgggccat   5160
cgccctgata gacggttttt cgccctttga cgttggagtc cacgttcttt aatagtggac   5220
tcttgttcca aactggaaca cactcaacc ctatctcggt ctattctttt gatttataag    5280
ggattttgcc gatttcggcc tattggttaa aaatgagct gatttaacaa aaatttaacg    5340
cgaattttaa caaatatta acgcttacaa tttaggtggc acttttcggg gaaatgtgcg    5400
cggaacccct atttgtttat ttttctaaat acattcaaat atgtatccgc tcatgagaca   5460
ataaccctga taaatgcttc aataatattg aaaaaggaag agtatgagta ttcaacattt   5520
ccgtgtcgcc cttattccct ttttgcggc attttgcctt cctgttttg ctcacccaga     5580 aacgctggtg aaagtaaaag atgctgaaga tcagttgggt gcacgagtgg gttacatcga   5640
actggatctc aacagcggta agatccttga gagttttcgc cccgaagaac gttttccaat   5700
gatgagcact tttaaagttc tgctatgtgg cgcggtatta tcccgtattg acgccgggca   5760
agagcaactc ggtcgccgca tacactattc tcagaatgac ttggttgagt actcaccagt   5820
cacagaaaag catcttacgg atggcatgac agtaagagaa ttatgcagtg ctgccataac   5880
catgagtgat aacactgcgg ccaacttact tctgacaacg atcggaggac cgaaggagct   5940
aaccgctttt ttgcacaaca tgggggatca tgtaactcgc cttgatcgtt gggaaccgga   6000
gctgaatgaa gccataccaa acgacgagcg tgacaccacg atgcctgcag caatggcaac   6060
aacgttgcgc aaactattaa ctggcgaact acttactcta gcttcccggc aacaattaat   6120
agactggatg gaggcggata aagttgcagg accacttctg cgctcggccc ttccggctgg   6180
ctggtttatt gctgataaat ctggagccgg tgagcgtggg tctcgcggta tcattgcagc   6240
actggggcca gatggtaagc cctcccgtat cgtagttatc tacacgacgg ggagtcaggc   6300
aactatggat gaacgaaata gacagatcgc tgagataggt gcctcactga ttaagcattg   6360
gtaactgtca gaccaagttt actcatatat actttagatt gatttaaaac ttcattttta   6420
atttaaaagg atctaggtga agatcctttt tgataatctc atgaccaaaa tcccttaacg   6480
tgagttttcg ttccactgag cgtcagaccc cgtagaaaag atcaaaggat cttcttgaga   6540
tccttttttt ctgcgcgtaa                                                6560
```

<210> SEQ ID NO 18

<211> LENGTH: 6560
<212> TYPE: DNA
<213> ORGANISM: Artificial Sequence
<220> FEATURE:
<223> OTHER INFORMATION: pET21 plasmid vector carrying the sequence for BSMV-CP with a point mutation at residue D101K

<400> SEQUENCE: 18

| | | | | | |
|---|---|---|---|---|---|
| tctgctgctt | gcaaacaaaa | aaaccaccgc | taccagcggt | ggtttgtttg | ccggatcaag | 60 |
| agctaccaac | tcttttttccg | aaggtaactg | gcttcagcag | agcgcagata | ccaaatactg | 120 |
| tccttctagt | gtagccgtag | ttaggccacc | acttcaagaa | ctctgtagca | ccgcctacat | 180 |
| acctcgctct | gctaatcctg | ttaccagtgg | ctgctgccag | tggcgataag | tcgtgtctta | 240 |
| ccggggttgga | ctcaagacga | tagttaccgg | ataaggcgca | gcggtcgggc | tgaacggggg | 300 |
| gttcgtgcac | acagcccagc | ttggagcgaa | cgacctacac | cgaactgaga | tacctacagc | 360 |
| gtgagctatg | agaaagcgcc | acgcttcccg | aagggagaaa | ggcggacagg | tatccggtaa | 420 |
| gcggcagggt | cggaacagga | gagcgcacga | gggagcttcc | aggggggaaac | gcctggtatc | 480 |
| tttatagtcc | tgtcgggttt | cgccacctct | gacttgagcg | tcgatttttg | tgatgctcgt | 540 |
| caggggggcg | gagcctatgg | aaaaacgcca | gcaacgcggc | cttttttacgg | ttcctggcct | 600 |
| tttgctggcc | ttttgctcac | atgttctttc | ctgcgttatc | ccctgattct | gtggataacc | 660 |
| gtattaccgc | ctttgagtga | gctgataccg | ctcgccgcag | ccgaacgacc | gagcgcagcg | 720 |
| agtcagtgag | cgaggaagcg | gaagagcgcc | tgatgcggta | ttttctcctt | acgcatctgt | 780 |
| gcggtatttc | acaccgcaat | ggtgcactct | cagtacaatc | tgctctgatg | ccgcatagtt | 840 |
| aagccagtat | acactccgct | atcgctacgt | gactgggtca | tggctgcgcc | ccgacacccg | 900 |
| ccaacacccg | ctgacgcgcc | ctgacgggct | tgtctgctcc | cggcatccgc | ttacagacaa | 960 |
| gctgtgaccg | tctccgggag | ctgcatgtgt | cagaggtttt | caccgtcatc | accgaaacgc | 1020 |
| gcgaggcagc | tgcggtaaag | ctcatcagcg | tggtcgtgaa | gcgattcaca | gatgtctgcc | 1080 |
| tgttcatccg | cgtccagctc | gttgagtttc | tccagaagcg | ttaatgtctg | gcttctgata | 1140 |
| aagcgggcca | tgttaagggc | ggttttttcc | tgtttggtca | ctgatgcctc | cgtgtaaggg | 1200 |
| ggatttctgt | tcatgggggt | aatgataccg | atgaaacgag | agaggatgct | cacgatacgg | 1260 |
| gttactgatg | atgaacatgc | ccggttactg | gaacgttgtg | agggtaaaca | actggcggta | 1320 |
| tggatgcggc | gggaccagag | aaaaatcact | cagggtcaat | gccagcgctt | cgttaataca | 1380 |
| gatgtaggtg | ttccacaggg | tagccagcag | catcctgcga | tgcagatccg | gaacataatg | 1440 |
| gtgcagggcg | ctgacttccg | cgtttccaga | ctttacgaaa | cacggaaacc | gaagaccatt | 1500 |
| catgttgttg | ctcaggtcgc | agacgttttg | cagcagcagt | cgcttcacgt | tcgctcgcgt | 1560 |
| atcggtgatt | cattctgcta | accagtaagg | caaccccgcc | agcctagccg | ggtcctcaac | 1620 |
| gacaggagca | cgatcatgcg | cacccgtggg | gccgccatgc | cggcgataat | ccccgccagc | 1680 |
| ctagccgggt | cctcaacgac | aggagcacga | tcatgcgcac | ccgtgggcc | gccatgccgg | 1740 |
| cgataatggc | ctgcttctcg | ccgaaacgtt | tggtggcggg | accagtgacg | aaggcttgag | 1800 |
| cgagggcgtg | caagattccg | aataccgcaa | gcgacaggcc | gatcatcgtc | gcgctccagc | 1860 |
| gaaagcggtc | ctcgccgaaa | atgacccaga | gcgctgccgg | cacctgtcct | acgagttgca | 1920 |
| tgataaagaa | gacagtcata | agtgcggcga | cgatagtcat | gccccgcgcc | caccggaagg | 1980 |
| agctgactgg | gttgaaggct | ctcaagggca | tcggtcgaga | tcccggtgcc | taatgagtga | 2040 |
| gctaacttac | attaattgcg | ttgcgctcac | tgcccgcttt | ccagtcggga | aacctgtcgt | 2100 |

```
gccagctgca ttaatgaatc ggccaacgcg cggggagagg cggtttgcgt attgggcgcc    2160
agggtggttt ttcttttcac cagtgagacg ggcaacagct gattgccctt caccgcctgg    2220
ccctgagaga gttgcagcaa gcggtccacg ctggtttgcc ccagcaggcg aaaatcctgt    2280
ttgatggtgg ttaacggcgg gatataacat gagctgtctt cggtatcgtc gtatcccact    2340
accgagatat ccgcaccaac gcgcagcccg gactcggtaa tggcgcgcat tgcgcccagc    2400
gccatctgat cgttggcaac cagcatcgca gtgggaacga tgccctcatt cagcatttgc    2460
atggtttgtt gaaaaccgga catggcactc cagtcgcctt cccgttccgc tatcggctga    2520
atttgattgc gagtgagata tttatgccag ccagccagac gcagacgcgc cgagacagaa    2580
cttaatgggc ccgctaacag cgcgatttgc tggtgaccca atgcgaccag atgctccacg    2640
cccagtcgcg taccgtcttc atgggagaaa ataatactgt tgatgggtgt ctggtcagag    2700
acatcaagaa ataacgccgg aacattagtg caggcagctt ccacagcaat ggcatcctgg    2760
tcatccagcg gatagttaat gatcagccca ctgacgcgtt gcgcgagaag attgtgcacc    2820
gccgctttac aggcttcgac gccgcttcgt tctaccatcg acaccaccac gctggcaccc    2880
agttgatcgg cgcgagattt aatcgccgcg acaatttgcg acggcgcgtg cagggccaga    2940
ctggaggtgg caacgccaat cagcaacgac tgtttgcccg ccagttgttg tgccacgcgg    3000
ttgggaatgt aattcagctc cgccatcgcc gcttccactt tttcccgcgt tttcgcagaa    3060
acgtggctgg cctggttcac cacgcgggaa acggtctgat aagagacacc ggcatactct    3120
gcgacatcgt ataacgttac tggtttcaca ttcaccaccc tgaattgact ctcttccggg    3180
cgctatcatg ccataccgcg aaaggttttg cgccattcga tggtgtccgg gatctcgacg    3240
ctctccctta tgcgactcct gcattaggaa gcagcccagt agtaggttga ggccgttgag    3300
caccgccgcc gcaaggaatg gtgcatgcaa ggagatggcg cccaacagtc ccccggccac    3360
ggggcctgcc accatacccca cgccgaaaca agcgctcatg agcccgaagt ggcgagcccg    3420
atcttcccca tcggtgatgt cggcgatata ggcgccagca accgcacctg tggcgccggt    3480
gatgccggcc acgatgcgtc cggcgtagag gatcgagatc tcgatcccgc gaaattaata    3540
cgactcacta tagggggaatt gtgagcggat aacaattccc ctctagaaat aattttgttt    3600
aactttaaga aggagatata catatgatgc ccaacgtatc actgacagcg aaaggggag    3660 gtcattacat cgaagatcag tgggatacgc aagtcgtcga agcaggagtg ttcgacgact    3720
ggtgggtgca tgtagaggcc tggaataagt ttcttgacaa tctgcgcggc atcaatttt    3780 ccgtcgccag cagtcgctca caagtagcag agtatttggc tgctttggat cgtgaccttc    3840
cggctgacgt tgatcgtcgt ttcgcgggtg cacgtggtca aatcggcagc cccaattact    3900
taccagcacc taaattttt cgtcttaaaa aacgtacaat cgctgaattg acacgtttgt    3960
cgcgcttgac ggatcagccc cacaacaatc gtgatatcga gttaaatcgc gcaaaacgcg    4020
caacaacaaa tcctagccca cctgctcaag ccccgagcga aaaccttaca ctgcgcgacg    4080
tgcaacccct taaaggactcc gcgttacatt atcagtatgt ccttattgat cttcagtccg    4140
cacgcttgcc tgtgtatacc cgcaagactt tcgagcgcga gctggctctg gagtggatca    4200
ttccagatgc agaggaagca taaaccggtt ttaaatatgt cttacagtat cactactcca    4260
tctcagttcg tgttcttgtc atcagcgtgg gccgacccaa tagagttaat taatttatgt    4320
actaatgcct taggaaatca gtttcaaaca caacaagctc gaactgtcgt tcaaagacaa    4380
ttcagtgagg tgtggaaacc ttcaccacaa gtaactgtta ggttccctga cagtgacttt    4440
aaggtgtaca ggtacaatgc ggtattagac ccgctagtca cagcactgtt aggtgcattc    4500
```

```
gacactagaa atagaataat agaagttgaa aatcaggcga accccacgac tgccgaaacg    4560
ttagatgcta ctcgtagagt agacgacgca acggtggcca taaggagcgc gataaataat    4620
ttaatagtag aattgatcag aggaaccgga tcttataatc ggagctcttt cgagagctct    4680
tctggtttgg tttggacctc tggtcctgca acttgatagt ccggacctgc aggacgcgtg    4740
tcgatcgagc accaccacca ccaccactga gatccggctg ctaacaaagc ccgaaggaa     4800
gctgagttgg ctgctgccac cgctgagcaa taactagcat aacccttgg ggcctctaaa    4860
cgggtcttga ggggtttttt gctgaaagga ggaactatat ccggattggc gaatgggacg    4920
cgccctgtag cggcgcatta gcgcggcgg tgtggtggt tacgcgcagc gtgaccgcta    4980
cacttgccag cgccctagcg cccgctcctt tcgctttctt cccttccttt ctcgccacgt   5040
tcgccggctt ccccgtcaa gctctaaatc ggggctccc tttagggttc cgatttagtg    5100
ctttacggca cctcgacccc aaaaaacttg attagggtga tggttcacgt agtgggccat   5160
cgccctgata cacggttttt cgccctttga cgttggagtc cacgttcttt aatagtggac   5220
tcttgttcca aactggaaca acactcaacc ctatctcggt ctattctttt gatttataag   5280
ggattttgcc gatttcggcc tattggttaa aaatgagct gatttaacaa aaatttaacg    5340
cgaattttaa caaaatatta acgcttacaa tttaggtggc acttttcggg gaaatgtgcg   5400
cggaacccct atttgtttat ttttctaaat acattcaaat atgtatccgc tcatgagaca   5460
ataaccctga taaatgcttc aataatattg aaaaggaag agtatgagta ttcaacattt    5520
ccgtgtcgcc cttattccct tttttgcggc attttgcctt cctgttttg ctcacccaga    5580
aacgctggtg aaagtaaaag atgctgaaga tcagttgggt gcacgagtgg gttacatcga   5640
actggatctc aacagcggta agatccttga gagttttcgc cccgaagaac gttttccaat   5700
gatgagcact tttaaagttc tgctatgtgg cgcggtatta tcccgtattg acgccgggca   5760
agagcaactc ggtcgccgca tacactattc tcagaatgac ttggttgagt actcaccagt   5820
cacagaaaag catcttacgg atggcatgac agtaagagaa ttatgcagtg ctgccataac   5880
catgagtgat aacactgcgg ccaacttact tctgacaacg atcggaggac cgaaggagct   5940
aaccgctttt ttgcacaaca tgggggatca tgtaactcgc cttgatcgtt gggaaccgga   6000
gctgaatgaa gccataccaa acgacgagcg tgacaccacg atgcctgcag caatggcaac   6060
aacgttgcgc aaactattaa ctggcgaact acttactcta gcttcccggc aacaattaat   6120
agactggatg gaggcggata agttgcagg accacttctg cgctcggccc ttccggctgg   6180
ctggtttatt gctgataaat ctggagccgg tgagcgtggg tctcgcggta tcattgcagc   6240
actggggcca gatggtaagc cctcccgtat cgtagttatc tacacgacgg ggagtcaggc   6300
aactatggat gaacgaaata gacagatcgc tgagataggt gcctcactga ttaagcattg   6360
gtaactgtca gaccaagttt actcatatat actttagatt gatttaaaac ttcatttta    6420
atttaaaagg atctaggtga agatcctttt tgataatctc atgaccaaaa tcccttaacg   6480
tgagttttcg ttccactgag cgtcagaccc cgtagaaaag atcaaaggat cttcttgaga   6540
tccttttttt ctgcgcgtaa                                               6560
```

<210> SEQ ID NO 19
<211> LENGTH: 6560
<212> TYPE: DNA
<213> ORGANISM: Artificial Sequence
<220> FEATURE:
<223> OTHER INFORMATION: pET21 plasmid vector carrying the sequence for BSMV-CP with a point mutation at residue D101R

<400> SEQUENCE: 19

```
tctgctgctt gcaaacaaaa aaaccaccgc taccagcggt ggtttgtttg ccggatcaag        60
agctaccaac tcttttccg aaggtaactg gcttcagcag agcgcagata ccaaatactg       120
tccttctagt gtagccgtag ttaggccacc acttcaagaa ctctgtagca ccgcctacat      180
acctcgctct gctaatcctg ttaccagtgg ctgctgccag tggcgataag tcgtgtctta      240
ccgggttgga ctcaagacga tagttaccgg ataaggcgca gcggtcgggc tgaacggggg      300
gttcgtgcac acagcccagc ttggagcgaa cgacctacac cgaactgaga tacctacagc      360
gtgagctatg agaaagcgcc acgcttcccg aagggagaaa ggcggacagg tatccggtaa      420
gcggcagggt cggaacagga gagcgcacga gggagcttcc aggggaaac gcctggtatc       480
tttatagtcc tgtcgggttt cgccacctct gacttgagcg tcgattttg tgatgctcgt       540
caggggggcg gagcctatgg aaaaacgcca gcaacgcggc cttttacgg ttcctggcct       600
tttgctggcc ttttgctcac atgttctttc ctgcgttatc ccctgattct gtggataacc      660
gtattaccgc ctttgagtga gctgataccg ctcgccgcag ccgaacgacc gagcgcagcg      720
agtcagtgag cgaggaagcg gaagagcgcc tgatgcggta ttttctcctt acgcatctgt      780
gcggtatttc acaccgcaat ggtgcactct cagtacaatc tgctctgatg ccgcatagtt      840
aagccagtat acactccgct atcgctacgt gactgggtca tggctgcgcc ccgacacccg      900
ccaacacccg ctgacgcgcc ctgacgggct tgtctgctcc cggcatccgc ttacagacaa      960
gctgtgaccg tctccgggag ctgcatgtgt cagaggtttt caccgtcatc accgaaacgc     1020
gcgaggcagc tgcggtaaag ctcatcagcg tggtcgtgaa gcgattcaca gatgtctgcc     1080
tgttcatccg cgtccagctc gttgagtttc tccagaagcg ttaatgtctg gcttctgata     1140
aagcgggcca tgttaagggc ggttttttcc tgtttggtca ctgatgcctc cgtgtaaggg     1200
ggatttctgt tcatgggggt aatgataccg atgaaacgag agaggatgct cacgatacgg     1260
gttactgatg atgaacatgc ccggttactg gaacgttgtg agggtaaaca actggcggta     1320
tggatgcggc gggaccagag aaaaatcact cagggtcaat gccagcgctt cgttaataca     1380
gatgtaggtg ttccacaggg tagccagcag catcctgcga tgcagatccg gaacataatg     1440
gtgcagggcg ctgacttccg cgtttccaga ctttacgaaa cacggaaacc gaagaccatt     1500
catgttgttg ctcaggtcgc agacgttttg cagcagcagt cgcttcacgt tcgctcgcgt     1560
atcggtgatt cattctgcta accagtaagg caaccccgcc agcctagccg ggtcctcaac     1620
gacaggagca cgatcatgcg cacccgtggg gccgccatgc cggcgataat ccccgccagc     1680
ctagccgggt cctcaacgac aggagcacga tcatgcgcac ccgtggggcc gccatgccgg     1740
cgataatggc ctgcttctcg ccgaaacgtt tggtggcggg accagtgacg aaggcttgag     1800
cgagggcgtg caagattccg aataccgcaa gcgacaggcc gatcatcgtc gcgctccagc     1860
gaaagcggtc ctcgccgaaa atgacccaga gcgctgccgg cacctgtcct acgagttgca     1920
tgataaagaa gacagtcata agtgcggcga cgatagtcat gccccgcgcc caccggaagg     1980
agctgactgg gttgaaggct ctcaagggca tcggtcgaga tcccggtgcc taatgagtga     2040
gctaacttac attaattgcg ttgcgctcac tgcccgcttt ccagtcggga aacctgtcgt     2100
gccagctgca ttaatgaatc ggccaacgcg cggggagagg cggtttgcgt attgggcgcc     2160
agggtggttt tcttttcac cagtgagacg ggcaacagct gattgccctt caccgcctgg     2220
ccctgagaga gttgcagcaa gcggtccacg ctggtttgcc ccagcaggcg aaaatcctgt     2280
```

```
ttgatggtgg ttaacggcgg gatataacat gagctgtctt cggtatcgtc gtatcccact    2340
accgagatat ccgcaccaac gcgcagcccg gactcggtaa tggcgcgcat tgcgcccagc    2400
gccatctgat cgttggcaac cagcatcgca gtgggaacga tgccctcatt cagcatttgc    2460
atggtttgtt gaaaaccgga catggcactc cagtcgcctt cccgttccgc tatcggctga    2520
atttgattgc gagtgagata tttatgccag ccagccagac gcagacgcgc cgagacagaa    2580
cttaatgggc ccgctaacag cgcgatttgc tggtgaccca atgcgaccag atgctccacg    2640
cccagtcgcg taccgtcttc atgggagaaa ataatactgt tgatgggtgt ctggtcagag    2700
acatcaagaa ataacgccgg aacattagtg caggcagctt ccacagcaat ggcatcctgg    2760
tcatccagcg gatagttaat gatcagccca ctgacgcgtt gcgcgagaag attgtgcacc    2820
gccgctttac aggcttcgac gccgcttcgt tctaccatcg acaccaccac gctggcaccc    2880
agttgatcgg cgcgagattt aatcgccgcg acaatttgcg acggcgcgtg cagggccaga    2940
ctggaggtgg caacgccaat cagcaacgac tgtttgcccg ccagttgttg tgccacgcgg    3000
ttgggaatgt aattcagctc cgccatcgcc gcttccactt tttcccgcgt tttcgcagaa    3060
acgtggctgg cctggttcac cacgcgggaa acggtctgat aagagacacc ggcatactct    3120
gcgacatcgt ataacgttac tggttttcaca ttcaccaccc tgaattgact ctcttccggg    3180
cgctatcatg ccataccgcg aaaggttttg cgccattcga tggtgtccgg gatctcgacg    3240
ctctccctta tgcgactcct gcattaggaa gcagcccagt agtaggttga ggccgttgag    3300
caccgccgcc gcaaggaatg gtgcatgcaa ggagatggcg cccaacagtc ccccggccac    3360
ggggcctgcc accatacccca cgccgaaaca agcgctcatg agcccgaagt ggcgagcccg    3420
atcttcccca tcggtgatgt cggcgatata ggcgccagca ccgcacctg tggcgccggt    3480 gatgccggcc acgatgcgtc cggcgtagag gatcgagatc tcgatcccgc gaaattaata    3540
cgactcacta tagggggaatt gtgagcggat aacaattccc ctctagaaat aattttgttt    3600
aactttaaga aggagatata catatgatgc ccaacgtatc actgacagcg aaaggggggag    3660 gtcattacat cgaagatcag tgggatacgc aagtcgtcga agcaggagtg ttcgacgact    3720
ggtgggtgca tgtagaggcc tggaataagt ttcttgacaa tctgcgcggc atcaattttt    3780
ccgtcgccag cagtcgctca caagtagcag agtatttggc tgctttggat cgtgaccttc    3840
cggctgacgt tgatcgtcgt ttcgcgggtg cacgtggtca atcggcagc cccaattact    3900 taccagcacc taaattttt cgtcttcgta acgtacaat cgctgaattg acacgtttgt    3960
cgcgcttgac ggatcagccc cacaacaatc gtgatatcga gttaaatcgc gcaaaacgcg    4020
caacaacaaa tcctagccca cctgctcaag ccccgagcga aaaccttaca ctgcgcgacg    4080 tgcaacccctt aaaggactcc gcgttacatt atcagtatgt ccttattgat cttcagtccg    4140
cacgcttgcc tgtgtatacc cgcaagactt tcgagcgcga gctggctctg gagtggatca    4200
ttccagatgc agaggaagca taaaccggtt ttaaatatgt cttacagtat cactactcca    4260
tctcagttcg tgttcttgtc atcagcgtgg gccgacccaa tagagttaat taatttatgt    4320
actaatgcct taggaaatca gtttcaaaca caacaagctc gaactgtcgt tcaaagacaa    4380
ttcagtgagg tgtggaaacc ttcaccacaa gtaactgtta ggttccctga cagtgacttt    4440
aaggtgtaca ggtacaatgc ggtattagac ccgctagtca cagcactgtt aggtgcattc    4500
gacactagaa atagaataat agaagttgaa aatcaggcga accccacgac tgccgaaacg    4560
ttagatgcta ctcgtagagt agacgacgca acggtgccca taggagcgc gataaataat    4620 ttaatagtag aattgatcag aggaaccgga tcttataatc ggagctcttt cgagagctct    4680
```

```
tctggtttgg tttggacctc tggtcctgca acttgatagt ccggacctgc aggacgcgtg    4740
tcgatcgagc accaccacca ccaccactga gatccggctg ctaacaaagc ccgaaaggaa    4800
gctgagttgg ctgctgccac cgctgagcaa taactagcat aaccccttgg ggcctctaaa    4860
cgggtcttga ggggttttt gctgaaagga ggaactatat ccggattggc gaatgggacg    4920
cgccctgtag cggcgcatta agcgcggcgg gtgtggtggt tacgcgcagc gtgaccgcta    4980
cacttgccag cgccctagcg cccgctcctt tcgctttctt ccttcctttt ctcgccacgt    5040
tcgccggctt tccccgtcaa gctctaaatc gggggctccc tttagggttc cgatttagtg    5100
ctttacggca cctcgacccc aaaaaacttg attagggtga tggttcacgt agtgggccat    5160
cgccctgata cacggttttt cgccctttga cgttggagtc cacgttcttt aatagtggac    5220
tcttgttcca aactggaaca acactcaacc ctatctcggt ctattctttt gatttataag    5280
ggattttgcc gatttcggcc tattggttaa aaatgagct gatttaacaa aaatttaacg    5340
cgaattttaa caaatatta acgcttacaa tttaggtggc acttttcggg gaaatgtgcg    5400
cggaacccct atttgtttat ttttctaaat acattcaaat atgtatccgc tcatgagaca    5460
ataaccctga taaatgcttc aataatattg aaaaaggaag agtatgagta ttcaacattt    5520
ccgtgtcgcc cttattccct ttttgcggc attttgcctt cctgttttg ctcacccaga    5580 aacgctggtg aaagtaaaag atgctgaaga tcagttgggt gcacgagtgg gttacatcga    5640
actggatctc aacagcggta agatccttga gagttttcgc cccgaagaac gttttccaat    5700
gatgagcact tttaaagttc tgctatgtgg cgcggtatta tcccgtattg acgccgggca    5760
agagcaactc ggtcgccgca tacactattc tcagaatgac ttggttgagt actcaccagt    5820
cacagaaaag catcttacgg atggcatgac agtaagagaa ttatgcagtg ctgccataac    5880
catgagtgat aacactgcgg ccaacttact tctgacaacg atcggaggac cgaaggagct    5940
aaccgctttt ttgcacaaca tgggggatca tgtaactcgc cttgatcgtt gggaaccgga    6000
gctgaatgaa gccataccaa acgacgagcg tgacaccacg atgcctgcag caatggcaac    6060
aacgttgcgc aaactattaa ctggcgaact acttactcta gcttcccggc aacaattaat    6120
agactggatg gaggcggata agttgcagg accacttctg cgctcggccc ttccggctgg    6180
ctggtttatt gctgataaat ctggagccgg tgagcgtggg tctcgcggta tcattgcagc    6240
actggggcca gatggtaagc cctcccgtat cgtagttatc tacacgacgg ggagtcaggc    6300
aactatggat gaacgaaata gacagatcgc tgagataggt gcctcactga ttaagcattg    6360
gtaactgtca gaccaagttt actcatatat actttagatt gatttaaaac ttcatttta    6420 atttaaaagg atctaggtga agatcctttt tgataatctc atgaccaaaa tcccttaacg    6480
tgagttttcg ttccactgag cgtcagaccc cgtagaaaag atcaaggat cttcttgaga    6540 tccttttttt ctgcgcgtaa                                                6560
```

<210> SEQ ID NO 20
<211> LENGTH: 6560
<212> TYPE: DNA
<213> ORGANISM: Artificial Sequence
<220> FEATURE:
<223> OTHER INFORMATION: pET21 plasmid vector carrying the sequence for
      BSMV-CP with a point mutation at residue E37Q

<400> SEQUENCE: 20

```
tctgctgctt gcaaacaaaa aaaccaccgc taccagcggt ggtttgtttg ccggatcaag    60
agctaccaac tcttttccg aaggtaactg gcttcagcag agcgcagata ccaaatactg    120
```

```
tccttctagt gtagccgtag ttaggccacc acttcaagaa ctctgtagca ccgcctacat      180
acctcgctct gctaatcctg ttaccagtgg ctgctgccag tggcgataag tcgtgtctta      240
ccgggttgga ctcaagacga tagttaccgg ataaggcgca gcggtcgggc tgaacggggg      300
gttcgtgcac acagcccagc ttggagcgaa cgacctacac cgaactgaga tacctacagc      360
gtgagctatg agaaagcgcc acgcttcccg aagggagaaa ggcggacagg tatccggtaa      420
gcggcagggt cggaacagga gagcgcacga gggagcttcc aggggggaaac gcctggtatc      480 tttatagtcc tgtcgggttt cgccacctct gacttgagcg tcgattttttg tgatgctcgt      540 caggggggcg gagcctatgg aaaaacgcca gcaacgcggc cttttttacgg ttcctggcct      600 tttgctggcc ttttgctcac atgttctttc ctgcgttatc ccctgattct gtggataacc      660
gtattaccgc ctttgagtga gctgataccg ctcgccgcag ccgaacgacc gagcgcagcg      720
agtcagtgag cgaggaagcg gaagagcgcc tgatgcggta ttttctcctt acgcatctgt      780
gcggtatttc acaccgcaat ggtgcactct cagtacaatc tgctctgatg ccgcatagtt      840
aagccagtat acactccgct atcgctacgt gactgggtca tggctgcgcc ccgacacccg      900
ccaacacccg ctgacgcgcc ctgacgggct tgtctgctcc cggcatccgc ttacagacaa      960
gctgtgaccg tctccgggag ctgcatgtgt cagaggtttt caccgtcatc accgaaacgc     1020
gcgaggcagc tgcggtaaag ctcatcagcg tggtcgtgaa gcgattcaca gatgtctgcc     1080
tgttcatccg cgtccagctc gttgagtttc tccagaagcg ttaatgtctg gcttctgata     1140
aagcgggcca tgttaagggc ggttttttcc tgtttggtca ctgatgcctc cgtgtaaggg     1200
ggatttctgt tcatgggggt aatgataccg atgaaacgag agaggatgct cacgatacgg     1260
gttactgatg atgaacatgc ccggttactg gaacgttgtg agggtaaaca actggcggta     1320
tggatgcggc gggaccagag aaaaatcact cagggtcaat gccagcgctt cgttaataca     1380
gatgtaggtg ttccacaggg tagccagcag catcctgcga tgcagatccg gaacataatg     1440
gtgcagggcg ctgacttccg cgtttccaga ctttacgaaa cacggaaacc gaagaccatt     1500
catgttgttg ctcaggtcgc agacgttttg cagcagcagt cgcttcacgt tcgctcgcgt     1560
atcggtgatt cattctgcta accagtaagg caaccccgcc agcctagccg ggtcctcaac     1620
gacaggagca cgatcatgcg cacccgtggg gccgccatgc cggcgataat ccccgccagc     1680
ctagccgggt cctcaacgac aggagcacga tcatgcgcac ccgtggggcc gccatgccgg     1740
cgataatggc ctgcttctcg ccgaaacgtt tggtggcggg accagtgacg aaggcttgag     1800
cgagggcgtg caagattccg aataccgcaa gcgacaggcc gatcatcgtc gcgctccagc     1860
gaaagcggtc ctcgccgaaa atgacccaga gcgctgccgg cacctgtcct acgagttgca     1920
tgataaagaa gacagtcata agtgcggcga cgatagtcat gccccgcgcc caccggaagg     1980
agctgactgg gttgaaggct ctcaagggca tcggtcgaga tcccggtgcc taatgagtga     2040
gctaacttac attaattgcg ttgcgctcac tgcccgcttt ccagtcggga aacctgtcgt     2100
gccagctgca ttaatgaatc ggccaacgcg cggggagagg cggtttgcgt attgggcgcc     2160
agggtggttt ttcttttcac cagtgagacg ggcaacagct gattgccctt caccgcctgg     2220
ccctgagaga gttgcagcaa gcggtccacg ctggtttgcc ccagcaggcg aaaatcctgt     2280
ttgatggtgg ttaacggcgg gatataacat gagctgtctt cggtatcgtc gtatcccact     2340
accgagatat ccgcaccaac gcgcagcccg gactcggtaa tggcgcgcat tgcgcccagc     2400
gccatctgat cgttggcaac cagcatcgca gtgggaacga tgccctcatt cagcatttgc     2460
```

```
atggtttgtt gaaaaccgga catggcactc cagtcgcctt cccgttccgc tatcggctga    2520
atttgattgc gagtgagata tttatgccag ccagccagac gcagacgcgc cgagacagaa    2580
cttaatgggc ccgctaacag cgcgatttgc tggtgaccca atgcgaccag atgctccacg    2640
cccagtcgcg taccgtcttc atgggagaaa ataatactgt tgatgggtgt ctggtcagag    2700
acatcaagaa ataacgccgg aacattagtg caggcagctt ccacagcaat ggcatcctgg    2760
tcatccagcg gatagttaat gatcagccca ctgacgcgtt gcgcgagaag attgtgcacc    2820
gccgctttac aggcttcgac gccgcttcgt tctaccatcg acaccaccac gctggcaccc    2880
agttgatcgg cgcgagattt aatcgccgcg acaatttgcg acggcgcgtg cagggccaga    2940
ctggaggtgg caacgccaat cagcaacgac tgtttgcccg ccagttgttg tgccacgcgg    3000
ttgggaatgt aattcagctc cgccatcgcc gcttccactt tttcccgcgt tttcgcagaa    3060
acgtggctgg cctggttcac cacgcgggaa acggtctgat aagagacacc ggcatactct    3120
gcgacatcgt ataacgttac tggtttcaca ttcaccaccc tgaattgact ctcttccggg    3180
cgctatcatg ccataccgcg aaaggttttg cgccattcga tggtgtccgg gatctcgacg    3240
ctctccctta tgcgactcct gcattaggaa gcagcccagt agtaggttga ggccgttgag    3300
caccgccgcc gcaaggaatg gtgcatgcaa ggagatggcg cccaacagtc ccccggccac    3360
ggggcctgcc accatacccca cgccgaaaca agcgctcatg agcccgaagt ggcgagcccg    3420
atcttcccca tcggtgatgt cggcgatata ggcgccagca accgcacctg tggcgccggt    3480
gatgccggcc acgatgcgtc cggcgtagag gatcgagatc tcgatcccgc gaaattaata    3540
cgactcacta taggggaatt gtgagcggat aacaattccc ctctagaaat aattttgttt    3600
aactttaaga aggagatata catatgatgc ccaacgtatc actgacagcg aaaggggag    3660 gtcattacat cgaagatcag tgggatacgc aagtcgtcga agcaggagtg ttcgacgact    3720
ggtgggtgca tgtacaggcc tggaataagt ttcttgacaa tctgcgcggc atcaatttt    3780 ccgtcgccag cagtcgctca caagtagcag agtatttggc tgctttggat cgtgaccttc    3840
cggctgacgt tgatcgtcgt ttcgcgggtg cacgtggtca aatcggcagc cccaattact    3900
taccagcacc taaatttttt cgtcttgata acgtacaat cgctgaattg acacgtttgt    3960
cgcgcttgac ggatcagccc cacaacaatc gtgatatcga gttaaatcgc gcaaaacgcg    4020
caacaacaaa tcctagccca cctgctcaag ccccgagcga aaaccttaca ctgcgcgacg    4080
tgcaaccctt aaaggactcc gcgttacatt atcagtatgt ccttattgat cttcagtccg    4140
cacgcttgcc tgtgtatacc cgcaagactt tcgagcgcga gctggctctg gagtggatca    4200
ttccagatgc agaggaagca taaaccggtt ttaaatatgt cttacagtat cactactcca    4260
tctcagttcg tgttcttgtc atcagcgtgg gccgacccaa tagagttaat taatttatgt    4320
actaatgcct taggaaatca gtttcaaaca caacaagctc gaactgtcgt tcaaagacaa    4380
ttcagtgagg tgtggaaacc ttcaccacaa gtaactgtta ggttccctga cagtgacttt    4440
aaggtgtaca ggtacaatgc ggtattagac ccgctagtca cagcactgtt aggtgcattc    4500
gacactagaa atagaataat agaagttgaa atcaggcga accccacgac tgccgaaacg    4560
ttagatgcta ctcgtagagt agacgacgca acggtggcca taaggagcgc gataaataat    4620
ttaatagtag aattgatcag aggaaccgga tcttataatc ggagctcttt cgagagctct    4680
tctggtttgg tttggacctc tggtcctgca acttgatagt ccggacctgc aggacgcgtg    4740
tcgatcgagc accaccacca ccaccactga gatccggctg ctaacaaagc ccgaaaggaa    4800
gctgagttgg ctgctgccac cgctgagcaa taactagcat aaccccttgg ggcctctaaa    4860
```

```
cgggtcttga ggggttttt gctgaaagga ggaactatat ccggattggc gaatgggacg    4920
cgccctgtag cggcgcatta agcgcggcgg gtgtggtggt tacgcgcagc gtgaccgcta    4980
cacttgccag cgccctagcg cccgctcctt tcgctttctt cccttccttt ctcgccacgt    5040
tcgccggctt tccccgtcaa gctctaaatc ggggctccc tttagggttc cgatttagtg     5100
ctttacggca cctcgacccc aaaaaacttg attagggtga tggttcacgt agtgggccat    5160
cgccctgata gacggttttt cgccctttga cgttggagtc cacgttcttt aatagtggac    5220
tcttgttcca aactggaaca acactcaacc ctatctcggt ctattctttt gatttataag    5280
ggattttgcc gatttcggcc tattggttaa aaaatgagct gatttaacaa aaatttaacg    5340
cgaattttaa caaaatatta acgcttacaa tttaggtggc actttcgggg gaaatgtgcg    5400
cggaacccct atttgtttat ttttctaaat acattcaaat atgtatccgc tcatgagaca    5460
ataaccctga taaatgcttc aataatattg aaaaggaag agtatgagta ttcaacattt    5520
ccgtgtcgcc cttattccct tttttgcggc attttgcctt cctgttttg ctcacccaga    5580 aacgctggtg aaagtaaaag atgctgaaga tcagttgggt gcacgagtgg gttacatcga    5640
actggatctc aacagcggta agatccttga gagttttcgc cccgaagaac gttttccaat    5700
gatgagcact tttaaagttc tgctatgtgg cgcggtatta tcccgtattg acgccgggca    5760
agagcaactc ggtcgccgca tacactattc tcagaatgac ttggttgagt actcaccagt    5820
cacagaaaag catcttacgg atggcatgac agtaagagaa ttatgcagtg ctgccataac    5880
catgagtgat aacactgcgg ccaacttact tctgacaacg atcggaggac cgaaggagct    5940
aaccgctttt ttgcacaaca tgggggatca tgtaactcgc cttgatcgtt gggaaccgga    6000
gctgaatgaa gccataccaa acgacgagcg tgacaccacg atgcctgcag caatggcaac    6060
aacgttgcgc aaactattaa ctggcgaact acttactcta gcttcccggc aacaattaat    6120
agactggatg gaggcggata aagttgcagg accacttctg cgctcggccc ttccggctgg    6180
ctggtttatt gctgataaat ctggagccgg tgagcgtggg tctcgcggta tcattgcagc    6240
actggggcca gatggtaagc cctcccgtat cgtagttatc tacacgacgg ggagtcaggc    6300
aactatggat gaacgaaata gacagatcgc tgagataggt gcctcactga ttaagcattg    6360
gtaactgtca gaccaagttt actcatatat actttagatt gatttaaaac ttcatttta    6420 atttaaaagg atctaggtga agatccttt tgataatctc atgaccaaaa tcccttaacg    6480
tgagttttcg ttccactgag cgtcagaccc cgtagaaaag atcaaaggat cttcttgaga    6540 tcctttttt ctgcgcgtaa                                                  6560
```

<210> SEQ ID NO 21  
<211> LENGTH: 6560  
<212> TYPE: DNA  
<213> ORGANISM: Artificial Sequence  
<220> FEATURE:  
<223> OTHER INFORMATION: pET21 plasmid vector carrying the sequence for BSMV-CP with a point mutation at residue E37R

<400> SEQUENCE: 21

```
tctgctgctt gcaaacaaaa aaaccaccgc taccagcggt ggtttgtttg ccggatcaag     60
agctaccaac tcttttccg aaggtaactg gcttcagcag agcgcagata ccaaatactg    120
tccttctagt gtagccgtag ttaggccacc acttcaagaa ctctgtagca ccgcctacat    180
acctcgctct gctaatcctg ttaccagtgg ctgctgccag tggcgataag tcgtgtctta    240
ccgggttgga ctcaagacga tagttaccgg ataaggcgca gcggtcgggc tgaacggggg    300
```

```
gttcgtgcac acagcccagc ttggagcgaa cgacctacac cgaactgaga tacctacagc    360
gtgagctatg agaaagcgcc acgcttcccg aagggagaaa ggcggacagg tatccggtaa    420
gcggcagggt cggaacagga gagcgcacga gggagcttcc aggggaaaac gcctggtatc    480
tttatagtcc tgtcgggttt cgccacctct gacttgagcg tcgattttg tgatgctcgt     540 caggggggcg gagcctatgg aaaaacgcca gcaacgcggc cttttacgg ttcctggcct     600 tttgctggcc ttttgctcac atgttctttc ctgcgttatc ccctgattct gtggataacc    660
gtattaccgc ctttgagtga gctgataccg ctcgccgcag ccgaacgacc gagcgcagcg    720
agtcagtgag cgaggaagcg gaagagcgcc tgatgcggta ttttctcctt acgcatctgt    780
gcggtatttc acaccgcaat ggtgcactct cagtacaatc tgctctgatg ccgcatagtt    840
aagccagtat acactccgct atcgctacgt gactgggtca tggctgcgcc ccgacacccg    900
ccaacacccg ctgacgcgcc ctgacgggct tgtctgctcc cggcatccgc ttacagacaa    960
gctgtgaccg tctccgggag ctgcatgtgt cagaggtttt caccgtcatc accgaaacgc   1020
gcgaggcagc tgcggtaaag ctcatcagcg tggtcgtgaa gcgattcaca gatgtctgcc   1080
tgttcatccg cgtccagctc gttgagtttc tccagaagcg ttaatgtctg gcttctgata   1140
aagcgggcca tgttaagggc ggttttttcc tgtttggtca ctgatgcctc cgtgtaaggg   1200
ggatttctgt tcatggggt aatgataccg atgaaacgag agaggatgct cacgatacgg    1260
gttactgatg atgaacatgc ccggttactg gaacgttgtg agggtaaaca actggcggta   1320
tggatgcggc gggaccagag aaaaatcact cagggtcaat gccagcgctt cgttaataca   1380
gatgtaggtg ttccacaggg tagccagcag catcctgcga tgcagatccg gaacataatg   1440
gtgcagggcg ctgacttccg cgtttccaga ctttacgaaa cacggaaacc gaagaccatt   1500
catgttgttg ctcaggtcgc agacgttttg cagcagcagt cgcttcacgt tcgctcgcgt   1560
atcggtgatt cattctgcta accagtaagg caaccccgcc agcctagccg ggtcctcaac   1620
gacaggagca cgatcatgcg cacccgtggg gccgccatgc cggcgataat ccccgccagc   1680
ctagccgggt cctcaacgac aggagcacga tcatgcgcac ccgtggggcc gccatgccgg   1740
cgataatggc ctgcttctcg ccgaaacgtt tggtggcggg accagtgacg aaggcttgag   1800
cgagggcgtg caagattccg aataccgcaa gcgacaggcc gatcatcgtc gcgctccagc   1860
gaaagcggtc ctcgccgaaa atgacccaga gcgctgccgg cacctgtcct acgagttgca   1920
tgataaagaa gacagtcata agtgcggcga cgatagtcat gccccgcgcc caccggaagg   1980
agctgactgg gttgaaggct ctcaagggca tcggtcgaga tcccggtgcc taatgagtga   2040
gctaacttac attaattgcg ttgcgctcac tgcccgcttt ccagtcggga acctgtcgt    2100 gccagctgca ttaatgaatc ggccaacgcg cggggagagg cggtttgcgt attgggcgcc   2160
agggtggttt ttcttttcac cagtgagacg ggcaacagct gattgccctt caccgcctgg   2220
ccctgagaga gttgcagcaa gcggtccacg ctggtttgcc ccagcaggcg aaaatcctgt   2280
ttgatggtgg ttaacggcgg gatataacat gagctgtctt cggtatcgtc gtatcccact   2340
accgagatat ccgcaccaac gcgcagcccg gactcggtaa tggcgcgcat tgcgcccagc   2400
gccatctgat cgttggcaac cagcatcgca gtgggaacga tgccctcatt cagcatttgc   2460
atggtttgtt gaaaccgga catggcactc cagtcgcctt cccgttccgc tatcggctga    2520
atttgattgc gagtgagata tttatgccag ccagccagac gcagacgcgc cgagacagaa   2580
cttaatgggc ccgctaacag cgcgatttgc tggtgaccca atgcgaccag atgctccacg   2640
```

-continued

```
cccagtcgcg taccgtcttc atgggagaaa ataatactgt tgatgggtgt ctggtcagag    2700
acatcaagaa ataacgccgg aacattagtg caggcagctt ccacagcaat ggcatcctgg    2760
tcatccagcg gatagttaat gatcagccca ctgacgcgtt gcgcgagaag attgtgcacc    2820
gccgctttac aggcttcgac gccgcttcgt tctaccatcg acaccaccac gctggcaccc    2880
agttgatcgg cgcgagattt aatcgccgcg acaatttgcg acggcgcgtg cagggccaga    2940
ctggaggtgg caacgccaat cagcaacgac tgtttgcccg ccagttgttg tgccacgcgg    3000
ttgggaatgt aattcagctc cgccatcgcc gcttccactt tttcccgcgt tttcgcagaa    3060
acgtggctgg cctggttcac cacgcgggaa acggtctgat aagagacacc ggcatactct    3120
gcgacatcgt ataacgttac tggtttcaca ttcaccaccc tgaattgact ctcttccggg    3180
cgctatcatg ccataccgcg aaaggttttg cgccattcga tggtgtccgg gatctcgacg    3240
ctctccctta tgcgactcct gcattaggaa gcagcccagt agtaggttga ggccgttgag    3300
caccgccgcc gcaaggaatg gtgcatgcaa ggagatggcg cccaacagtc ccccggccac    3360
ggggcctgcc accatacccg cgccgaaaca agcgctcatg agcccgaagt ggcgagcccg    3420
atcttcccca tcggtgatgt cggcgatata ggcgccagca accgcacctg tggcgccggt    3480
gatgccggca acgatgcgtc cggcgtagag gatcagatc tcgatcccgc gaaattaata    3540
cgactcacta tagggaatt gtgagcggat aacaattccc ctctagaaat aattttgttt    3600
aactttaaga aggagatata catatgatgc caacgtatc actgacagcg aaaggggag    3660
gtcattacat cgaagatcag tgggatacgc aagtcgtcga agcaggagtg ttcgacgact    3720
ggtgggtgca tgtacgtgcc tggaataagt ttcttgacaa tctgcgcggc atcaattttt    3780
ccgtcgccag cagtcgctca caagtagcag agtatttggc tgctttggat cgtgaccttc    3840
cggctgacgt tgatcgtcgt ttcgcgggtg cacgtggtca aatcggcagc cccaattact    3900
taccagcacc taaattttt cgtcttgata acgtacaat cgctgaattg acacgtttgt    3960
cgcgcttgac ggatcagccc cacaacaatc gtgatatcga gttaaatcgc gcaaaacgcg    4020
caacaacaaa tcctagccca cctgctcaag ccccgagcga aaaccttaca ctgcgcgacg    4080
tgcaaccctt aaaggactcc gcgttacatt atcagtatgt ccttattgat cttcagtccg    4140
cacgcttgcc tgtgtatacc cgcaagactt tcgagcgcga gctggctctg gagtggatca    4200
ttccagatgc agaggaagca taaaccggtt ttaaatatgt cttacagtat cactactcca    4260
tctcagttcg tgttcttgtc atcagcgtgg gccgacccaa tagagttaat taatttatgt    4320
actaatgcct taggaaatca gtttcaaaca caacaagctc gaactgtcgt tcaaagacaa    4380
ttcagtgagg tgtggaaacc ttcaccacaa gtaactgtta ggttccctga cagtgacttt    4440
aaggtgtaca ggtacaatgc ggtattagac ccgctagtca cagcactgtt aggtgcattc    4500
gacactagaa atagaataat agaagttgaa aatcaggcga accccacgac tgccgaaacg    4560
ttagatgcta ctcgtagagt agacgacgca acggtggcca taaggagcgc gataaataat    4620
ttaatagtag aattgatcag aggaaccgga tcttataatc ggagctcttt cgagagctct    4680
tctggtttgg tttggaccctc tggtcctgca acttgatagt ccggacctgc aggacgcgtg    4740
tcgatcgagc accaccacca ccaccactga gatccggctg ctaacaaagc ccgaaaggaa    4800
gctgagttgg ctgctgccac cgctgagcaa taactagcat aaccccttgg ggcctctaaa    4860
cgggtcttga ggggttttt gctgaaagga ggaactatat ccggattggc gaatgggacg    4920
cgccctgtag cggcgcatta agcgcggcgg gtgtggtggt tacgcgcagc gtgaccgcta    4980
cacttgccag cgccctagcg cccgctcctt tcgctttctt cccttccttt ctcgccacgt    5040
```

```
tcgccggctt tccccgtcaa gctctaaatc gggggctccc tttagggttc cgatttagtg    5100
ctttacggca cctcgacccc aaaaaacttg attagggtga tggttcacgt agtgggccat    5160
cgccctgata gacggttttt cgcccttga cgttggagtc cacgttcttt aatagtggac     5220
tcttgttcca aactgaaaca acactcaacc ctatctcggt ctattctttt gatttataag    5280
ggattttgcc gatttcggcc tattggttaa aaaatgagct gatttaacaa aaatttaacg    5340
cgaattttaa caaatatta acgcttacaa tttaggtggc acttttcggg gaaatgtgcg      5400
cggaacccct atttgtttat ttttctaaat acattcaaat atgtatccgc tcatgagaca    5460
ataaccctga taaatgcttc aataatattg aaaaggaag agtatgagta ttcaacattt      5520
ccgtgtcgcc cttattccct tttttgcggc attttgcctt cctgttttg ctcacccaga     5580
aacgctggtg aaagtaaaag atgctgaaga tcagttgggt gcacgagtgg gttacatcga    5640
actggatctc aacagcggta agatccttga gagttttcgc cccgaagaac gttttccaat    5700
gatgagcact tttaaagttc tgctatgtgg cgcggtatta cccgtattg acgccgggca      5760
agagcaactc ggtcgccgca tacactattc tcagaatgac ttggttgagt actcaccagt    5820
cacagaaaag catcttacgg atggcatgac agtaagagaa ttatgcagtg ctgccataac    5880
catgagtgat aacactgcgg ccaacttact tctgacaacg atcggaggac cgaaggagct    5940
aaccgctttt ttgcacaaca tgggggatca tgtaactcgc cttgatcgtt gggaaccgga    6000
gctgaatgaa gccataccaa acgacgagcg tgacaccacg atgcctgcag caatggcaac    6060
aacgttgcgc aaactattaa ctggcgaact acttactcta gcttcccggc aacaattaat    6120
agactggatg gaggcggata agttgcagg accacttctg cgctcggccc ttccggctgg    6180
ctggtttatt gctgataaat ctggagccgg tgagcgtggg tctcgcggta tcattgcagc    6240
actggggcca gatggtaagc cctcccgtat cgtagttatc tacacgacgg ggagtcaggc    6300
aactatggat gaacgaaata gacagatcgc tgagataggt gcctcactga ttaagcattg    6360
gtaactgtca gaccaagttt actcatatat actttagatt gatttaaaac ttcatttta    6420
atttaaaagg atctaggtga agatccttt tgataatctc atgaccaaaa tcccttaacg    6480
tgagttttcg ttccactgag cgtcagaccc cgtagaaaag atcaaggat cttcttgaga    6540
tcctttttt ctgcgcgtaa                                                  6560
```

<210> SEQ ID NO 22
<211> LENGTH: 6560
<212> TYPE: DNA
<213> ORGANISM: Artificial Sequence
<220> FEATURE:
<223> OTHER INFORMATION: pET21 plasmid vector carrying the sequence for BSMV-CP with a point mutation at residue D101N

<400> SEQUENCE: 22

```
tctgctgctt gcaaacaaaa aaaccaccgc taccagcggt ggtttgtttg ccggatcaag      60
agctaccaac tcttttccg aaggtaactg gcttcagcag agcgcagata ccaaatactg     120
tccttctagt gtagccgtag ttaggccacc acttcaagaa ctctgtagca ccgcctacat    180
acctcgctct gctaatcctg ttaccagtgg ctgctgccag tggcgataag tcgtgtctta    240
ccgggttgga ctcaagacga tagttaccgg ataaggcgca gcggtcgggc tgaacggggg    300
gttcgtgcac acagcccagc ttggagcgaa cgacctacac cgaactgaga tacctacagc    360
gtgagctatg agaaagcgcc acgcttcccg aaggagaaa ggcggacagg tatccggtaa     420
gcggcagggt cggaacagga gagcgcacga gggagcttcc agggggaaac gcctggtatc    480
```

```
tttatagtcc tgtcgggttt cgccacctct gacttgagcg tcgattttg tgatgctcgt      540 caggggggcg gagcctatgg aaaaacgcca gcaacgcggc cttttacgg ttcctggcct      600 tttgctggcc ttttgctcac atgttctttc ctgcgttatc ccctgattct gtggataacc    660
gtattaccgc ctttgagtga gctgataccg ctcgccgcag ccgaacgacc gagcgcagcg    720
agtcagtgag cgaggaagcg gaagagcgcc tgatgcggta ttttctcctt acgcatctgt    780
gcggtatttc acaccgcaat ggtgcactct cagtacaatc tgctctgatg ccgcatagtt    840
aagccagtat acactccgct atcgctacgt gactgggtca tggctgcgcc ccgacacccg    900
ccaacacccg ctgacgcgcc ctgacgggct tgtctgctcc cggcatccgc ttacagacaa    960
gctgtgaccg tctccgggag ctgcatgtgt cagaggtttt caccgtcatc accgaaacgc    1020
gcgaggcagc tgcggtaaag ctcatcagcg tggtcgtgaa gcgattcaca gatgtctgcc    1080
tgttcatccg cgtccagctc gttgagtttc tccagaagcg ttaatgtctg gcttctgata    1140
aagcgggcca tgttaagggc ggttttttcc tgtttggtca ctgatgcctc cgtgtaaggg    1200
ggatttctgt tcatgggggt aatgataccg atgaaacgag agaggatgct cacgatacgg    1260
gttactgatg atgaacatgc ccggttactg gaacgttgtg agggtaaaca actggcggta    1320
tggatgcggc gggaccagag aaaaatcact cagggtcaat gccagcgctt cgttaataca    1380
gatgtaggtg ttccacaggg tagccagcag catcctgcga tgcagatccg gaacataatg    1440
gtgcagggcg ctgacttccg cgtttccaga ctttacgaaa cacggaaacc gaagaccatt    1500
catgttgttg ctcaggtcgc agacgttttg cagcagcagt cgcttcacgt tcgctcgcgt    1560
atcggtgatt cattctgcta accagtaagg caaccccgcc agcctagccg ggtcctcaac    1620
gacaggagca cgatcatgcg cacccgtggg gccgccatgc cggcgataat ccccgccagc    1680
ctagccgggt cctcaacgac aggagcacga tcatgcgcac ccgtggggcc gccatgccgg    1740
cgataatggc ctgcttctcg ccgaaacgtt tggtggcggg accagtgacg aaggcttgag    1800
cgagggcgtg caagattccg aataccgcaa gcgacaggcc gatcatcgtc gcgctccagc    1860
gaaagcggtc ctcgccgaaa atgacccaga gcgctgccgg cacctgtcct acgagttgca    1920
tgataaagaa gacagtcata agtgcggcga cgatagtcat gccccgcgcc caccggaagg    1980
agctgactgg gttgaaggct ctcaagggca tcggtcgaga tcccggtgcc taatgagtga    2040
gctaacttac attaattgcg ttgcgctcac tgcccgcttt ccagtcggga aacctgtcgt    2100
gccagctgca ttaatgaatc ggccaacgcg cggggagagg cggtttgcgt attgggcgcc    2160
agggtggttt ttcttttcac cagtgagacg ggcaacagct gattgccctt caccgcctgg    2220
ccctgagaga gttgcagcaa gcggtccacg ctggtttgcc ccagcaggcg aaaatcctgt    2280
ttgatggtgg ttaacggcgg gatataacat gagctgtctt cggtatcgtc gtatcccact    2340
accgagatat ccgcaccaac gcgcagcccg gactcggtaa tggcgcgcat tgcgcccagc    2400
gccatctgat cgttggcaac cagcatcgca gtgggaacga tgccctcatt cagcatttgc    2460
atggtttgtt gaaaccggga catggcactc cagtcgcctt cccgttccgc tatcggctga    2520
atttgattgc gagtgagata tttatgccag ccagccagac gcagacgcgc cgagacagaa    2580
cttaatgggc ccgctaacag cgcgatttgc tggtgaccca atgcgaccag atgctccacg    2640
cccagtcgcg taccgtcttc atgggagaaa ataatactgt tgatgggtgt ctggtcagag    2700
acatcaagaa ataacgccgg aacattagtg caggcagctt ccacagcaat ggcatcctgg    2760
tcatccagcg gatagttaat gatcagccca ctgacgcgtt gcgcgagaag attgtgcacc    2820
```

```
gccgctttac aggcttcgac gccgcttcgt tctaccatcg acaccaccac gctggcaccc    2880
agttgatcgg cgcgagattt aatcgccgcg acaatttgcg acggcgcgtg cagggccaga    2940
ctggaggtgg caacgccaat cagcaacgac tgtttgcccg ccagttgttg tgccacgcgg    3000
ttgggaatgt aattcagctc cgccatcgcc gcttccactt tttcccgcgt tttcgcagaa    3060
acgtggctgg cctggttcac cacgcgggaa acggtctgat aagagacacc ggcatactct    3120
gcgacatcgt ataacgttac tggtttcaca ttcaccaccc tgaattgact ctcttccggg    3180
cgctatcatg ccataccgcg aaaggttttg cgccattcga tggtgtccgg gatctcgacg    3240
ctctccctta tgcgactcct gcattaggaa gcagcccagt agtaggttga ggccgttgag    3300
caccgccgcc gcaaggaatg gtgcatgcaa ggagatggcg cccaacagtc ccccggccac    3360
ggggcctgcc accatacccca cgccgaaaca agcgctcatg agcccgaagt ggcgagcccg    3420
atcttcccca tcggtgatgt cggcgatata ggcgccagca accgcacctg tggcgccggt    3480
gatgccggcc acgatgcgtc cggcgtagag gatcgagatc tcgatcccgc gaaattaata    3540
cgactcacta tagggaatt gtgagcggat aacaattccc ctctagaaat aattttgttt    3600
aactttaaga aggagatata catatgatgc ccaacgtatc actgacagcg aaagggggag    3660
gtcattacat cgaagatcag tgggatacgc aagtcgtcga agcaggagtg ttcgacgact    3720
ggtgggtgca tgtagaggcc tggaataagt ttcttgacaa tctgcgcggc atcaattttt    3780
ccgtcgccag cagtcgctca caagtagcag agtatttggc tgctttggat cgtgaccttc    3840
cggctgacgt tgatcgtcgt ttcgcgggtg cacgtggtca aatcggcagc cccaattact    3900
taccagcacc taaatttttt cgtcttaata acgtacaat cgctgaattg acacgtttgt    3960
cgcgcttgac ggatcagccc cacaacaatc gtgatatcga gttaaatcgc gcaaaacgcg    4020
caacaacaaa tcctagccca cctgctcaag ccccgagcga aaaccttaca ctgcgcgacg    4080 tgcaacccctt aaaggactcc gcgttacatt atcagtatgt ccttattgat cttcagtccg    4140
cacgcttgcc tgtgtatacc cgcaagactt tcgagcgcga gctggctctg gagtggatca    4200
ttccagatgc agaggaagca taaaccggtt ttaaatatgt cttacagtat cactactcca    4260
tctcagttcg tgttcttgtc atcagcgtgg gccgacccaa tagagttaat taatttatgt    4320
actaatgcct taggaaatca gtttcaaaca caacaagctc gaactgtcgt tcaaagacaa    4380
ttcagtgagg tgtggaaacc ttcaccacaa gtaactgtta ggttccctga cagtgacttt    4440
aaggtgtaca ggtacaatgc ggtattagac ccgctagtca cagcactgtt aggtgcattc    4500
gacactagaa atagaataat agaagttgaa aatcaggcga accccacgac tgccgaaacg    4560
ttagatgcta ctcgtagagt agacgacgca acggtggcca taaggagcgc gataaataat    4620
ttaatagtag aattgatcag aggaaccgga tcttataatc ggagctcttt cgagagctct    4680
tctggtttgg tttggaccctc tggtcctgca acttgatagt ccggacctgc aggacgcgtg    4740
tcgatcgagc accaccacca ccaccactga gatccggctg ctaacaaagc ccgaaaggaa    4800
gctgagttgg ctgctgccac cgctgagcaa taactagcat aacccccttgg ggcctctaaa    4860 cgggtcttga ggggttttttt gctgaaagga ggaactatat ccggattggc gaatgggacg    4920
cgccctgtag cggcgcatta gcgcggcgg gtgtggtggt tacgcgcagc gtgaccgcta    4980
cacttgccag cgccctagcg cccgctcctt tcgctttctt cccttccttt ctcgccacgt    5040
tcgccggctt tccccgtcaa gctctaaatc ggggggctccc tttagggttc gatttagtg    5100 ctttacggca cctcgacccc aaaaaacttg attagggtga tggttcacgt agtgggccat    5160
cgccctgata gacggttttt cgccctttga cgttggagtc cacgttcttt aatagtggac    5220
```

```
tcttgttcca aactggaaca acactcaacc ctatctcggt ctattctttt gatttataag    5280
ggattttgcc gatttcggcc tattggttaa aaaatgagct gatttaacaa aaatttaacg    5340
cgaattttaa caaaatatta acgcttacaa tttaggtggc acttttcggg gaaatgtgcg    5400
cggaacccct atttgtttat ttttctaaat acattcaaat atgtatccgc tcatgagaca    5460
ataaccctga taaatgcttc aataatattg aaaaaggaag agtatgagta ttcaacattt    5520
ccgtgtcgcc cttattccct ttttttgcggc attttgcctt cctgttttttg ctcacccaga    5580 aacgctggtg aaagtaaaag atgctgaaga tcagttgggt gcacgagtgg gttacatcga    5640
actggatctc aacagcggta agatccttga gagttttcgc cccgaagaac gttttccaat    5700
gatgagcact tttaaagttc tgctatgtgg cgcggtatta cccgtattg acgccgggca    5760 agagcaactc ggtcgccgca tacactattc tcagaatgac ttggttgagt actcaccagt    5820
cacagaaaag catcttacgg atggcatgac agtaagagaa ttatgcagtg ctgccataac    5880
catgagtgat aacactgcgg ccaacttact tctgacaacg atcggaggac cgaaggagct    5940
aaccgctttt ttgcacaaca tgggggatca tgtaactcgc cttgatcgtt gggaaccgga    6000
gctgaatgaa gccataccaa acgacgagcg tgacaccacg atgcctgcag caatggcaac    6060
aacgttgcgc aaactattaa ctggcgaact acttactcta gcttcccggc aacaattaat    6120
agactggatg gaggcggata aagttgcagg accacttctg cgctcggccc ttccggctgg    6180
ctggtttatt gctgataaat ctggagccgg tgagcgtggg tctcgcggta tcattgcagc    6240
actggggcca gatggtaagc cctcccgtat cgtagttatc tacacgacgg ggagtcaggc    6300
aactatggat gaacgaaata gacagatcgc tgagataggt gcctcactga ttaagcattg    6360
gtaactgtca gaccaagttt actcatatat actttagatt gatttaaaac ttcattttta    6420
atttaaaagg atctaggtga agatcctttt tgataatctc atgaccaaaa tcccttaacg    6480
tgagttttcg ttccactgag cgtcagaccc cgtagaaaag atcaaaggat cttcttgaga    6540 tcctttttttt ctgcgcgtaa                                                6560
```

<210> SEQ ID NO 23
<211> LENGTH: 6560
<212> TYPE: DNA
<213> ORGANISM: Artificial Sequence
<220> FEATURE:
<223> OTHER INFORMATION: pET21 plasmid vector carrying the sequence for BSMV-CP having a point mutation at residue E62Q
<400> SEQUENCE: 23

```
tctgctgctt gcaaacaaaa aaaccaccgc taccagcggt ggtttgtttg ccggatcaag      60
agctaccaac tcttttttccg aaggtaactg gcttcagcag agcgcagata ccaaatactg    120
tccttctagt gtagccgtag ttaggccacc acttcaagaa ctctgtagca ccgcctacat    180
acctcgctct gctaatcctg ttaccagtgg ctgctgccag tggcgataag tcgtgtctta    240
ccgggttgga ctcaagacga tagttaccgg ataaggcgca gcggtcgggc tgaacggggg    300
gttcgtgcac acagcccagc ttggagcgaa cgacctacac cgaactgaga tacctacagc    360
gtgagctatg agaaagcgcc acgcttcccg aagggagaaa ggcggacagg tatccggtaa    420
gcggcagggt cggaacagga gagcgcacga gggagcttcc agggggaaac gcctggtatc    480
tttatagtcc tgtcgggttt cgccacctct gacttgagcg tcgatttttg tgatgctcgt    540
caggggggcg gagcctatgg aaaaacgcca gcaacgcggc cttttacgg ttcctggcct    600 tttgctggcc ttttgctcac atgttctttc ctgcgttatc ccctgattct gtggataacc    660
```

```
gtattaccgc ctttgagtga gctgataccg ctcgccgcag ccgaacgacc gagcgcagcg      720
agtcagtgag cgaggaagcg gaagagcgcc tgatgcggta ttttctcctt acgcatctgt      780
gcggtatttc acaccgcaat ggtgcactct cagtacaatc tgctctgatg ccgcatagtt      840
aagccagtat acactccgct atcgctacgt gactgggtca tggctgcgcc ccgacacccg      900
ccaacacccg ctgacgcgcc ctgacgggct tgtctgctcc cggcatccgc ttacagacaa      960
gctgtgaccg tctccgggag ctgcatgtgt cagaggtttt caccgtcatc accgaaacgc     1020
gcgaggcagc tgcggtaaag ctcatcagcg tggtcgtgaa gcgattcaca gatgtctgcc     1080
tgttcatccg cgtccagctc gttgagtttc tccagaagcg ttaatgtctg gcttctgata     1140
aagcgggcca tgttaagggc ggttttttcc tgtttggtca ctgatgcctc cgtgtaaggg     1200
ggatttctgt tcatgggggt aatgataccg atgaaacgag agaggatgct cacgatacgg     1260
gttactgatg atgaacatgc ccggttactg gaacgttgtg agggtaaaca actggcggta     1320
tggatgcggc gggaccagag aaaaatcact cagggtcaat gccagcgctt cgttaataca     1380
gatgtaggtg ttccacaggg tagccagcag catcctgcga tgcagatccg aacataatg      1440 gtgcagggcg ctgacttccg cgtttccaga ctttacgaaa cacggaaacc gaagaccatt     1500
catgttgttg ctcaggtcgc agacgttttg cagcagcagt cgcttcacgt tcgctcgcgt     1560
atcggtgatt cattctgcta accagtaagg caaccccgcc agcctagccg ggtcctcaac     1620
gacaggagca cgatcatgcg cacccgtggg gccgccatgc cggcgataat ccccgccagc     1680
ctagccgggt cctcaacgac aggagcacga tcatgcgcac ccgtggggcc gccatgccgg     1740
cgataatggc ctgcttctcg ccgaaacgtt tggtggcggg accagtgacg aaggcttgag     1800
cgagggcgtg caagattccg aataccgcaa gcgacaggcc gatcatcgtc gcgctccagc     1860
gaaagcggtc ctcgccgaaa atgacccaga gcgctgccgg cacctgtcct acgagttgca     1920
tgataaagaa gacagtcata agtgcggcga cgatagtcat gccccgcgcc caccggaagg     1980
agctgactgg gttgaaggct ctcaagggca tcggtcgaga tcccggtgcc taatgagtga     2040
gctaacttac attaattgcg ttgcgctcac tgcccgcttt ccagtcggga aacctgtcgt     2100
gccagctgca ttaatgaatc ggccaacgcg cggggagagg cggtttgcgt attgggcgcc     2160
agggtggttt ttcttttcac cagtgagacg ggcaacagct gattgccctt caccgcctgg     2220
ccctgagaga gttgcagcaa gcggtccacg ctggtttgcc ccagcaggcg aaaatcctgt     2280
ttgatggtgg ttaacggcgg gatataacat gagctgtctt cggtatcgtc gtatcccact     2340
accgagatat ccgcaccaac gcgcagcccg gactcggtaa tggcgcgcat gcgcccagc      2400 gccatctgat cgttggcaac cagcatcgca gtgggaacga tgccctcatt cagcatttgc     2460
atggtttgtt gaaaaccgga catggcactc cagtcgcctt cccgttccgc tatcggctga     2520
atttgattgc gagtgagata tttatgccag ccagccagac gcagacgcgc cgagacagaa     2580
cttaatgggc ccgctaacag cgcgatttgc tggtgaccca atgcgaccag atgctccacg     2640
cccagtcgcg taccgtcttc atgggagaaa ataatactgt tgatgggtgt ctggtcagag     2700
acatcaagaa ataacgccgg aacattagtg caggcagctt ccacagcaat ggcatcctgg     2760
tcatccagcg gatagttaat gatcagccca ctgacgcgtt gcgcgagaag attgtgcacc     2820
gccgctttac aggcttcgac gccgcttcgt tctaccatcg acaccaccac gctggcaccc     2880
agttgatcgg cgcgagattt aatcgccgcg acaatttgcg acggcgcgtg cagggccaga     2940
ctggaggtgg caacgccaat cagcaacgac tgtttgcccg ccagttgttg tgccacgcgg     3000
```

```
ttgggaatgt aattcagctc cgccatcgcc gcttccactt tttcccgcgt tttcgcagaa   3060
acgtggctgg cctggttcac cacgcgggaa acggtctgat aagagacacc ggcatactct   3120
gcgacatcgt ataacgttac tggtttcaca ttcaccaccc tgaattgact ctcttccggg   3180
cgctatcatg ccataccgcg aaaggttttg cgccattcga tggtgtccgg gatctcgacg   3240
ctctccctta tgcgactcct gcattaggaa gcagcccagt agtaggttga ggccgttgag   3300
caccgccgcc gcaaggaatg gtgcatgcaa ggagatggcg cccaacagtc ccccggccac   3360
ggggcctgcc accatacccac gccgaaaca agcgctcatg agcccgaagt ggcgagcccg   3420
atcttcccca tcggtgatgt cggcgatata ggcgccagca accgcacctg tggcgccggt   3480
gatgccggcc acgatgcgtc cggcgtagag gatcgagatc tcgatcccgc gaaattaata   3540
cgactcacta tagggaatt gtgagcggat aacaattccc ctctagaaat aattttgttt   3600
aactttaaga aggagatata catatgatgc ccaacgtatc actgacagcg aaaggggag   3660
gtcattacat cgaagatcag tgggatacgc aagtcgtcga agcaggagtg ttcgacgact   3720
ggtgggtgca tgtagaggcc tggaataagt ttcttgacaa tctgcgcggc atcaattttt   3780
ccgtcgccag cagtcgctca caagtagcac agtatttggc tgctttggat cgtgaccttc   3840
cggctgacgt tgatcgtcgt ttcgcgggtg cacgtggtca aatcggcagc cccaattact   3900
taccagcacc taaattttt cgtcttgata aacgtacaat cgctgaattg acacgtttgt   3960
cgcgcttgac ggatcagccc cacaacaatc gtgatatcga gttaaatcgc gcaaaacgcg   4020
caacaacaaa tcctagccca cctgctcaag ccccgagcga aaaccttaca ctgcgcgacg   4080
tgcaacccctt aaaggactcc gcgttacatt atcagtatgt ccttattgat cttcagtccg   4140
cacgcttgcc tgtgtatacc cgcaagactt tcgagcgcga gctggctctg gagtggatca   4200
ttccagatgc agaggaagca taaaccggtt ttaaatatgt cttacagtat cactactcca   4260
tctcagttcg tgttcttgtc atcagcgtgg gccgacccaa tagagttaat taatttatgt   4320
actaatgcct taggaaatca gtttcaaaca caacaagctc gaactgtcgt tcaaagacaa   4380
ttcagtgagg tgtggaaacc ttcaccacaa gtaactgtta ggttccctga cagtgacttt   4440
aaggtgtaca ggtacaatgc ggtattagac ccgctagtca cagcactgtt aggtgcattc   4500
gacactagaa atagaataat agaagttgaa aatcaggcga accccacgac tgccgaaacg   4560
ttagatgcta ctcgtagagt agacgacgca acggtggcca taaggagcgc gataaataat   4620
ttaatagtag aattgatcag aggaaccgga tcttataatc ggagctcttt cgagagctct   4680
tctggtttgg tttggacctc tggtcctgca acttgatagt ccggacctgc aggacgcgtg   4740
tcgatcgagc accaccacca ccaccactga gatccggctg ctaacaaagc ccgaaggaa   4800
gctgagttgg ctgctgccac cgctgagcaa taactagcat aaccccttgg ggcctctaaa   4860
cgggtcttga ggggtttttt gctgaaagga ggaactatat ccggattggc gaatgggacg   4920
cgccctgtag cggcgcatta gcgcggcgg gtgtggtggt tacgcgcagc gtgaccgcta   4980
cacttgccag cgccctagcg cccgctcctt tcgctttctt cccttccttt ctcgccacgt   5040
tcgccggctt tccccgtcaa gctctaaatc ggggctccc tttagggttc gatttagtg   5100
ctttacggca cctcgacccc aaaaaacttg attagggtga tggttcacgt agtgggccat   5160
cgccctgata gacggttttt cgccctttga cgttggagtc cacgttcttt aatagtggac   5220
tcttgttcca aactgaaaca acactcaacc ctatctcggt ctattctttt gatttataag   5280
ggattttgcc gatttcggcc tattggttaa aaaatgagct gatttaacaa aaatttaacg   5340
cgaattttaa caaaatatta acgcttacaa tttaggtggc acttttcggg gaaatgtgcg   5400
```

```
cggaacccct atttgtttat ttttctaaat acattcaaat atgtatccgc tcatgagaca     5460
ataaccctga taaatgcttc aataatattg aaaaaggaag agtatgagta ttcaacattt     5520
ccgtgtcgcc cttattccct tttttgcggc attttgcctt cctgtttttg ctcacccaga     5580
aacgctggtg aaagtaaaag atgctgaaga tcagttgggt gcacgagtgg gttacatcga     5640
actggatctc aacagcggta agatccttga gagttttcgc cccgaagaac gttttccaat     5700
gatgagcact tttaaagttc tgctatgtgg cgcggtatta tcccgtattg acgccgggca     5760
agagcaactc ggtcgccgca tacactattc tcagaatgac ttggttgagt actcaccagt     5820
cacagaaaag catcttacgg atggcatgac agtaagagaa ttatgcagtg ctgccataac     5880
catgagtgat aacactgcgg ccaacttact tctgacaacg atcggaggac cgaaggagct     5940
aaccgctttt ttgcacaaca tgggggatca tgtaactcgc cttgatcgtt gggaaccgga     6000
gctgaatgaa gccataccaa acgacgagcg tgacaccacg atgcctgcag caatggcaac     6060
aacgttgcgc aaactattaa ctggcgaact acttactcta gcttcccggc aacaattaat     6120
agactggatg gaggcggata agttgcagg accacttctg cgctcggccc ttccggctgg     6180
ctggtttatt gctgataaat ctggagccgg tgagcgtggg tctcgcggta tcattgcagc     6240
actggggcca gatggtaagc cctcccgtat cgtagttatc tacacgacgg ggagtcaggc     6300
aactatggat gaacgaaata gacagatcgc tgagataggt gcctcactga ttaagcattg     6360
gtaactgtca gaccaagttt actcatatat actttagatt gatttaaaac ttcatttta     6420 atttaaaagg atctaggtga agatcctttt tgataatctc atgaccaaaa tcccttaacg     6480
tgagttttcg ttccactgag cgtcagaccc cgtagaaaag atcaaaggat cttcttgaga     6540 tcctttttt ctgcgcgtaa                                                 6560
```

<210> SEQ ID NO 24
<211> LENGTH: 6560
<212> TYPE: DNA
<213> ORGANISM: Artificial Sequence
<220> FEATURE:
<223> OTHER INFORMATION: pET21 plasmid vector carrying the sequence for
      BSMV-CP having a point mutation at both residues E62Q and D101N

<400> SEQUENCE: 24

```
tctgctgctt gcaaacaaaa aaaccaccgc taccagcggt ggtttgtttg ccggatcaag     60
agctaccaac tcttttttccg aaggtaactg gcttcagcag agcgcagata ccaaatactg     120
tccttctagt gtagccgtag ttaggccacc acttcaagaa ctctgtagca ccgcctacat     180
acctcgctct gctaatcctg ttaccagtgg ctgctgccag tggcgataag tcgtgtctta     240
ccgggttgga ctcaagacga tagttaccgg ataaggcgca gcggtcgggc tgaacggggg     300
gttcgtgcac acagcccagc ttggagcgaa cgacctacac cgaactgaga tacctacagc     360
gtgagctatg agaaagcgcc acgcttcccg aagggagaaa ggcggacagg tatccggtaa     420
gcggcagggt cggaacagga gagcgcacga ggagcttcc aggggggaaac gcctggtatc     480 tttatagtcc tgtcgggttt cgccacctct gacttgagcg tcgatttttg tgatgctcgt     540 cagggggggcg gagcctatgg aaaaacgcca gcaacgcggc ctttttacgg ttcctggcct     600
tttgctggcc ttttgctcac atgttctttc ctgcgttatc ccctgattct gtggataacc     660
gtattaccgc ctttgagtga gctgataccg ctcgccgcag ccgaacgacc gagcgcagcg     720
agtcagtgag cgaggaagcg gaagagcgcc tgatgcggta ttttctcctt acgcatctgt     780
gcggtatttc acaccgcaat ggtgcactct cagtacaatc tgctctgatg ccgcatagtt     840
```

```
aagccagtat acactccgct atcgctacgt gactgggtca tggctgcgcc ccgacacccg    900
ccaacacccg ctgacgcgcc ctgacgggct tgtctgctcc cggcatccgc ttacagacaa    960
gctgtgaccg tctccgggag ctgcatgtgt cagaggtttt caccgtcatc accgaaacgc   1020
gcgaggcagc tgcggtaaag ctcatcagcg tggtcgtgaa gcgattcaca gatgtctgcc   1080
tgttcatccg cgtccagctc gttgagtttc tccagaagcg ttaatgtctg gcttctgata   1140
aagcgggcca tgttaagggc ggttttttcc tgtttggtca ctgatgcctc cgtgtaaggg   1200
ggatttctgt tcatgggggt aatgataccg atgaaacgag agaggatgct cacgatacgg   1260
gttactgatg atgaacatgc ccggttactg aacgttgtg agggtaaaca actggcggta   1320
tggatgcggc gggaccagag aaaaatcact cagggtcaat gccagcgctt cgttaataca   1380
gatgtaggtg ttccacaggg tagccagcag catcctgcga tgcagatccg aacataatg   1440
gtgcagggcg ctgacttccg cgtttccaga ctttacgaaa cacggaaacc gaagaccatt   1500
catgttgttg ctcaggtcgc agacgttttg cagcagcagt cgcttcacgt tcgctcgcgt   1560
atcggtgatt cattctgcta accagtaagg caaccccgcc agcctagccg ggtcctcaac   1620
gacaggagca cgatcatgcg cacccgtggg gccgccatgc cggcgataat ccccgccagc   1680
ctagccgggt cctcaacgac aggagcacga tcatgcgcac ccgtggggcc gccatgccgg   1740
cgataatggc ctgcttctcg ccgaaacgtt tggtggcggg accagtgacg aaggcttgag   1800
cgagggcgtg caagattccg aataccgcaa gcgacaggcc gatcatcgtc gcgctccagc   1860
gaaagcggtc ctcgccgaaa atgacccaga gcgctgccgg cacctgtcct acgagttgca   1920
tgataaagaa gacagtcata agtgcggcga cgatagtcat gccccgcgcc caccggaagg   1980
agctgactgg gttgaaggct ctcaagggca tcggtcgaga tcccggtgcc taatgagtga   2040
gctaacttac attaattgcg ttgcgctcac tgcccgcttt ccagtcggga aacctgtcgt   2100
gccagctgca ttaatgaatc ggccaacgcg cggggagagg cggtttgcgt attgggcgcc   2160
agggtggttt ttcttttcac cagtgagacg ggcaacagct gattgccctt caccgcctgg   2220
ccctgagaga gttgcagcaa gcggtccacg ctggtttgcc ccagcaggcg aaaatcctgt   2280
ttgatggtgg ttaacggcgg gatataacat gagctgtctt cggtatcgtc gtatcccact   2340
accgagatat ccgcaccaac gcgcagcccg gactcggtaa tggcgcgcat tgcgcccagc   2400
gccatctgat cgttggcaac cagcatcgca gtgggaacga tgccctcatt cagcatttgc   2460
atggtttgtt gaaaaccgga catggcactc cagtcgcctt cccgttccgc tatcggctga   2520
atttgattgc gagtgagata tttatgccag ccagccagac gcagacgcgc cgagacagaa   2580
cttaatgggc ccgctaacag cgcgatttgc tggtgaccca atgcgaccag atgctccacg   2640
cccagtcgcg taccgtcttc atgggagaaa ataatactgt tgatgggtgt ctggtcagag   2700
acatcaagaa ataacgccgg aacattagtg caggcagctt ccacagcaat ggcatcctgg   2760
tcatccagcg gatagttaat gatcagccca ctgacgcgtt gcgcgagaag attgtgcacc   2820
gccgctttac aggcttcgac gccgcttcgt tctaccatcg acaccaccac gctggcaccc   2880
agttgatcgg cgcgagattt aatcgccgcg acaatttgcg acggcgcgtg cagggccaga   2940
ctggaggtgg caacgccaat cagcaacgac tgtttgcccg ccagttgttg tgccacgcgg   3000
ttgggaatgt aattcagctc cgccatcgcc gcttccactt tttcccgcgt tttcgcagaa   3060
acgtggctgg cctggttcac cacgcgggaa acggtctgat aagagacacc ggcatactct   3120
gcgacatcgt ataacgttac tggtttcaca ttcaccaccc tgaattgact ctcttccggg   3180
```

```
cgctatcatg ccataccgcg aaaggttttg cgccattcga tggtgtccgg gatctcgacg      3240
ctctccctta tgcgactcct gcattaggaa gcagcccagt agtaggttga ggccgttgag      3300
caccgccgcc gcaaggaatg gtgcatgcaa ggagatggcg cccaacagtc ccccggccac      3360
ggggcctgcc accataccca cgccgaaaca agcgctcatg agcccgaagt ggcgagcccg      3420
atcttcccca tcggtgatgt cggcgatata ggcgccagca accgcacctg tggcgccggt      3480
gatgccggcc acgatgcgtc cggcgtagag gatcgagatc tcgatcccgc gaaattaata      3540
cgactcacta tagggaatt gtgagcggat aacaattccc ctctagaaat aattttgttt      3600
aactttaaga aggagatata catatgatgc ccaacgtatc actgacagcg aaaggggag      3660 gtcattacat cgaagatcag tgggatacgc aagtcgtcga agcaggagtg ttcgacgact      3720
ggtgggtgca tgtagaggcc tggaataagt ttcttgacaa tctgcgcggc atcaattttt      3780
ccgtcgccag cagtcgctca caagtagcac agtatttggc tgctttggat cgtgaccttc      3840
cggctgacgt tgatcgtcgt ttcgcgggtg cacgtggtca aatcggcagc cccaattact      3900
taccagcacc taaattttt cgtcttaata acgtacaat cgctgaattg acacgtttgt      3960
cgcgcttgac ggatcagccc cacaacaatc gtgatatcga gttaaatcgc gcaaaacgcg      4020
caacaacaaa tcctagccca cctgctcaag ccccgagcga aaaccttaca ctgcgcgacg      4080
tgcaaccctt aaaggactcc gcgttacatt atcagtatgt ccttattgat cttcagtccg      4140
cacgcttgcc tgtgtatacc cgcaagactt tcgagcgcga gctggctctg gagtggatca      4200
ttccagatgc agaggaagca taaaccggtt ttaaatatgt cttacagtat cactactcca      4260
tctcagttcg tgttcttgtc atcagcgtgg gccgacccaa tagagttaat taatttatgt      4320
actaatgcct taggaaatca gtttcaaaca caacaagctc gaactgtcgt tcaaagacaa      4380
ttcagtgagg tgtggaaacc ttcaccacaa gtaactgtta ggttccctga cagtgacttt      4440
aaggtgtaca ggtacaatgc ggtattagac ccgctagtca cagcactgtt aggtgcattc      4500
gacactagaa atagaataat agaagttgaa atcaggcga accccacgac tgccgaaacg      4560
ttagatgcta ctcgtagagt agacgacgca acggtggcca taggagcgc gataaataat      4620 ttaatagtag aattgatcag aggaaccgga tcttataatc ggagctcttt cgagagctct      4680
tctggtttgg tttggaccte tggtcctgca acttgatagt ccggacctgc aggacgcgtg      4740
tcgatcgagc accaccacca ccaccactga gatccggctg ctaacaaagc ccgaaaggaa      4800
gctgagttgg ctgctgccac cgctgagcaa taactagcat aaccccttgg ggcctctaaa      4860
cgggtcttga ggggtttttt gctgaaagga ggaactatat ccggattggc gaatgggacg      4920
cgccctgtag cggcgcatta agcgcggcgg gtgtggtggt tacgcgcagc gtgaccgcta      4980
cacttgccag cgccctagcg cccgctcctt tcgctttctt cccttccttt ctcgccacgt      5040
tcgccggctt tccccgtcaa gctctaaatc ggggctccc tttagggttc cgatttagtg      5100
ctttacggca cctcgacccc aaaaaacttg attagggtga tggttcacgt agtgggccat      5160
cgccctgata gacggttttt cgccctttga cgttggagtc cacgttcttt aatagtggac      5220
tcttgttcca aactggaaca acactcaacc ctatctcggt ctattctttt gatttataag      5280
ggattttgcc gatttcggcc tattggttaa aaaatgagct gatttaacaa aaatttaacg      5340
cgaattttaa caaaatatta cgcttacaa tttaggtggc actttcggg gaaatgtgcg      5400 cggaacccct atttgtttat ttttctaaat acattcaaat atgtatccgc tcatgagaca      5460
ataaccctga taaatgcttc aataatattg aaaaaggaag agtatgagta ttcaacattt      5520
ccgtgtcgcc tttattccct tttttgcggc attttgcctt cctgtttttg ctcacccaga      5580
```

```
aacgctggtg aaagtaaaag atgctgaaga tcagttgggt gcacgagtgg gttacatcga    5640
actggatctc aacagcggta agatccttga gagttttcgc cccgaagaac gttttccaat    5700
gatgagcact tttaaagttc tgctatgtgg cgcggtatta tcccgtattg acgccgggca    5760
agagcaactc ggtcgccgca tacactattc tcagaatgac ttggttgagt actcaccagt    5820
cacagaaaag catcttacgg atggcatgac agtaagagaa ttatgcagtg ctgccataac    5880
catgagtgat aacactgcgg ccaacttact tctgacaacg atcggaggac cgaaggagct    5940
aaccgctttt ttgcacaaca tgggggatca tgtaactcgc cttgatcgtt gggaaccgga    6000
gctgaatgaa gccataccaa acgacgagcg tgacaccacg atgcctgcag caatggcaac    6060
aacgttgcgc aaactattaa ctggcgaact acttactcta gcttcccggc aacaattaat    6120
agactggatg gaggcggata agttgcagg  accacttctg cgctcggccc ttccggctgg    6180
ctggtttatt gctgataaat ctggagccgg tgagcgtggg tctcgcggta tcattgcagc    6240
actggggcca gatggtaagc cctcccgtat cgtagttatc tacacgacgg ggagtcaggc    6300
aactatggat gaacgaaata gacagatcgc tgagataggt gcctcactga ttaagcattg    6360
gtaactgtca gaccaagttt actcatatat actttagatt gatttaaaac ttcattttta    6420
atttaaaagg atctaggtga agatccttt  tgataatctc atgaccaaaa tcccttaacg    6480
tgagttttcg ttccactgag cgtcagaccc cgtagaaaag atcaaaggat cttcttgaga    6540
tccttttttt ctgcgcgtaa                                                6560

<210> SEQ ID NO 25
<211> LENGTH: 6560
<212> TYPE: DNA
<213> ORGANISM: Artificial Sequence
<220> FEATURE:
<223> OTHER INFORMATION: pET21 plasmid vector carrying the sequence for
      wild-type BSMV-CP

<400> SEQUENCE: 25
tctgctgctt gcaaacaaaa aaaccaccgc taccagcggt ggtttgtttg ccggatcaag      60
agctaccaac tcttttccg  aaggtaactg gcttcagcag agcgcagata ccaaatactg     120
tccttctagt gtagccgtag ttaggccacc acttcaagaa ctctgtagca ccgcctacat     180
acctcgctct gctaatcctg ttaccagtgg ctgctgccag tggcgataag tcgtgtctta     240
ccgggttgga ctcaagacga tagttaccgg ataaggcgca gcggtcgggc tgaacggggg     300
gttcgtgcac acagcccagc ttggagcgaa cgacctacac cgaactgaga tacctacagc     360
gtgagctatg agaaagcgcc acgcttcccg aagggagaaa ggcggacagg tatccggtaa     420
gcggcagggt cggaacagga gagcgcacga gggagcttcc agggggaaac gcctggtatc     480
tttatagtcc tgtcgggttt cgccacctct gacttgagcg tcgatttttg tgatgctcgt     540
caggggggcg gagcctatgg aaaaacgcca gcaacgcggc cttttacgg  ttcctggcct     600 tttgctggcc ttttgctcac atgttctttc ctgcgttatc ccctgattct gtggataacc     660
gtattaccgc ctttgagtga gctgataccg ctcgccgcag ccgaacgacc gagcgcagcg     720
agtcagtgag cgaggaagcg gaagagcgcc tgatgcggta ttttctcctt acgcatctgt     780
gcggtatttc acaccgcaat ggtgcactct cagtacaatc tgctctgatg ccgcatagtt     840
aagccagtat acactccgct atcgctacgt gactgggtca tggctgcgcc ccgacacccg     900
ccaacacccg ctgacgcgcc ctgacgggct tgtctgctcc cggcatccgc ttacagacaa     960
gctgtgaccg tctccgggag ctgcatgtgt cagaggtttt caccgtcatc accgaaacgc    1020
```

```
gcgaggcagc tgcggtaaag ctcatcagcg tggtcgtgaa gcgattcaca gatgtctgcc    1080
tgttcatccg cgtccagctc gttgagtttc tccagaagcg ttaatgtctg gcttctgata    1140
aagcgggcca tgttaagggc ggttttttcc tgtttggtca ctgatgcctc cgtgtaaggg    1200
ggatttctgt tcatgggggt aatgataccg atgaaacgag agaggatgct cacgatacgg    1260
gttactgatg atgaacatgc ccggttactg aacgttgtg agggtaaaca actggcggta     1320
tggatgcggc gggaccagag aaaaatcact cagggtcaat gccagcgctt cgttaataca    1380
gatgtaggtg ttccacaggg tagccagcag catcctgcga tgcagatccg aacataatg     1440 gtgcagggcg ctgacttccg cgtttccaga ctttacgaaa cacggaaacc gaagaccatt    1500
catgttgttg ctcaggtcgc agacgttttg cagcagcagt cgcttcacgt tcgctcgcgt    1560
atcggtgatt cattctgcta accagtaagg caaccccgcc agcctagccg ggtcctcaac    1620
gacaggagca cgatcatgcg cacccgtggg gccgccatgc cggcgataat ccccgccagc    1680
ctagccgggt cctcaacgac aggagcacga tcatgcgcac ccgtggggcc gccatgccgg    1740
cgataatggc ctgcttctcg ccgaaacgtt tggtggcggg accagtgacg aaggcttgag    1800
cgagggcgtg caagattccg aataccgcaa gcgacaggcc gatcatcgtc gcgctccagc    1860
gaaagcggtc ctcgccgaaa atgacccaga gcgctgccgg cacctgtcct acgagttgca    1920
tgataaagaa gacagtcata agtgcggcga cgatagtcat gccccgcgcc caccggaagg    1980
agctgactgg gttgaaggct ctcaagggca tcggtcgaga tcccggtgcc taatgagtga    2040
gctaacttac attaattgcg ttgcgctcac tgcccgcttt ccagtcggga aacctgtcgt    2100
gccagctgca ttaatgaatc ggccaacgcg cggggagagg cggtttgcgt attgggcgcc    2160
agggtggttt ttcttttcac cagtgagacg ggcaacagct gattgccctt caccgcctgg    2220
ccctgagaga gttgcagcaa gcggtccacg ctggtttgcc ccagcaggcg aaaatcctgt    2280
ttgatggtgg ttaacggcgg gatataacat gagctgtctt cggtatcgtc gtatcccact    2340
accgagatat ccgcaccaac gcgcagcccg gactcggtaa tggcgcgcat tgcgcccagc    2400
gccatctgat cgttggcaac cagcatcgca gtgggaacga tgccctcatt cagcatttgc    2460
atggtttgtt gaaaaccgga catggcactc cagtcgcctt cccgttccgc tatcggctga    2520
atttgattgc gagtgagata tttatgccag ccagccagac gcagacgcgc cgagacagaa    2580
cttaatgggc ccgctaacag cgcgatttgc tggtgaccca atgcgaccag atgctccacg    2640
cccagtcgcg taccgtcttc atgggagaaa ataatactgt tgatgggtgt ctggtcagag    2700
acatcaagaa ataacgccgg aacattagtg caggcagctt ccacagcaat ggcatcctgg    2760
tcatccagcg gatagttaat gatcagccca ctgacgcgtt gcgcgagaag attgtgcacc    2820
gccgctttac aggcttcgac gccgcttcgt tctaccatcg acaccaccac gctggcaccc    2880
agttgatcgg cgcgagattt aatcgccgcg acaatttgcg acggcgcgtg cagggccaga    2940
ctggaggtgg caacgccaat cagcaacgac tgtttgcccg ccagttgttg tgccacgcgg    3000
ttgggaatgt aattcagctc cgccatcgcc gcttccactt tttcccgcgt tttcgcagaa    3060
acgtggctgg cctggttcac cacgcgggaa acggtctgat aagagacacc ggcatactct    3120
gcgacatcgt ataacgttac tggtttcaca ttcaccaccc tgaattgact ctcttccggg    3180
cgctatcatg ccataccgcg aaaggttttg cgccattcga tggtgtccgg atctcgacg    3240 ctctccctta tgcgactcct gcattaggaa gcagcccagt agtaggttga ggccgttgag    3300
caccgccgcc gcaaggaatg gtgcatgcaa ggagatggcg cccaacagtc cccggccac    3360
```

```
ggggcctgcc accatacccca cgccgaaaca agcgctcatg agcccgaagt ggcgagcccg    3420
atcttcccca tcggtgatgt cggcgatata ggcgccagca accgcacctg tggcgccggt    3480
gatgccggcc acgatgcgtc cggcgtagag gatcgagatc tcgatcccgc gaaattaata    3540
cgactcacta tagggaatt gtgagcggat aacaattccc ctctagaaat aattttgttt     3600
aactttaaga aggagatata catatgatgc ccaacgtatc actgacagcg aaaggggag    3660
gtcattacat cgaagatcag tgggatacgc aagtcgtcga agcaggagtg ttcgacgact    3720
ggtgggtgca tgtagaggcc tggaataagt ttcttgacaa tctgcgcggc atcaattttt    3780
ccgtcgccag cagtcgctca caagtagcag agtatttggc tgctttggat cgtgaccttc    3840
cggctgacgt tgatcgtcgt ttcgcgggtg cacgtggtca aatcggcagc cccaattact    3900
taccagcacc taaattttt cgtcttgata acgtacaat cgctgaattg acacgtttgt      3960
cgcgcttgac ggatcagccc cacaacaatc gtgatatcga gttaaatcgc gcaaaacgcg    4020
caacaacaaa tcctagccca cctgctcaag ccccgagcga aaaccttaca ctgcgcgacg    4080
tgcaacccct aaaggactcc gcgttacatt atcagtatgt ccttattgat cttcagtccg    4140
cacgcttgcc tgtgtatacc cgcaagactt tcgagcgcga gctggctctg gagtggatca    4200
ttccagatgc agaggaagca taaaccggtt ttaaatatgt cttacagtat cactactcca    4260
tctcagttcg tgttcttgtc atcagcgtgg gccgacccaa tagagttaat taatttatgt    4320
actaatgcct taggaaatca gtttcaaaca caacaagctc gaactgtcgt tcaaagacaa    4380
ttcagtgagg tgtggaaacc ttcaccacaa gtaactgtta ggttccctga cagtgacttt    4440
aaggtgtaca ggtacaatgc ggtattagac ccgctagtca cagcactgtt aggtgcattc    4500
gacactagaa atagaataat agaagttgaa atcaggcga accccacgac tgccgaaacg     4560
ttagatgcta ctcgtagagt agacgacgca acggtggcca taaggagcgc gataaataat    4620
ttaatagtag aattgatcag aggaaccgga tcttataatc ggagctcttt cgagagctct    4680
tctggttttgg tttggacctc tggtcctgca acttgatagt ccggacctgc aggacgcgtg   4740
tcgatcgagc accaccacca ccaccactga gatccggctg ctaacaaagc ccgaaaggaa    4800
gctgagttgg ctgctgccac cgctgagcaa taactagcat aaccccttgg ggcctctaaa    4860
cgggtcttga ggggttttt gctgaaagga ggaactatat ccggattggc gaatgggacg     4920
cgccctgtag cggcgcatta gcgcggcgg gtgtggtggt tacgcgcagc gtgaccgcta     4980
cacttgccag cgccctagcg cccgctcctt tcgctttctt cccttccttt ctcgccacgt    5040
tcgccggctt ccccgtcaa gctctaaatc ggggctccc tttagggttc cgatttagtg      5100
ctttacggca cctcgacccc aaaaaacttg attagggtga tggttcacgt agtgggccat    5160
cgccctgata cacggttttt cgccctttga cgttggagtc cacgttcttt aatagtggac    5220
tcttgttcca aactggaaca acactcaacc ctatctcggt ctattctttt gatttataag    5280
ggattttgcc gatttcggcc tattggttaa aaaatgagct gatttaacaa aaatttaacg    5340
cgaatttaa caaaatatta acgcttacaa tttaggtggc acttttcggg gaaatgtgcg     5400
cggaacccct atttgtttat ttttctaaat acattcaaat atgtatccgc tcatgagaca    5460
ataaccctga taaatgcttc aataatatg aaaaaggaag agtatgagta ttcaacatt     5520
ccgtgtcgcc cttattccct ttttgcggc attttgcctt cctgttttg ctcacccaga      5580
aacgctggtg aaagtaaaag atgctgaaga tcagttgggt gcacgagtgg gttacatcga    5640
actggatctc aacagcggta agatccttga gagttttcgc cccgaagaac gttttccaat    5700
gatgagcact tttaaagttc tgctatgtgg cgcggtatta tcccgtattg acgccgggca    5760
```

-continued

```
agagcaactc ggtcgccgca tacactattc tcagaatgac ttggttgagt actcaccagt    5820
cacagaaaag catcttacgg atggcatgac agtaagagaa ttatgcagtg ctgccataac    5880
catgagtgat aacactgcgg ccaacttact tctgacaacg atcggaggac cgaaggagct    5940
aaccgctttt ttgcacaaca tgggggatca tgtaactcgc cttgatcgtt gggaaccgga    6000
gctgaatgaa gccataccaa acgacgagcg tgacaccacg atgcctgcag caatggcaac    6060
aacgttgcgc aaactattaa ctggcgaact acttactcta gcttcccggc aacaattaat    6120
agactggatg gaggcggata agttgcagg accacttctg cgctcggccc ttccggctgg    6180
ctggtttatt gctgataaat ctggagccgg tgagcgtggg tctcgcggta tcattgcagc    6240
actggggcca gatggtaagc cctcccgtat cgtagttatc tacacgacgg ggagtcaggc    6300
aactatggat gaacgaaata gacagatcgc tgagataggt gcctcactga ttaagcattg    6360
gtaactgtca gaccaagttt actcatatat actttagatt gatttaaaac ttcattttta    6420
atttaaaagg atctaggtga agatcctttt tgataatctc atgaccaaaa tcccttaacg    6480
tgagttttcg ttccactgag cgtcagaccc cgtagaaaag atcaaggat cttcttgaga    6540 tcctttttt ctgcgcgtaa                                                 6560
```

<210> SEQ ID NO 26
<211> LENGTH: 6890
<212> TYPE: DNA
<213> ORGANISM: Artificial Sequence
<220> FEATURE:
<223> OTHER INFORMATION: pET21 plasmid vector carrying the sequence for BSMV-CP fused with a linker and an OAS from a tobacco mosaic virus

<400> SEQUENCE: 26

```
ccccgccagc ctagccgggt cctcaacgac aggagcacga tcatgcgcac ccgtggggcc      60
gccatgccgg cgataatggc ctgcttctcg ccgaaacgtt tggtggcggg accagtgacg     120
aaggcttgag cgagggcgtg caagattccg aataccgcaa gcgacaggcc gatcatcgtc     180
gcgctccagc gaaagcggtc ctcgccgaaa atgacccaga gcgctgccgg cacctgtcct     240
acgagttgca tgataaagaa gacagtcata agtgcggcga cgatagtcat gccccgcgcc     300
caccggaagg agctgactgg gttgaaggct ctcaagggca tcggtcgaga tcccggtgcc     360
taatgagtga gctaacttac attaattgcg ttgcgctcac tgcccgcttt ccagtcggga     420
aacctgtcgt gccagctgca ttaatgaatc ggccaacgcg cggggagagg cggtttgcgt     480
attgggcgcc agggtggttt ttcttttcac cagtgagacg ggcaacagct gattgccctt     540
caccgcctgg ccctgagaga gttgcagcaa gcggtccacg ctggtttgcc ccagcaggcg     600
aaaatcctgt ttgatggtgg ttaacggcgg gatataacat gagctgtctt cggtatcgtc     660
gtatcccact accgagatat ccgcaccaac gcgcagcccg gactcggtaa tggcgcgcat     720
tgcgcccagc gccatctgat cgttggcaac cagcatcgca gtgggaacga tgccctcatt     780
cagcatttgc atggtttgtt gaaaaccgga catggcactc cagtcgcctt cccgttccgc     840
tatcggctga atttgattgc gagtgagata tttatgccag ccagccagac gcagacgcgc     900
cgagacagaa cttaatgggc ccgctaacag cgcgatttgc tggtgaccca atgcgaccag     960
atgctccacg cccagtcgcg taccgtcttc atgggagaaa ataatactgt tgatgggtgt    1020
ctggtcagag acatcaagaa ataacgccgg aacattagtg caggcagctt ccacagcaat    1080
ggcatcctgg tcatccagcg gatagttaat gatcagccca ctgacgcgtt gcgcgagaag    1140
attgtgcacc gccgctttac aggcttcgac gccgcttcgt tctaccatcg acaccaccac    1200
```

```
gctggcaccc agttgatcgg cgcgagattt aatcgccgcg acaatttgcg acggcgcgtg    1260
cagggccaga ctggaggtgg caacgccaat cagcaacgac tgtttgcccg ccagttgttg    1320
tgccacgcgg ttgggaatgt aattcagctc cgccatcgcc gcttccactt tttcccgcgt    1380
tttcgcagaa acgtggctgg cctggttcac cacgcgggaa acggtctgat aagagacacc    1440
ggcatactct gcgacatcgt ataacgttac tggtttcaca ttcaccaccc tgaattgact    1500
ctcttccggg cgctatcatg ccataccgcg aaaggttttg cgccattcga tggtgtccgg    1560
gatctcgacg ctctccctta tgcgactcct gcattaggaa gcagcccagt agtaggttga    1620
ggccgttgag caccgccgcc gcaaggaatg gtgcatgcaa ggagatggcg cccaacagtc    1680
ccccggccac ggggcctgcc accatacccc cgccgaaaca agcgctcatg agcccgaagt    1740
ggcgagcccc atcttcccca tcggtgatgt cggcgatata ggcgcagca accgcacctg    1800 tggcgccggt gatgccggcc acgatgcgtc cggcgtagag gatcgagatc tcgatcccgc    1860
gaaattaata cgactcacta tagggggaatt gtgagcggat aacaattccc ctctagaaat    1920
aattttgttt aactttaaga aggagatata catatgatgc ccaacgtatc actgacagcg    1980 aaaggggag gtcattacat cgaagatcag tgggatacgc aagtcgtcga agcaggagtg    2040
ttcgacgact ggtgggtgca tgtagaggcc tggaataagt ttcttgacaa tctgcgcggc    2100
atcaattttt ccgtcgccag cagtcgctca caagtagcag agtatttggc tgctttggat    2160
cgtgaccttc cggctgacgt tgatcgtcgt ttcgcgggtg cacgtggtca aatcggcagc    2220
cccaattact taccagcacc taaattttt cgtcttgata acgtacaat cgctgaattg    2280 acacgtttgt cgcgcttgac ggatcagccc cacaacaatc gtgatatcga gttaaatcgc    2340
gcaaaacgcg caacaacaaa tcctagccca cctgctcaag ccccgagcga aaaccttaca    2400
ctgcgcgacg tgcaacccct aaaggactcc gcgttacatt atcagtatgt ccttattgat    2460
cttcagtccg cacgcttgcc tgtgtatacc cgcaagactt tcgagcgcga gctggctctg    2520
gagtggatca ttccagatgc agaggaagca taaaccggtt ttaaatatgt cttacagtat    2580
cactactcca tctcagttcg tgttcttgtc atcagcgtgg gccgacccaa tagagttaat    2640
taatttatgt actaatgcct taggaaaatca gtttcaaaca caacaagctc gaactgtcgt    2700
tcaaagacaa ttcagtgagg tgtgaaaacc ttcaccacaa gtaactgtta ggttccctga    2760
cagtgacttt aaggtgtaca ggtacaatgc ggtattagac ccgctagtca cagcactgtt    2820
aggtgcattc gacactagaa atagaataat agaagttgaa aatcaggcga accccacgac    2880
tgccgaaacg ttagatgcta ctcgtagagt agacgacgca acggtggcca taaggagcgc    2940
gataaataat ttaatagtag aattgatcag aggaaccgga tcttataatc ggagctcttt    3000
cgagagctct tctggtttgg tttgaacctc tggtcctgca acttgatagt ccggacctgc    3060
aggacgcgtg tcgacgtttg agagagaaga ttacaaacgt gagagacgga gggcccatgg    3120
aacttacaga agaagtcgtt gatgagttca tggaagatgt ccctatgtcg atcaggcttg    3180
caaagtttcg atctcgaacc ggcctaggct cgtggtattg tttatagaaa taatataaaa    3240
ttaggtttga gagagaagat tacaaacgtg agagacggag ggcccatgga acttacagaa    3300
gaagtcgttg atgagttcat ggaagatgtc cctatgtcga tcaggcttgc aaagtttcga    3360
tctcgaaccg gaaaaagag tgatgtccgc aaagggaaaa atactcgagc accaccacca    3420
ccaccactga gatccggctg ctaacaaagc ccgaaggaa gctgagttgg ctgctgccac    3480
cgctgagcaa taactagcat aaccccttgg ggcctctaaa cgggtcttga ggggttttt    3540
```

-continued

```
gctgaaagga ggaactatat ccggattggc gaatgggacg cgccctgtag cggcgcatta    3600
agcgcggcgg gtgtggtggt tacgcgcagc gtgaccgcta cacttgccag cgccctagcg    3660
cccgctcctt tcgctttctt cccttccttt ctcgccacgt tcgccggctt tccccgtcaa    3720
gctctaaatc gggggctccc tttagggttc cgatttagtg ctttacggca cctcgacccc    3780
aaaaaacttg attagggtga tggttcacgt agtgggccat cgccctgata gacggttttt    3840
cgccctttga cgttggagtc cacgttcttt aatagtggac tcttgttcca aactggaaca    3900
acactcaacc ctatctcggt ctattctttt gatttataag ggattttgcc gatttcggcc    3960
tattggttaa aaaatgagct gatttaacaa aaatttaacg cgaattttaa caaaatatta    4020
acgcttacaa tttaggtggc acttttcggg gaaatgtgcg cggaacccct atttgtttat    4080
ttttctaaat acattcaaat atgtatccgc tcatgagaca ataaccctga taaatgcttc    4140
aataatattg aaaaggaag agtatgagta ttcaacattt ccgtgtcgcc cttattccct    4200
tttttgcggc attttgcctt cctgtttttg ctcacccaga aacgctggtg aaagtaaaag    4260
atgctgaaga tcagttgggt gcacgagtgg gttacatcga actggatctc aacagcggta    4320
agatccttga gagttttcgc cccgaagaac gttttccaat gatgagcact tttaaagttc    4380
tgctatgtgg cgcggtatta tcccgtattg acgccgggca agagcaactc ggtcgccgca    4440
tacactattc tcagaatgac ttggttgagt actcaccagt cacagaaaag catcttacgg    4500
atggcatgac agtaagagaa ttatgcagtg ctgccataac catgagtgat aacactgcgg    4560
ccaacttact tctgacaacg atcggaggac cgaaggagct aaccgctttt ttgcacaaca    4620
tgggggatca tgtaactcgc cttgatcgtt gggaaccgga gctgaatgaa gccataccaa    4680
acgacgagcg tgacaccacg atgcctgcag caatggcaac aacgttgcgc aaactattaa    4740
ctggcgaact acttactcta gcttcccggc aacaattaat agactggatg gaggcggata    4800
aagttgcagg accacttctg cgctcggccc ttccggctgg ctggtttatt gctgataaat    4860
ctggagccgg tgagcgtggg tctcgcggta tcattgcagc actggggcca gatggtaagc    4920
cctcccgtat cgtagttatc tacacgacgg ggagtcaggc aactatggat gaacgaaata    4980
gacagatcgc tgagataggt gcctcactga ttaagcattg gtaactgtca gaccaagttt    5040
actcatatat actttagatt gatttaaaac ttcatttttta atttaaaagg atctaggtga    5100
agatcctttt tgataatctc atgaccaaaa tcccttaacg tgagttttcg ttccactgag    5160
cgtcagaccc cgtagaaaag atcaaaggat cttcttgaga tcctttttt ctgcgcgtaa    5220
tctgctgctt gcaaacaaaa aaaccaccgc taccagcggt ggtttgtttg ccggatcaag    5280
agctaccaac tcttttccg aaggtaactg gcttcagcag agcgcagata ccaaatactg    5340
tccttctagt gtagccgtag ttaggccacc acttcaagaa ctctgtagca ccgcctacat    5400
acctcgctct gctaatcctg ttaccagtgg ctgctgccag tggcgataag tcgtgtctta    5460
ccgggttgga ctcaagacga tagttaccgg ataaggcgca gcggtcgggc tgaacggggg    5520
gttcgtgcac acagcccagc ttggagcgaa cgacctacac cgaactgaga tacctacagc    5580
gtgagctatg agaaagcgcc acgcttcccg aagggagaaa ggcggacagg tatccggtaa    5640
gcggcagggt cggaacagga gagcgcacga gggagcttcc agggggaaac gcctggtatc    5700
tttatagtcc tgtcgggttt cgccacctct gacttgagcg tcgatttttg tgatgctcgt    5760
caggggggcg gagcctatgg aaaaacgcca gcaacgcggc ctttttacgg ttcctggcct    5820
tttgctggcc ttttgctcac atgttctttc ctgcgttatc ccctgattct gtggataacc    5880
gtattaccgc ctttgagtga gctgataccg ctcgccgcag ccgaacgacc gagcgcagcg    5940
```

```
agtcagtgag cgaggaagcg gaagagcgcc tgatgcggta ttttctcctt acgcatctgt    6000
gcggtatttc acaccgcaat ggtgcactct cagtacaatc tgctctgatg ccgcatagtt    6060
aagccagtat acactccgct atcgctacgt gactgggtca tggctgcgcc ccgacacccg    6120
ccaacacccg ctgacgcgcc ctgacgggct tgtctgctcc cggcatccgc ttacagacaa    6180
gctgtgaccg tctccgggag ctgcatgtgt cagaggtttt caccgtcatc accgaaacgc    6240
gcgaggcagc tgcggtaaag ctcatcagcg tggtcgtgaa gcgattcaca gatgtctgcc    6300
tgttcatccg cgtccagctc gttgagtttc tccagaagcg ttaatgtctg gcttctgata    6360
aagcgggcca tgttaagggc ggttttttcc tgtttggtca ctgatgcctc cgtgtaaggg    6420
ggatttctgt tcatgggggt aatgataccg atgaaacgag agaggatgct cacgatacgg    6480
gttactgatg atgaacatgc ccggttactg gaacgttgtg agggtaaaca actggcggta    6540
tggatgcggc gggaccagag aaaaatcact cagggtcaat gccagcgctt cgttaataca    6600
gatgtaggtg ttccacaggg tagccagcag catcctgcga tgcagatccg gaacataatg    6660
gtgcagggcg ctgacttccg cgtttccaga ctttacgaaa cacggaaacc gaagaccatt    6720
catgttgttg ctcaggtcgc agacgttttg cagcagcagt cgcttcacgt tcgctcgcgt    6780
atcggtgatt cattctgcta accagtaagg caacccccgcc agcctagccg ggtcctcaac    6840
gacaggagca cgatcatgcg cacccgtggg gccgccatgc cggcgataat               6890
```